(12) United States Patent
Sugimoto et al.

(10) Patent No.: US 8,686,024 B2
(45) Date of Patent: Apr. 1, 2014

(54) INDOLINE DERIVATIVES

(75) Inventors: Hachiro Sugimoto, Kyoto (JP); Jun Takahashi, Kyoto (JP); Takashi Takahashi, Tokyo (JP); Ichiro Hijikuro, Tokyo (JP)

(73) Assignees: Kyoto University, Kyoto-Shi (JP); Tokyo Institute of Technology, Tokyo (JP)

( * ) Notice: Subject to any disclaimer, the term of this patent is extended or adjusted under 35 U.S.C. 154(b) by 104 days.

(21) Appl. No.: 13/148,011

(22) PCT Filed: Feb. 3, 2010

(86) PCT No.: PCT/JP2010/000644
§ 371 (c)(1),
(2), (4) Date: Aug. 19, 2011

(87) PCT Pub. No.: WO2010/090009
PCT Pub. Date: Aug. 12, 2010

(65) Prior Publication Data
US 2011/0294850 A1 Dec. 1, 2011

(30) Foreign Application Priority Data
Feb. 5, 2009 (JP) .................. 2009-025093

(51) Int. Cl.
*A61K 31/404* (2006.01)
*C07D 209/10* (2006.01)

(52) U.S. Cl.
USPC ........................................ 514/419; 548/468

(58) Field of Classification Search
USPC ................................ 548/491, 468
See application file for complete search history.

(56) References Cited

U.S. PATENT DOCUMENTS

2005/0153980 A1 7/2005 Schadt et al.

FOREIGN PATENT DOCUMENTS

| JP | 2004-2367 A | 1/2004 |
|---|---|---|
| JP | 2005-523310 A | 8/2005 |
| WO | WO 02/48150 A2 | 6/2002 |
| ZA | 7406328 A | 12/1975 |

OTHER PUBLICATIONS

Yu, et al. Document No. 129:16072, retrieved from CAPLUS (1998).*
Hu, et al. Document No. 129:216794, retrieved from CAPLUS (1998).*
Vippangunta, et al. Advanced Drug Delivery Reviews 48 (2001) 3-26.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
International Search Report for PCT/JP2010/000644, mailed on Apr. 13, 2010.
B. Chen et al., "Studies on relationship between the MO reactivity indices and reversible anticholinesterase activity of cuixingning", Chinese Science Bulletin, vol. 35, No. 2, 1990, pp. 139-144.
B. Chen et al., "Synthesis of indolinyl N,N-dimethylcarbamates as reversible anticholinesterase agents", Yaoxue Xuebao, vol. 25, No. 4, 1990, pp. 247-252.
C. N. Lieske et al., "Anticholinesterase Activity of Potential Therapeutic 5-(1,3,3-Trimethylindolinyl) Carbamates", Journal of Enzyme Inhibition, vol. 5, No. 3, 1991, pp. 215-223.
C. N. Lieske et al., "Cholinesterase studies with (R) (+)- and (S)(−)-5-(1,3,3-Trimethylindolinyl)-N-(1-Phenylethyl) Carbamates", Journal of Enzyme Inhibition, vol. 6, No. 4, 1993, pp. 283-291.
H. Meyer et al., "Development and Application of a Radioimmunoassay for physostigmine", Journal of Pharmacology and Experimental Therapeutics, vol. 251, No. 2, 1989, pp. 606-611.
J. Gardner et al., "Some Urethans of Phenolic Quaternary Ammonium Salts", Journal of the American Chemical Society, vol. 69, 1947, pp. 3086-3088.

(Continued)

Primary Examiner — Shawquia Young
(74) Attorney, Agent, or Firm — Birch, Stewart, Kolasch & Birch, LLP

(57) ABSTRACT

The present invention provides a novel indoline derivative or a pharmacologically acceptable salt thereof or a solvate of the derivative or a salt thereof represented by the following formula (1) that has an excellent butyrylcholinesterase inhibitory activity. In the formula, $R_1$ represents an alkyl group, a cycloalkyl group, a heterocycloalkyl group, an aryl group, a heteroaryl group, an arylalkyl group, a heteroarylalkyl group, a cycloalkylalkyl group, a heterocycloalkylalkyl group, a dihydrofurylalkyl group, an alkenyl group, a tetrahydronaphthyl group, or an indanyl group; $R_2$ represents a hydrogen atom, an alkyl group, an arylalkyl group, a cycloalkylalkyl group, a heteroarylalkyl group, a heterocycloalkylalkyl group, an aryl group, or an acyl group; $R_3$ each independently represents a hydrogen atom, an alkyl group, or a dialkylaminocarbonyl group; $R_4$ each independently represents a hydrogen atom or an alkyl group; and $R_5$ represents a hydrogen atom or an alkyl group. Each functional group may have a substituent.

[Formula 1]

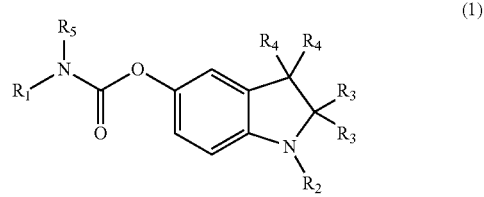

(1)

17 Claims, No Drawings

(56) References Cited

OTHER PUBLICATIONS

M. Ahmed et al., "Synthesis of 1,3,3-trimethyl- and 1,2,3,3-tetramethyl-5-(methyl- and dimethyl-carbamoyloxy) indolines and their methiodides", Journal of Pharmacy and Pharmacology, vol. 17, No. 11, 1965, pp. 728-733.

M. N. Kolosov et al., "Synthetic studies in the series of indole derivatives. I. Synthesis of urethans of 1-methyl-5-hyroxyindoline and 1,3-dimethyl-5-hydroxyindoline (dihydrophysostigmol)", Zhurnal Obshchei Khimii, vol. 23, 1953, pp. 1563-1569.

M. Wang et al., "Studies on relationship between the structure of physostigmine analogs and their anticholinesterase activities", Zhongguo Yaowu Huaxue Zazhi, vol. 7, No. 1, 1997, pp. 59-62.

M. Wang et al., "Synthesis of dihydroindoline compounds and their anticholinesterase activity" Yaoxue Xuebao, vol. 26, No. 2, 1991, pp. 103-110.

M. Zhao et al., "Pharmacokinetics of 5-(1,3,3-trimethylindolinyl) N,N-dimethyl carbamate and its metabolites in the isolated perfused rat livers", Zhongguo Yaolixue Yu Dulixue Zazhi, vol. 6, No. 3, 1992, pp. 228-232.

Q. Yu et al., "Syntheses and Anticholinesterase Activities of (3aS)-N1,N8-Bisnorphenserine, (3aS)-N1,N8-Bisnorphysostigmine, Their Antipodal Isomers, and Other Potential Metabolites of Phenserine", Journal of Medical Chemistry, vol. 41, No. 13, 1998, pp. 2371-2379.

S. Zhang et al., "Synthesis of 5-(1,3,3-trisubstituted) indolinyl N,N-dimethylcarbamates as reversible cholinesterase inhibitors", Yaoxue Xuebao, vol. 22, No. 2, 1987, pp. 107-113.

X. Pei et al., "Syntheses and Biological Evaluation of Ring-C Opened Analogues of the Cholinesterase Inhibitors Physostigmines, Phenserine and Cymserine", Medical Chemistry Research, vol. 9, No. 1, 1999, pp. 50-60.

Extended European Search Report for Appl. No. 10738350.7 dated Aug. 13, 2013.

Greig, N. H. et al, "Phenserine and Ring C Hetero-Analogues: Drug Candidates for the Treatment of Alzheimer's Disease," Medicinal Research Reviews, Jan. 1, 1995, vol. 15, No. 1, pp. 3-31.

\* cited by examiner

INDOLINE DERIVATIVES

TECHNICAL FIELD

The present invention relates to a novel compound useful as a medicament, specifically as a butyrylcholinesterase inhibitor, more specifically as an agent for preventing, treating, or improving dementia or attention deficit hyperactivity disease (ADHD), further specifically as an agent for preventing, treating, or improving Alzheimer-type dementia.

The present application claims priority based on Japanese Patent Application No. 2009-025093 filed in Japan on Feb. 5, 2009 and incorporates the content herein by reference.

BACKGROUND ART

With the rapid increase of the aging population, establishment of methods for treating dementia, such as Alzheimer-type dementia and cerebrovascular dementia, and ADHD is strongly demanded. Development of therapeutic agents for these diseases is studied using various approaches. Since these diseases are associated with a decreased cholinergic function in the brain, development of an acetylcholine precursor inhibitor or an acetylcholine esterase inhibitor was proposed as a promising direction, and these inhibitors are applied in clinical practice. Common examples of the acetylcholine esterase inhibitors include donepezil hydrochloride (1-benzyl-4-[(5,6-dimethoxy-1-indanon)-2-yl]methylpiperidine hydrochloride), rivastigmine (3-[1-(dimethylamino)ethyl]phenyl N-ethyl-N-methylcarbamate), metrifonate (dimethyl (2,2,2-trichloro-1-hydroxyethyl)phosphate), tacrine hydrochloride (1,2,3,4-tetrahydro-9-acridinamine), galanthamine hydrobromide, neostigmine, and physostigmine. Derivatives of these compounds are also under investigation (for example, see Patent Literature 1). For example, it has been mentioned that some physostigmine derivatives can suppress the production of β amyloid precursor protein (βAPP) upon administration (for example, see Patent Literature 2).

Butyrylcholinesterase is a serine hydroxylase that catalyzes hydrolysis of choline esters including acetylcholine and is extensively localized in the nervous system. Therefore, butyrylcholinesterase is thought to play an important role in the nervous system functions, in particular, cholinergic neurotransmission (for example, see Non Patent Literature 1). In fact, an invention has been disclosed that a highly selective butyrylcholinesterase inhibitor, such as cymserine, is used for the prevention or treatment of cognitive impairment associated with aging or Alzheimer's disease (for example, see Patent Literature 3). Some reports have shown that selective inhibition of a butyrylcholinesterase, such as (−)-$N^1$-phenethylnorcymserine (PEC), increased the acetylcholine concentration in the brain, enhanced the learning ability, and decreased the amount of β amyloid peptide in animals with Alzheimer's disease in mice, rats, and the like (for example, see Non Patent Literature 2). Furthermore, both optical isomers of $N^1$-norphenserine were synthesized, and an acetylcholine esterase inhibitory activity and a butyrylcholinesterase inhibitory activity of each optical isomer and a racemate consisting of these optical isomers at a ratio of 1:1 were measured. Both the optical isomers and the racemate all have been found to have both the inhibitory activities. Furthermore, effect on βAPP secretion in cultured human nerve cells was investigated. Both the optical isomers have been reported to have an effect of suppressing the βAPP secretion (for example, see Non Patent Literature 3). In addition, synthesis of a novel highly selective butyrylcholinesterase inhibitory compound derived from phenserine has also been attempted (for example, see Non Patent Literature 4).

CITATION LIST

Patent Literature

Patent Literature 1: European Patent Publication No. 0253372
Patent Literature 2: International Publication No. WO 02/48150
Patent Literature 3: National Publication of International Patent Application No. 2001-500165

Non Patent Literature

Non Patent Literature 1: Darvesh and two others, Nature Reviews/Neuroscience, 2003, 4, 131-8
Non Patent Literature 2: Greig and 14 others, Proceedings of the National Academy of Sciences of the United States of the America, 2005, 102, 47, 17213-8
Non Patent Literature 3: Yu and seven others, Heterocycles, 2003, 61, 529-39
Non Patent Literature 4: Yu and four others, Journal of Medicinal Chemistry, 1999, 42, 1855-61

SUMMARY OF INVENTION

Technical Problem

Of these agents, however, a highly selective acetylcholine esterase inhibitor has actually been used in clinical practice, demonstrating a pharmacological effect on the diseases, and is found to be very useful in terms of adverse drug reactions and the number of doses. Donepezil hydrochloride is a first-line drug because of some disadvantages of other drugs: other drugs have an inadequate effect, cause untoward adverse drug reactions, require many doses per day, are produced only as an injection, and cannot be orally administered. As described above, donepezil hydrochloride is an excellent agent. However, it is obvious that a choline esterase inhibitor that has an even superior effect would be desirable, resulting in increased drug options in clinical practice. In particular, it is considered that adverse effects in the gastrointestinal tract, which are often seen after administration of an acetylcholine esterase inhibitor owing to the neurological distribution thereof, can be avoided in treatment with a butyrylcholinesterase inhibitor. Therefore, a compound with a high selectivity to butyrylcholinesterase can be expected to be a more effective drug in the treatment of Alzheimer-type dementia or the like.

An object of the present invention is to provide a novel compound useful as a medicament, specifically as a butyrylcholinesterase inhibitor, more specifically an agent for preventing, treating, or improving dementia or ADHD, more specifically an agent for preventing, treating or improving Alzheimer-type dementia. Another object is to provide a method for producing the same.

Solution to Problem

The inventors of the present invention conducted various researches to achieve the foregoing objects. As a result, they successfully synthesized a novel compound that has a butyrylcholinesterase inhibitory activity and is more selective to a butyrylcholinesterase than to an acetylcholine esterase, and thus accomplished the present invention.

Specifically, the present invention provides the following [1] to [12].

[1] An indoline derivative or a pharmacologically acceptable salt thereof or a solvate of the derivative or a salt thereof represented by the following formula (1):

[Formula 1]

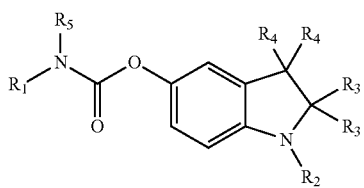

(1)

wherein $R_1$ represents a $C_{1-10}$ alkyl group, a cycloalkyl group, a heterocycloalkyl group, an aryl group, a heteroaryl group, an aryl $C_{1-6}$ alkyl group, a heteroaryl $C_{1-6}$ alkyl group, a cycloalkyl $C_{1-6}$ alkyl group, a heterocycloalkyl $C_{1-6}$ alkyl group, a dihydrofuryl $C_{1-6}$ alkyl group, a $C_{1-6}$ alkenyl group, a tetrahydronaphthyl group, or an indanyl group which may have a substituent; $R_2$ represents a hydrogen atom, or a $C_{1-10}$ alkyl group, an aryl $C_{1-6}$ alkyl group, a cycloalkyl $C_{1-6}$ alkyl group, a heteroaryl $C_{1-6}$ alkyl group, a heterocycloalkyl $C_{1-6}$ alkyl group, an aryl group, or an acyl group which may have a substituent; $R_3$ each independently represents a hydrogen atom, or a $C_{1-10}$ alkyl group or a dialkylaminocarbonyl group which may have a substituent; $R_4$ each independently represents a hydrogen atom, or a $C_{1-10}$ alkyl group which may have a substituent; and $R_5$ represents a hydrogen atom, or a $C_{1-6}$ alkyl group which may have a substituent.

[2] The indoline derivative or a pharmacologically acceptable salt thereof or a solvate of the derivative or a salt thereof according to the [1] represented by the following formula (2):

[Formula 2]

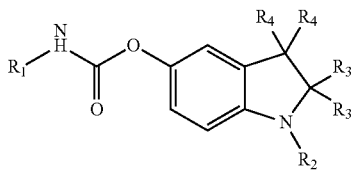

(2)

wherein $R_1$, $R_2$, $R_3$, and $R_4$ have the same meaning as defined in the [1].

[3] The indoline derivative or a pharmacologically acceptable salt thereof or a solvate of the derivative or a salt thereof according to the [1] represented by the following formula (3):

[Formula 3]

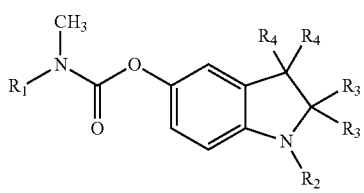

(3)

wherein $R_1$, $R_2$, $R_3$, and $R_4$ have the same meaning as defined in the [1].

[4] The indoline derivative or a pharmacologically acceptable salt thereof or a solvate of the derivative or a salt thereof according to any of the [2] or [3], wherein the $R_1$ is a $C_{1-10}$ alkyl group, a cycloalkyl group, a heterocycloalkyl group, an aryl group, a heteroaryl group, an aryl $C_{3-6}$ alkyl group, a heteroaryl $C_{1-6}$ alkyl group, a cycloalkyl $C_{1-6}$ alkyl group, a heterocycloalkyl $C_{1-6}$ alkyl group, a dihydrofuryl $C_{1-3}$ alkyl group, a $C_{1-6}$ alkenyl group, a tetrahydronaphthyl group, or an indanyl group which may have one or more substituents selected from the group consisting of a $C_{1-10}$ alkyl group, an alkyloxy group, an alkyloxycarbonyl group, an alkylthio group, an acyl group, an alkylamino group, a fluoroalkyl group, a cycloalkyl group, an aryl group, an aryloxy group, an arylalkyl group, a heteroaryl group, a nitro group, a hydroxy group, a cyano group, and a halogen atom and in which two or more substituents may be joined together to form a ring, the $R_2$ is a hydrogen atom, or a $C_{1-10}$ alkyl group, an aryl $C_{1-6}$ alkyl group, a cycloalkyl $C_{1-3}$ alkyl group, a heteroaryl $C_{1-6}$ alkyl group, a heterocycloalkyl $C_{1-6}$ alkyl group, an aryl group, or an acyl group which may have one or more substituents selected from the group consisting of a $C_{1-6}$ alkyl group, an alkyloxy group, an alkylamino group, a dialkylamino group, a fluoroalkyl group, a hydroxy group, an aryl group, an aryloxy group, an arylalkyl group, an acyl group, and a halogen atom and in which two or more substituents may be joined together to form a ring, the $R_3$ is each independently a hydrogen atom, a $C_{1-10}$ alkyl group, or a dialkylaminocarbonyl group, and the $R_4$ is each independently a hydrogen atom, or a $C_{1-10}$ alkyl group which may have a substituent selected from the group consisting of a dialkylaminocarbonyl group and an alkylcarbonylamino group.

[5] The indoline derivative or a pharmacologically acceptable salt thereof or a solvate of the derivative or a salt thereof according to any of the [2] or [3], wherein the $R_1$ is any group selected from the group consisting of the following (1a) to (1i), the $R_2$ is a hydrogen atom, or any group selected from the group consisting of the following (2a) to (2c), the $R_3$ is each independently a hydrogen atom, a $C_{1-10}$ alkyl group, or a dialkylaminocarbonyl group, and the $R_4$ is each independently a hydrogen atom, or a $C_{1-10}$ alkyl group which may have a substituent selected from the group consisting of a dialkylaminocarbonyl group and an alkylcarbonylamino group:

(1a) a $C_{1-10}$ alkyl group which may have a substituent selected from the group consisting of an alkyloxy group, an alkylthio group, and an alkylamino group;

(1b) a cycloalkyl group which may have an alkyl group as a substituent;

(1c) a heterocycloalkyl group which may have an arylalkyl group as a substituent;

(1d) an aryl group which may have one or more substituents selected from the group consisting of a $C_{1-10}$ alkyl group, an alkyloxy group, an alkyloxycarbonyl group, an alkylthio group, an acyl group, an alkylamino group, a fluoroalkyl group, a cycloalkyl group, an aryl group, an aryloxy group, a heteroaryl group, a nitro group, a halogen atom, and a cyano group;

(1e) a heterocycloalkyl $C_{1-6}$ alkyl group which may have an alkyl group or an arylalkyl group as a substituent;

(1f) an aryl $C_{1-6}$ alkyl group which may have one or more substituents selected from the group consisting of an alkyl group, an alkyloxy group, and a halogen atom;

(1g) a dihydrofuryl $C_{1-6}$ alkyl group which may have one or two alkyloxy groups as a substituent;

(1h) a heteroaryl group, a cycloalkyl $C_{1-6}$ alkyl group, a heteroaryl $C_{1-6}$ alkyl group, or a $C_{1-6}$ alkenyl group;

(1i) a benzodioxolyl group, an indanyl group, a dihydrobenzofuryl group, a dihydrobenzodioxynyl group, a benzodioxolyl group, or a tetrahydronaphthyl group;

(2a) a phenyl $C_{1-6}$ alkyl group or a naphthyl $C_{1-6}$ alkyl group which may have one or more substituents selected from the group consisting of an alkyloxy group, a fluoroalkyl group, an alkylamino group, a dialkylamino group, an acyl group, a hydroxy group, an aryloxy group, and a halogen atom;

(2b) a heteroaryl $C_{1-6}$ alkyl group which may have an arylalkyl group or an alkyl group as a substituent; and (2c) a phenyl group, a benzoyl group, a $C_{1-10}$ alkyl group, a cycloalkyl $C_{1-6}$ alkyl group, or a heterocycloalkyl $C_{1-6}$ alkyl group.

[6] The indoline derivative or a pharmacologically acceptable salt thereof or a solvate of the derivative or a salt thereof according to any of the [2] or [3], wherein the $R_1$ is any group selected from the group consisting of the following (1a, to (1 h'), the $R_2$ is a hydrogen atom, or any group selected from the group consisting of the following (2a') to (2c'), the $R_3$ is each independently a hydrogen atom, a $C_{1-10}$ alkyl group, or a dialkylaminocarbonyl group, and the $R_4$ is each independently a hydrogen atom, or a $C_{1-10}$ alkyl group which may have a substituent selected from the group consisting of a dialkylaminocarbonyl group and an alkylcarbonylamino group:

(1a') a $C_{1-10}$ alkyl group which may have a substituent selected from the group consisting of a methoxy group, a methylthio group, a furfurylthio group, and a dimethylamino group;

(1b') a cyclopropyl group, a cyclohexyl group, a cyclooctyl group, or a 4-tert-butylcyclohexyl group;

(1c') a piperidinyl group which may have a phenyl $C_{1-6}$ alkyl group as a substituent; (1d) a phenyl group which may have one or more substituents selected from the group consisting of a methyl group, an isopropyl group, an n-butyl group, a t-butyl group, a methoxy group, an n-hexyloxy group, an ethoxycarbonyl group, a methylthio group, an acetyl group, a dimethylamino group, a trifluoromethyl group, a cyclohexyl group, a phenyl group, a phenoxy group, a 1H-pyrrol-1-yl group, a nitro group, a halogen atom, and a cyano group;

(1e') a tetrahydrofuryl $C_{1-6}$ alkyl group, a piperidinyl $C_{1-6}$ alkyl group, or a pyrrolidinyl $C_{1-6}$ alkyl group which may have an alkyl group or a phenyl $C_{1-6}$ alkyl group as a substituent;

(1f) a phenyl $C_{1-6}$ alkyl group or a naphthyl $C_{1-6}$ alkyl group which may have one or more substituents selected from the group consisting of a methyl group, an isopropyl group, a methoxy group, an isopropylopoxy group, and a halogen atom;

(1 g') a dihydrofuryl $C_{1-6}$ alkyl group which may have one or two methoxy groups as a substituent;

(1h') a quinolyl group, a pyridyl group, a cyclohexyl $C_{1-6}$ alkyl group, a 1-adamantyl $C_{1-6}$ alkyl group, a furyl $C_{1-6}$ alkyl group, a pyridyl $C_{1-6}$ alkyl group, a thienyl $C_{1-6}$ alkyl group, a 2-methylallyl group, a benzodioxolyl group, an indanyl group, a dihydrobenzofuryl group, a dihydrobenzodioxynyl group, or a tetrahydronaphthyl group;

(2a') a phenyl $C_{1-6}$ alkyl group or a naphthyl $C_{1-6}$ alkyl group which may have one or more substituents selected from the group consisting of a methoxy group, a trifluoromethyl group, a dimethylamino group, an acetyl group, a hydroxy group, a phenoxy group, a 3-dimethylaminopropoxy group, a methoxycarbonyl group, and a halogen atom;

(2b') an indolyl $C_{1-6}$ alkyl group which may have a benzyl group or a methyl group as a substituent; and (2c') a phenyl group, a benzoyl group, a $C_{1-10}$ alkyl group, a cyclohexyl $C_{1-6}$ alkyl group, a pyridyl $C_{1-6}$ alkyl group, a furyl $C_{1-6}$ alkyl group, a pyrrolyl $C_{1-6}$ alkyl group, a quinolyl $C_{1-6}$ alkyl group, a benzodioxolyl $C_{1-6}$ alkyl group, or a tetrahydrofuryl $C_{1-6}$ alkyl group.

[7] The indoline derivative or a pharmacologically acceptable salt thereof or a solvate of the derivative or a salt thereof according to any of the [2] or [3], wherein the $R_1$ is a methyl group, an ethyl group, an n-propyl group, an n-hexyl group, a 2-heptyl group, a 2-methylpropyl group, a 2,2-dimethylpropyl group, a 3,3-dimethylbutyl group, a 3-methoxypropyl group, a 1-methoxybutan-2-yl group, a 3-(dimethylamino) propyl group, a 2-(dimethylamino)ethyl group, a 3-dimethylamino-2,2-dimethylpropyl group, a 3-methylthiopropyl group, a 2-(furfurylthio)ethyl group, a cyclohexyl group, a cyclopropyl group, a cyclooctyl group, a 4-tert-butylcyclohexyl group, a cyclohexylmethyl group, a 1-adamantanemethyl group, a 2-tetrahydrofurylmethyl group, a 3-tetrahydrofurylmethyl group, a 4-tetrahydropyranylmethyl group, a 2-(1-benzylpiperidin-4-yl)ethyl group, a 4-methylphenyl group, a 4-isopropylphenyl group, a 3,4-dimethylphenyl group, a 4-methoxyphenyl group, a 4-dimethylaminophenyl group, a 3,4-dimethoxyphenyl group, a 2,3-dihydro-1,4-benzodioxin-6-yl group, a 5-benzo[d][1,3]dioxolyl group, a 5-indanyl group, a 2,3-dihydro-1-benzofuran-5-yl group, a benzyl group, a phenethyl group, a 1-phenylethyl group, a 4-isopropylphenethyl group, a 4-methylphenethyl group, a 4-methylbenzyl group, a 2-methylphenethyl group, a 2,4-dimethylphenethyl group, a 4-methoxybenzyl group, a 3-methoxybenzyl group, a 4-methoxyphenethyl group, a 2-methoxyphenethyl group, a 1-(p-tolyl)ethyl group, a 4-chlorophenethyl group, a 2,4-dichlorophenethyl group, a furfuryl group, a 2-thiophenemethyl group, a 2-pyridylmethyl group, a 4-pyridylmethyl group, a 2-(4-pyridyl)ethyl group, a 2-(3-pyridyl)ethyl group, a 1-benzylpiperidin-4-yl group, a 2-methylallyl group, a 1,2,3,4-tetrahydronaphthalen-1-yl group, a (2,5-dihydro-2,5-dimethoxyfuran-2-yl)methyl group, or a 2-indanyl group, the $R_2$ is a hydrogen atom, a 3,3-dimethylbutyl group, a benzyl group, a 3-hydroxybenzyl group, a 2-hydroxybenzyl group, a 4-hydroxybenzyl group, a 4-hydroxy-3-methoxybenzyl group, a phenethyl group, a 4-pyridylmethyl group, a 3-pyridylmethyl group, a 2-pyridylmethyl group, an indol-3-ylmethyl group, a (pyrrol-2-yl)methyl group, or a cyclohexylmethyl group, the $R_3$ is each independently a hydrogen atom, a methyl group, or a di-n-propylaminocarbonyl group, and the $R_4$ is each independently a hydrogen atom, a methyl group, a 2-acetamideethyl group, or a di-n-propylaminocarbonylmethyl group.

[8] The indoline derivative or a pharmacologically acceptable salt thereof or a solvate of the derivative or a salt thereof according to the [1], which is selected from the following compounds: (1) 1-benzylindolin-5-yl 4-isopropyl phenyl carbamate, (2) 1-phenethyl indolin-5-yl 4-isopropyl phenyl carbamate, (3) 1-(3,3-dimethyl butyl)indolin-5-yl 4-isopropyl phenyl carbamate, (4) 1-benzylindolin-5-yl 4-methoxyphenyl carbamate, (5) 1-benzylindolin-5-yl 2,3-dihydro-1,4-benzodioxin-6-yl carbamate, (6) 1-benzylindolin-5-yl 5-benzo[d][1,3]dioxolyl carbamate, (7) 1-benzylindolin-5-yl 2,3-dihydro-1-benzofuran-5-yl carbamate, (8) 1-benzylindolin-5-yl benzylcarbamate, (9) 1-benzylindolin-5-yl phenethyl carbamate, (10) 1-benzylindolin-5-yl n-hexyl carbamate, (11) 1-benzyl indolin-5-yl furfuryl carbamate, (12) 1-benzylindolin-5-yl (S)-1-phenyl ethyl carbamate, (13) 1-benzylindolin-5-yl cyclohexyl carbamate, (14) 1-(4-pyridyl methyl)indolin-5-yl 4-isopropyl phenyl carbamate, (15) 1-(3-pyridyl methyl)indolin-5-yl 4-isopropyl phenyl carbamate, (16) 1-benzylindolin-5-yl 4-methoxybenzylcarbamate, (17) 1-benzylindolin-5-yl 4-methoxyphenethyl carbamate, (18) 1-benzylindolin-5-yl 4-isopropyl phenethyl carbamate, (19) 1-benzylindolin-5-yl cyclohexyl methyl carbamate, (20) 1-benzylindolin-5-yl 2-methyl propyl carbamate, (21) 1-benzylindolin-5-yl cyclopropyl carbamate, (22) 1-benzylindolin-5-yl 3,3-dimethyl butyl carbamate, (23) 1-benzylindolin-5-yl 4-tert-butyl cyclohexyl carbamate, (24) 1-benzylindolin-5-yl 2-indanyl carbamate, (25) 1-benzylindolin-5-yl cyclooctyl carbamate, (26) 1-benzylindolin-5-yl 1-methoxybutan-2-yl carbamate, (27) 1-benzylindolin-5-yl 1-adamantane methyl carbamate, (28) 1-benzylindolin-5-yl 3-methyl thiopropyl carbamate, (29) 1-benzylindolin-5-yl 2-heptyl carbamate, (30) 1-benzylindolin-5-yl 2-tetrahydrofuryl methyl carbamate, (31) 1-benzylindolin-5-yl 2-methyl allyl carbamate, (32) 1-benzylindolin-5-yl 2-(furfuryl thio)ethyl carbamate, (33) 1-benzylindolin-5-yl 4-methyl phenyl carbamate, (34) 1-benzylindolin-5-yl ethyl carbamate, (35) 1-(2-pyridyl methyl)indolin-5-yl 4-isopropyl phenyl carbamate, (36) 1-(3-hydroxybenzyl)indolin-5-yl 4-isopropyl phenyl carbamate, (37) 1-[(pyrrol-2-yl)methyl]indolin-5-yl 4-isopropyl phenyl carbamate, (38) 1-(2-hydroxybenzyl)indolin-5-yl 4-isopropyl phenyl carbamate, (39) 1-(4-hydroxy-3-methoxybenzyl)indolin-5-yl 4-isopropyl phenyl carbamate, (40) 1-(cyclohexylmethyl)indolin-5-yl 4-isopropyl phenyl carbamate, (41) 1-(4-hydroxybenzyl)indolin-5-yl 4-isopropyl phenyl carbamate, (42) 1-(indol-3-ylmethyl)indolin-5-yl 4-isopropyl phenyl carbamate, (43) 1-benzylindolin-5-yl 5-indanyl carbamate, (44) 1-benzylindolin-5-yl 4-methyl phenethyl carbamate, (45) 1-benzylindolin-5-yl 1,2,3,4-tetrahydronaphthalen-1-yl carbamate, (46) 1-benzylindolin-5-yl 1-(p-tolyl)ethyl carbamate, (47) 1-benzylindolin-5-yl 2-thiophene methyl carbamate, (48) 1-benzylindolin-5-yl 4-methyl benzylcarbamate, (49) 1-benzylindolin-5-yl 3-methoxybenzylcarbamate, (50) 1-benzylindolin-5-yl 2-pyridyl methyl carbamate, (51) 1-benzylindolin-5-yl 4-pyridyl methyl carbamate, (52) 1-benzylindolin-5-yl 4-chlorophenethyl carbamate, (53) 1-benzylindolin-5-yl 3,4-dimethyl phenyl carbamate, (54) 1-benzylindolin-5-yl n-propyl carbamate, (55) 1-benzylindolin-5-yl 2-methyl phenethyl carbamate, (56) 1-benzylindolin-5-yl 2,4-dimethyl phenethyl carbamate, (57) 1-benzylindolin-5-yl 2-methoxyphenethyl carbamate, (58) 1-benzylindolin-5-yl 2,4-dichlorophenethyl carbamate, (59) 1-benzylindolin-5-yl 2-(4-pyridyl)ethyl carbamate, (60) 1-benzylindolin-5-yl 2-(3-pyridyl)ethyl carbamate, (61) 1-benzylindolin-5-yl (2,5-dihydro-2,5-dimethoxyfuran-2-yl)methyl carbamate, (62) indolin-5-yl benzylcarbamate, (63) 1-benzylindolin-5-yl methyl carbamate, (64) 1-benzylindolin-5-yl 4-dimethyl aminophenyl carbamate, (65) 1-benzylindolin-5-yl 3-(dimethylamino)propyl carbamate, (66) 1-benzylindolin-5-yl 1-benzylpiperidin-4-yl carbamate, (67) 1-benzylindolin-5-yl 2-(1-benzylpiperidin-4-yl)ethyl carbamate, (68) 1-benzylindolin-5-yl 3,4-dimethoxyphenyl carbamate, (69) 1-benzyl-3,3-dimethyl indolin-5-yl 4-isopropyl phenyl carbamate, (70) 1-benzyl-3-methylindolin-5-yl 4-isopropyl phenyl carbamate, (71) 1-(2-pyridyl methyl)indolin-5-yl n-hexyl carbamate, (72) 1-(2-pyridyl methyl)indolin-5-yl cyclohexyl methyl carbamate, (73) 1-(2-pyridyl methyl)indolin-5-yl cyclohexyl carbamate, (74) 1-(2-pyridyl methyl)indolin-5-yl benzylcarbamate, (75) 1-(2-pyridyl methyl)indolin-5-yl 4-dimethyl aminophenyl carbamate, (76) 1-benzylindolin-5-yl 2,2-dimethyl propyl carbamate, (77) 1-benzylindolin-5-yl 3-tetrahydrofuryl methyl carbamate, (78) 1-benzylindolin-5-yl 3-dimethylamino-2,2-dimethyl propyl carbamate, (79) 3-(2-acetamide ethyl)-1-benzylindolin-5-yl 4-isopropyl phenyl carbamate, (80) 1-benzyl-3-(di-n-propyl aminocarbonyl methyl)indolin-5-yl 4-isopropyl phenyl carbamate, (81) 1-benzyl-3-(di-n-propyl aminocarbonyl methyl)-2-methylindolin-5-yl 4-isopropyl phenyl carbamate, (82) O-(1-benzylindolin-5-yl)-N-(cyclohexylmethyl)-N-methyl carbamate, (83) O-(1-benzyl-3,3-dimethyl indolin-5-yl)-N-(cyclohexylmethyl)-N-methyl carbamate, (84) O-(1-benzyl-3,3-dimethyl indolin-5-yl)-N-methyl-N-(4-tetrahydropyranyl methyl)carbamate, (85) N-methyl-O-[1-(2-pyridyl methyl)-3,3-dimethyl indolin-5-yl]-N-(4-tetrahydropyranyl methyl)carbamate, (86) N-methyl-O-[1-(3-pyridyl methyl)-3,3-dimethyl indolin-5-yl]-N-(4-tetrahydropyranyl methyl)carbamate, and (87) N-methyl-O-[1-(4-pyridyl methyl)-3,3-dimethyl indolin-5-yl]-N-(4-tetrahydropyranyl methyl)carbamate.

[9] A medicament comprising at least one selected from indoline derivatives or pharmacologically acceptable salts thereof or solvates of the derivatives or salts thereof according to the [1] to [8] as an active ingredient.

[10] The medicament according to the [9], which is a butyrylcholinesterase inhibitor.

[11] The medicament according to the [9], which is an agent for treating, preventing, or improving dementia or attention deficit hyperactivity disease.

[12] The medicament according to the [11], wherein the dementia is Alzheimer-type dementia.

Advantageous Effects of Invention

The present invention can provide a compound or a pharmacologically acceptable salt thereof or a solvate of the derivative or a salt thereof which compound is a novel indoline derivative that is more selective to a butyrylcholinesterase than to an acetylcholine esterase and has a favorable butyrylcholinesterase inhibitory activity.

DESCRIPTION OF EMBODIMENTS

A compound described in the present specification and the present invention includes all isomers such as geometrical isomers, optical isomers due to asymmetric carbon atoms, stereoisomers, and tautomers, isomer mixtures, and isotopes that occur based on the structure of the compound, except when the structural formula or the name of the compound clearly refers to a specific structure isomer. Of these isomers, a compound described in the present specification and the present invention may be one isomer, a mixture of two or more isomers such as a racemate, or any one isotope. Furthermore, a crystalline polymorph may exist. The crystalline polymorph is not limited either and may be any single crystal form or a mixture, or a solvate as well as an anhydride.

In the present specification and the present invention, the expression that a functional group "has a substituent" means that a part or all of hydrogen atoms in the functional group are substituted with a group or an atom that is not a hydrogen atom.

The indoline derivative of the present invention is a compound (hereinafter, also referred to as a compound (I)) represented by the following formula (1):

[Formula 4]

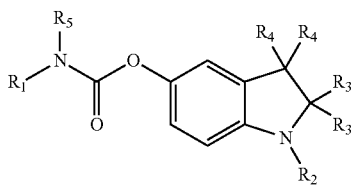

(1)

wherein $R_1$ represents a $C_{1-10}$ alkyl group, a cycloalkyl group, a heterocycloalkyl group, an aryl group, a heteroaryl group, an aryl $C_{1-6}$ alkyl group, a heteroaryl $C_{1-6}$ alkyl group, a cycloalkyl $C_{1-6}$ alkyl group, a heterocycloalkyl $C_{1-6}$ alkyl group, a dihydrofuryl $C_{1-6}$ alkyl group, a $C_{1-6}$ alkenyl group, a tetrahydronaphthyl group, or an indanyl group which may have a substituent; $R_2$ represents a hydrogen atom, or a $C_{1-10}$ alkyl group, an aryl $C_{1-6}$ alkyl group, a cycloalkyl $C_{1-6}$ alkyl group, a heteroaryl $C_{1-6}$ alkyl group, a heterocycloalkyl $C_{1-6}$ alkyl group, an aryl group, or an acyl group which may have a substituent; $R_3$ each independently represents a hydrogen atom, or a $C_{1-10}$ alkyl group or a dialkylaminocarbonyl group which may have a substituent; $R_4$ each independently represents a hydrogen atom, or a $C_{1-10}$ alkyl group which may have a substituent; and $R_5$ represents a hydrogen atom, or a $C_{1-6}$ alkyl group which may have a substituent.

Of these compounds, the indoline derivative of the present invention is preferably a compound (hereinafter, also referred to as a compound (I-1)) represented the following formula (2) or a compound (hereinafter, also referred to as a compound (I-3)) represented by the following formula (3). In the present specification and the present invention, the "compound (I)" means a compound including the compound (I-1) and the compound (I-3).

[Formula 5]

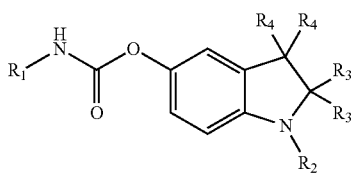

(2)

wherein $R_1$, $R_2$, $R_3$, and $R_4$ have the same meaning as defined above.

[Formula 6]

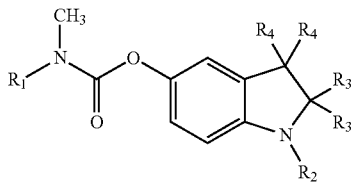

(3)

wherein $R_1$, $R_2$, $R_3$, and $R_4$ have the same meaning as defined above.

[About $R_1$]

$R_1$ represents a $C_{1-10}$ alkyl group, a cycloalkyl group, a heterocycloalkyl group, an aryl group, a heteroaryl group, an aryl $C_{1-6}$ alkyl group, a heteroaryl $C_{1-6}$ alkyl group, a cycloalkyl $C_{1-6}$ alkyl group, a heterocycloalkyl $C_{1-6}$ alkyl group, a dihydrofuryl $C_{1-6}$ alkyl group, a $C_{1-6}$ alkenyl group, a tetrahydronaphthyl group, or an indanyl group which may have a substituent.

The "$C_{1-10}$ alkyl group" represented by $R_1$ means a straight or branched alkyl group having one to 10 carbon atoms. Specific examples of the "$C_{1-10}$ alkyl group" include a methyl group, an ethyl group, a propyl group, an isopropyl group, a butyl group, an isobutyl group, a t-butyl group, an s-butyl group, a 1-methylpropyl group, a 2-methylpropyl group, a pentyl group, an isopentyl group, a neopentyl group, a t-pentyl group, a 1-methylbutyl group, a 2,2-dimethylpropyl group, a hexyl group, a 3,3-dimethylbutyl group, a heptyl group, a 2-heptyl group, an octyl group, a 1-methylheptyl group, a nonyl group, and a decyl group.

$R_1$ of the compound (I) is preferably an alkyl group having two to six carbon atoms.

$R_1$ of the compound (I) may be an unsubstituted $C_{1-10}$ alkyl group or a $C_{1-10}$ alkyl group that has a substituent. Examples of the substituent include alkyl groups such as a methyl group, an ethyl group, a t-butyl group, and an n-butyl group; aryl groups such as a phenyl group and a naphthyl group; cycloalkyl groups such as a cyclopentyl group and a cyclohexyl group; alkyloxy groups such as a methoxy group, an ethoxy group, and an n-hexyloxy group; aryloxy groups such as a phenoxy group and a naphthyloxy group; halogen atoms such as a fluorine atom, a chlorine atom, a bromine atom, and an iodine atom; fluoro $C_{1-6}$ alkyl groups such as a perfluoromethyl group and a perfluoroethyl group; a nitro group; monoalkylamino groups such as a methylamino group and an ethylamino group and dialkylamino groups such as a dimethylamino group and a diethylamino group; acyl groups such as a formyl group, an acetyl group, a propionyl group, a butyryl group, an isobutyryl group, a varelyl group, an isovarelyl group, a pivaloyl group, a hexanoyl group, a benzoyl group, an aroyl group, and a nicotinoyl group; a nitro group; heteroaryl groups such as a furyl group, a pyrrolyl group, a pyranyl group, a pyridyl group, and an indolyl group; a cyano group; aryl $C_{1-6}$ alkyl groups such as a benzyl group and a phenethyl group; thio groups such as an alkylthio group and a furylalkylthio group; alkyloxycarbonyl groups such as a methoxycarbonyl group and an ethoxycarbonyl group; a dialkyloxydihydrofuryl group; and a hydroxy group.

$R_1$ of the compound (I) is preferably an unsubstituted $C_{1-10}$ alkyl group or a $C_{1-10}$ alkyl group that has a substituent selected from the group consisting of an alkyloxy group, an alkylthio group, and an alkylamino group. Of these groups, $R_1$ of the compound (I) is more preferably an unsubstituted $C_{1-10}$ alkyl group or a $C_{1-10}$ alkyl group that has a substituent selected from the group consisting of a methoxy group, a methylthio group, a furfurylthio group, and a dimethylamino group.

More specifically, $R_1$ of the compound (I) is preferably a methyl group, an ethyl group, an n-propyl group, a 2-propyl group, a 2-methylpropyl group, a 2,2-dimethylpropyl group, a 3,3-dimethylbutyl group, an n-hexyl group, a 2-heptyl group, a 1-methoxybutan-2-yl group, a 3-methoxypropyl group, a 3-methylthiopropyl group, a 2-(furfurylthio)ethyl group, a 2-(dimethylamino)ethyl group, a 3-(dimethylamino)propyl group, or a 3-dimethylamino-2,2-dimethylpropyl group.

Examples of the "cycloalkyl group" represented by $R_1$ include a cyclopropyl group, a cyclobutyl group, a cyclopentyl group, a cyclohexyl group, a cycloheptyl group, and a cyclooctyl group. $R_1$ of the compound (I) is preferably a cycloalkyl group having three to eight carbon atoms, particularly preferably a cyclopropyl group, a cyclohexyl group, or a cyclooctyl group.

$R_1$ of the compound (I) may be an unsubstituted cycloalkyl group or a cycloalkyl group that has a substituent. Examples of the substituent include the same substituents as the substituents mentioned above as the substituents of a "$C_{1-10}$ alkyl group." A substituent of a cycloalkyl group on $R_1$ is preferably an alkyl group, more preferably a t-butyl group.

$R_1$ of the compound (I) is particularly preferably a cyclopropyl group, a cyclohexyl group, a cyclooctyl group, or a 4-tert-butylcyclohexyl group.

Examples of the "heterocycloalkyl group" represented by $R_1$ include a group in which one of carbon atoms constituting the above-mentioned cycloalkyl group is substituted with a different atom such as, for example, an oxygen atom, a nitrogen atom, and a sulfur atom. Specific examples of the "heterocycloalkyl group" include an aziridyl group, a piperidinyl group, a pyrrolidinyl group, a piperazinyl group, an epoxy group, an oxetanyl group, a tetrahydrofuryl group, and a morpholinyl group. $R_1$ of the compound (I) is more preferably a piperidinyl group, a pyrrolidinyl group, a piperazinyl group, or a morpholinyl group, further preferably a piperidinyl group.

$R_1$ of the compound (I) may be an unsubstituted heterocycloalkyl group or a heterocycloalkyl group that has a substituent. Examples of the substituent include the same substituents as the substituents mentioned above as the substituents of a "$C_{1-10}$ alkyl group." A substituent of a heterocycloalkyl group on $R_1$ is preferably an arylalkyl group such as a phenyl $C_{1-6}$ alkyl group, more preferably a benzyl group.

$R_1$ of the compound (I) is particularly preferably a piperidinyl group which may have a phenyl $C_{1-6}$ alkyl group as a substituent, more preferably a 1-benzylpiperidin-4-yl group.

Examples of the "aryl group" represented by $R_1$ include monocyclic, bicyclic, or tricyclic aryl groups such as a phenyl group, an indenyl group, a naphthyl group, an azulenyl group, a heptalenyl group, a phenanthrenyl group, an anthracenyl group, and a fluorenyl group. $R_1$ of the compound (I) is preferably a phenyl group or a naphthyl group, more preferably a phenyl group.

$R_1$ of the compound (I) may be an unsubstituted aryl group or an aryl group that has a substituent. Examples of the substituent include the same substituents as the substituents mentioned above as the substituents of a "$C_{1-10}$ alkyl group."

Furthermore, $R_1$ of the compound (I) may be an aryl group that has one substituent or an aryl group that has two or more substituents. When an aryl group has two or more substituents, the two or more substituents may be the same substituents or a combination of different substituents. Furthermore, when an aryl group has two or more substituents, the two or more substituents may be joined together with each other to form a ring.

$R_1$ of the compound (I) is preferably a phenyl group that has a substituent. Of these groups, $R_1$ of the compound (I) is preferably a phenyl group that has a substituent on the 4th carbon atom, but may be a phenyl group that has the same or different substituents on the 4th and 3rd carbon atoms or on the 3rd and 5th carbon atoms. Furthermore, substituents introduced at the 4th and 3rd positions of a phenyl group may be bonded to each other to form a ring.

When substituents are not bonded to each other to form a ring, a phenyl group is preferably a phenyl group that has one or more substituents selected from the group consisting of a $C_{1-10}$ alkyl group, an alkyloxy group, an alkyloxycarbonyl group, an alkylthio group, an acyl group, an alkylamino group, a fluoroalkyl group, a cycloalkyl group, an aryl group, an aryloxy group, a heteroaryl group, a nitro group, a halogen atom, and a cyano group. Of these groups, the phenyl group is preferably a phenyl group that has one or more substituents selected from the group consisting of a methyl group, an isopropyl group, an n-butyl group, a t-butyl group, a methoxy group, an n-hexyloxy group, an ethoxycarbonyl group, a methylthio group, an acetyl group, a dimethylamino group, a trifluoromethyl group, a cyclohexyl group, a phenyl group, a phenoxy group, a 1H-pyrrol-1-yl group, a nitro group, a halogen atom, and a cyano group, more preferably a phenyl group that has one or more substituents selected from the group consisting of a methyl group, an isopropyl group, a methoxy group, and a dimethylamino group.

Meanwhile, when substituents are joined together with each other to form a ring, a phenyl group is preferably a phenyl group in which two or more substituents selected from the group consisting of a $C_{1-10}$ alkyl group, an alkyloxy group, and a hydroxy group are joined together with each other to form a ring. Examples of such a phenyl group in which substituents are joined together with each other to form a ring include a benzodioxolyl group (piperonyl group), an indanyl group, a dihydrobenzofuryl group, and a dihydrobenzodioxynyl group.

More specifically, $R_1$ of the compound (I) is preferably a phenyl group, a naphthyl group, a 4-methylphenyl group, a 4-isopropylphenyl group, a 4-n-butylphenyl group, a 4-tert-butylphenyl group, a 3,4-dimethylphenyl group, a 4-methoxyphenyl group, a 3-methoxyphenyl group, a 3,4-dimethoxyphenyl group, a 4-n-hexyloxyphenyl group, a 5-tert-butyl-2-methoxyphenyl group, a 4-(ethoxycarbonyl)phenyl group, a 3-methylthiophenyl group, a 4-acetylphenyl group, a 4-dimethylaminophenyl group, a 3-trifluoromethylphenyl group, a 3-methoxy-5-(trifluoromethyl)phenyl group, a 4-cyclohexylphenyl group, a 4-phenylphenyl group, a 4-phenoxyphenyl group, a 3-phenoxyphenyl group, a 4-(1H-pyrrol-1-yl)phenyl group, a 4-chlorophenyl group, a 3-bromophenyl group, a 2-cyanophenyl group, a 2,3-dihydro-1,4-benzodioxin-6-yl group, a 5-benzo[d][1,3]dioxolyl group, a 5-indanyl group, or a 2,3-dihydro-1-benzofuran-5-yl group, more preferably a 4-methylphenyl group, a 4-isopropylphenyl group, a 3,4-dimethylphenyl group, a 4-methoxyphenyl group, a 4-dimethylaminophenyl group, a 3,4-dimethoxyphenyl group, a 2,3-dihydro-1,4-benzodioxin-6-yl group, a 5-benzo[d][1,3]dioxolyl group, a 5-indanyl group, or a 2,3-dihydro-1-benzofuran-5-yl group.

Examples of the "heteroaryl group" represented by $R_1$ include a group in which one of carbon atoms constituting the above-mentioned aryl group is substituted with a different atom such as, for example, an oxygen atom, a nitrogen atom, and a sulfur atom. Specific examples of the "heteroaryl group" include a pyrrolyl group, a pyridyl group, a pyrimidyl group, a furyl group, a thienyl group, a pyranyl group, an imidazolyl group, an oxazolyl group, a thiazolyl group, an indolyl group, and a quinolyl group. $R_1$ of the compound (I) is preferably a 5-membered ring, a 6-membered ring, or a heteroaryl group formed by condensing two of these rings, more preferably a pyridyl group, a quinolyl group, a furyl group, a furyl group, a pyrrolyl group, a pyranyl group, an indolyl group, or a thienyl group, further preferably a pyridyl group or a quinolyl group.

$R_1$ of the compound (I) may be an unsubstituted heteroaryl group or a heteroaryl group that has a substituent. Examples of the substituent include the same substituents as the substituents mentioned above as the substituents of a "$C_{1-10}$ alkyl group."

More specifically, $R_1$ of the compound (I) is preferably a quinolin-6-yl group or a pyridin-4-yl group.

The "$C_{1-6}$ alkyl group" in a cycloalkyl $C_{1-6}$ alkyl group, an aryl $C_{1-6}$ alkyl group, a heteroaryl $C_{1-6}$ alkyl group, a heterocycloalkyl $C_{1-6}$ alkyl group, and a dihydrofuryl $C_{1-6}$ alkyl group described below means a straight or branched alkyl group having one to six carbon atoms. Specific examples include a methyl group, an ethyl group, a propyl group, a butyl group, and a 1-methyl ethyl group.

The "cycloalkyl $C_{1-6}$ alkyl group" represented by $R_1$ means a group in which at least one hydrogen atom in the above-mentioned $C_{1-6}$ alkyl group is substituted with a cycloalkyl group. The cycloalkyl group may be, for example, a monocyclic cycloalkyl group, such as a cyclopropyl group, a cyclobutyl group, a cyclopentyl group, a cyclohexyl group, a cycloheptyl group, and a cyclooctyl group, or a polycyclic cycloalkyl group, such as an adamantyl group and a norbornyl group. $R_1$ of the compound (I) is preferably a group in which at least one hydrogen atom in the above-mentioned $C_{1-6}$ alkyl group is substituted with a cycloalkyl group having three to 10 carbon atoms, particularly more preferably a cyclopropyl $C_{1-6}$ alkyl group, a cyclohexyl $C_{1-6}$ alkyl group, a cyclooctyl $C_{1-6}$ alkyl group, or an adamantyl $C_{1-6}$ alkyl group, further preferably a cyclohexyl $C_{1-6}$ alkyl group or an adamantyl $C_{1-6}$ alkyl group.

$R_1$ of the compound (I) may be an unsubstituted cycloalkyl $C_{1-6}$ alkyl group or a cycloalkyl $C_{1-6}$ alkyl group that has a substituent. Examples of the substituent include the same substituents as the substituents mentioned above as the substituents of a "$C_{1-10}$ alkyl group."

More specifically, $R_1$ of the compound (I) is preferably a cyclohexylmethyl group or a 1-adamantanemethyl group.

The "heterocycloalkyl $C_{1-6}$ alkyl group" represented by $R_1$ means a group in which at least one hydrogen atom in the above-mentioned $C_{1-6}$ alkyl group is substituted with a heterocycloalkyl group. Examples of the heterocycloalkyl group include the same heterocycloalkyl groups as the functional groups mentioned as the "heterocycloalkyl groups" represented by $R_1$. $R_1$ of the compound (I) is preferably a tetrahydrofuryl $C_{1-6}$ alkyl group, a tetrahydropyranyl $C_{1-6}$ alkyl group, a piperidinyl $C_{1-6}$ alkyl group, a pyrrolidinyl $C_{1-6}$ alkyl group, a piperazinyl $C_{1-6}$ alkyl group, or a morpholinyl $C_{1-6}$ alkyl group, more preferably a tetrahydrofuryl $C_{1-6}$ alkyl group, a tetrahydropyranyl $C_{1-6}$ alkyl group, a piperidinyl $C_{1-6}$ alkyl group, or a pyrrolidinyl $C_{1-6}$ alkyl group.

$R_1$ of the compound (I) may be an unsubstituted heterocycloalkyl $C_{1-6}$ alkyl group or a heterocycloalkyl $C_{1-6}$ alkyl group that has a substituent. Examples of the substituent include the same substituents as the substituents mentioned above as the substituents of a "$C_{1-10}$ alkyl group." A substituent of a heterocycloalkyl $C_{1-6}$ alkyl group on $R_1$ is preferably an alkyl group or an arylalkyl group, more preferably an alkyl group or a phenyl $C_{1-6}$ alkyl group, further preferably a methyl group, an ethyl group, or a benzyl group.

More specifically, $R_1$ of the compound (I) is preferably a tetrahydrofuryl $C_{1-6}$ alkyl group, a tetrahydropyranyl $C_{1-6}$ alkyl group, a piperidinyl $C_{1-6}$ alkyl group, or a pyrrolidinyl $C_{1-6}$ alkyl group which may have an alkyl group or a phenyl $C_{1-6}$ alkyl group as a substituent, more preferably a 2-tetrahydrofurylmethyl group, a 3-tetrahydrofurylmethyl group, a 4-tetrahydropyranylmethyl group, a 2-(1-benzylpiperidin-4-yl)ethyl group, a 1-benzylpiperidin-4-yl group, a 2-(1,2,2,6,6-pentamethyl piperidin-4-yl)ethyl group, a 2-(piperidin-1-yl)ethyl group, or a (1-ethylpyrrolidin-2-yl)methyl group.

The "aryl $C_{1-6}$ alkyl group" represented by $R_1$ means a group in which at least one hydrogen atom in the above-mentioned $C_{1-6}$ alkyl group is substituted with an aryl group. Examples of the aryl group include the same aryl groups as the functional groups mentioned as the "aryl groups" represented by $R_1$. The aryl group is preferably a phenyl group or a naphthyl group, more preferably a phenyl group. Examples of the "aryl $C_{1-6}$ alkyl group" represented by $R_1$ include phenyl $C_{1-6}$ alkyl groups such as a benzyl group, a phenethyl group, a 1-phenylethyl group, a phenylpropyl group, and a phenylbutyl group and naphthyl $C_{1-6}$ alkyl groups such as a naphthylmethyl group, a naphthylethyl group, a naphthylpropyl group, and a naphthylbutyl group.

$R_1$ of the compound (I) may be an unsubstituted aryl $C_{1-6}$ alkyl group or an aryl $C_{1-6}$ alkyl group that has a substituent. Examples of the substituent include the same substituents as the substituents mentioned above as the substituents of a "$C_{1-10}$ alkyl group." A substituent of an aryl $C_{1-6}$ alkyl group on $R_1$ is preferably an alkyl group, an alkyloxy group, or a halogen atom, more preferably a methyl group, an isopropyl group, a methoxy group, an isopropoxy group, or a halogen atom.

More specifically, $R_1$ of the compound (I) is preferably a phenyl $C_{1-6}$ alkyl group or a naphthyl $C_{1-6}$ alkyl group which may have an alkyl group, an alkyloxy group, or a halogen atom as a substituent, more preferably a benzyl group, a phenethyl group, a 1-phenylethyl group, a 1-naphthylethyl group, a 4-methylbenzyl group, a 4-methylphenethyl group, a 2-methylphenethyl group, a 2,4-dimethylphenethyl group, a 1-(p-tolyl)ethyl group, a 2,4,6-trimethylbenzyl group, a 4-isopropylphenethyl group, a 3-methoxybenzyl group, a 4-methoxybenzyl group, a 4-methoxyphenethyl group, a 2-methoxyphenethyl group, a 1-(3-methoxyphenyl)ethyl group, a 4-isopropoxybenzyl group, a 2,4-dimethoxybenzyl group, a 4-chlorophenethyl group, or a 2,4-dichlorophenethyl group.

The "heteroaryl $C_{1-6}$ alkyl group" represented by $R_1$ means a group in which at least one hydrogen atom in the above-mentioned $C_{1-6}$ alkyl group is substituted with a heteroaryl group. Examples of the heteroaryl group include the same heteroaryl groups as the functional groups mentioned as the "heteroaryl groups" represented by $R_1$. The heteroaryl group is preferably a 5-membered ring or 6-membered ring. The "heteroaryl $C_{1-6}$ alkyl group" represented by $R_1$ is preferably a furyl $C_{1-6}$ alkyl group, a pyrrolyl $C_{1-6}$ alkyl group, a pyranyl $C_{1-6}$ alkyl group, a pyridyl $C_{1-6}$ alkyl group, an indolyl $C_{1-6}$ alkyl group, or a thienyl $C_{1-6}$ alkyl group, more preferably a furyl $C_{1-6}$ alkyl group, a pyridyl $C_{1-6}$ alkyl group, or a thienyl $C_{1-6}$ alkyl group.

$R_1$ of the compound (I) may be an unsubstituted heteroaryl $C_{1-6}$ alkyl group or a heteroaryl $C_{1-6}$ alkyl group that has a substituent. Examples of the substituent include the same substituents as the substituents mentioned above as the substituents of a "$C_{1-10}$ alkyl group."

More specifically, $R_1$ of the compound (I) is preferably a furfuryl group, a 2-thiophenemethyl group, a 2-pyridylmethyl group, a 4-pyridylmethyl group, a 2-(4-pyridyl)ethyl group, or a 2-(3-pyridyl)ethyl group.

The "$C_{1-6}$ alkenyl group" represented by $R_1$ means a straight or branched alkenyl group having one to six carbon atoms. Specific examples include a vinyl group, an allyl group, a propenyl group, a butenyl group, a 2-methylallyl group, an isopropenyl group, and a 2-methyl-1-propenyl group.

$R_1$ of the compound (I) may be an unsubstituted $C_{1-6}$ alkenyl group or a $C_{1-6}$ alkenyl group that has a substituent. Examples of the substituent include the same substituents as the substituents mentioned above as the substituents of a "$C_{1-10}$ alkyl group."

More specifically, $R_1$ of the compound (I) is preferably a 2-methylallyl group.

The "dihydrofuryl $C_{1-6}$ alkyl group" represented by $R_1$ means a group in which at least one hydrogen atom in the above-mentioned $C_{1-6}$ alkyl group is substituted with dihydrofuryl group.

$R_1$ of the compound (I) may be an unsubstituted dihydrofuryl $C_{1-6}$ alkyl group or a dihydrofuryl $C_{1-6}$ alkyl group that has a substituent. Examples of the substituent include the same substituents as the substituents mentioned above as the substituents of a "$C_{1-10}$ alkyl group." A substituent of a dihydrofuryl $C_{1-6}$ alkyl group on $R_1$ is preferably an alkyloxy group, more preferably a methoxy group.

More specifically, $R_1$ of the compound (I) is preferably a (2,5-dihydro-2,5-dimethoxyfuran-2-yl)methyl group.

In addition, $R_1$ of the compound (I) may be a tetrahydronaphthyl group or an indanyl group. Furthermore, these functional groups may be unsubstituted or have a substituent. Examples of the substituent include the same substituents as the substituents mentioned above as the substituents of a "$C_{1-10}$ alkyl group."

More specifically, for the compound (I), $R_1$ is preferably a 2-indanyl group or a 1,2,3,4-tetrahydronaphthalen-1-yl group.

Of these functional groups, $R_1$ of the compound (I) is preferably a methyl group, an ethyl group, an n-propyl group, an n-hexyl group, a 2-heptyl group, a 2-methylpropyl group, a 2,2-dimethylpropyl group, a 3,3-dimethylbutyl group, a 3-methoxypropyl group, a 1-methoxybutan-2-yl group, a 3-(dimethylamino)propyl group, a 2-(dimethylamino)ethyl group, a 3-dimethylamino-2,2-dimethylpropyl group, a 3-methylthiopropyl group, or a 2-(furfurylthio)ethyl group; a cyclohexyl group, a cyclopropyl group, a cyclooctyl group, or a 4-tert-butylcyclohexyl group; a cyclohexylmethyl group or a 1-adamantanemethyl group; a 2-tetrahydrofurylmethyl group, a 3-tetrahydrofurylmethyl group, a 4-tetrahydropyranylmethyl group, or a 2-(1-benzylpiperidin-4-yl)ethyl group; a 4-methylphenyl group, a 4-isopropylphenyl group, a 3,4-dimethylphenyl group, a 4-methoxyphenyl group, a 4-dimethylaminophenyl group, a 3,4-dimethoxyphenyl group, a 2,3-dihydro-1,4-benzodioxin-6-yl group, a 5-benzo[d][1,3]dioxolyl group, a 5-indanyl group, or a 2,3-dihydro-1-benzofuran-5-yl group; a benzyl group, a phenethyl group, a 1-phenylethyl group, a 4-isopropylphenethyl group, a 4-methylphenethyl group, a 4-methylbenzyl group, a 2-methylphenethyl group, a 2,4-dimethylphenethyl group, a 4-methoxybenzyl group, a 3-methoxybenzyl group, a 4-methoxyphenethyl group, a 2-methoxyphenethyl group, a 1-(p-tolyl)ethyl group, a 4-chlorophenethyl group, or a 2,4-dichlorophenethyl group; a furfuryl group, a 2-thiophenemethyl group, a 2-pyridylmethyl group, a 4-pyridylmethyl group, a 2-(4-pyridyl)ethyl group, or a 2-(3-pyridyl)ethyl group; a 1-benzylpiperidin-4-yl group; a 2-methylallyl group; a 1,2,3,4-tetrahydronaphthalen-1-yl group; a (2,5-dihydro-2,5-dimethoxyfuran-2-yl)methyl group; or a 2-indanyl group.

[About $R_2$]

$R_2$ represents a hydrogen atom, or a $C_{1-10}$ alkyl group, an aryl $C_{1-6}$ alkyl group, a cycloalkyl $C_{1-6}$ alkyl group, a heteroaryl $C_{1-6}$ alkyl group, a heterocycloalkyl $C_{1-6}$ alkyl group, an aryl group, or an acyl group which may have a substituent.

Examples of the "$C_{1-10}$ alkyl group" represented by $R_2$ include the same alkyl groups as the functional groups mentioned as the "$C_{1-10}$ alkyl groups" represented by $R_1$.

$R_2$ of the compound (I) may be an unsubstituted $C_{1-10}$ alkyl group or a $C_{1-10}$ alkyl group that has a substituent. Examples of the substituent include the same substituents as the substituents mentioned as the substituents of a "$C_{1-10}$ alkyl group" represented by $R_1$.

$R_2$ of the compound (I) is particularly preferably a 3,3-dimethylbutyl group.

Examples of the "aryl $C_{1-6}$ alkyl group" represented by $R_2$ include the same aryl $C_{1-6}$ alkyl groups as the functional groups mentioned as the "aryl $C_{1-6}$ alkyl groups" represented by $R_1$. The "aryl $C_{1-6}$ alkyl group" represented by $R_2$ is preferably a phenyl $C_{1-6}$ alkyl group or a naphthyl $C_{1-6}$ alkyl group.

$R_2$ of the compound (I) may be an unsubstituted aryl $C_{1-6}$ alkyl group or an aryl $C_{1-6}$ alkyl group that has a substituent. Examples of the substituent include the same substituents as the substituents mentioned as the substituents of a "$C_{1-10}$ alkyl group" represented by $R_1$. Furthermore, $R_2$ of the compound (I) may be an aryl $C_{1-6}$ alkyl group that has one substituent in an aryl group or an aryl $C_{1-6}$ alkyl group that has two or more substituents. When an aryl $C_{1-6}$ alkyl group has two or more substituents, the two or more substituents may be the same substituents or a combination of different substituents. Furthermore, when an aryl $C_{1-6}$ alkyl group has two or more substituents, the two or more substituents may be joined together with each other to form a ring.

A substituent of an aryl $C_{1-6}$ alkyl group on $R_2$ is preferably an alkyloxy group, a fluoroalkyl group, an alkylamino group, a dialkylamino group, an acyl group, a hydroxy group, an aryloxy group, or a halogen atom, more preferably a methoxy group, a 3-dimethylaminopropoxy group, a phenoxy group, a trifluoromethyl group, a dimethylamino group, a 4-methoxycarbonyl group, a hydroxy group, or a halogen atom. In addition, a benzodioxolyl group (piperonyl group) in which an alkyloxy group and a hydroxy group form a ring is also preferred.

More specifically, $R_2$ of the compound (I) is preferably a phenyl $C_{1-6}$ alkyl group or a naphthyl $C_{1-6}$ alkyl group which may have a substituent selected from the group consisting of an alkyloxy group, a fluoroalkyl group, an alkylamino group, a dialkylamino group, an acyl group, a hydroxy group, an aryloxy group, and a halogen atom (a phenyl $C_{1-6}$ alkyl group or a naphthyl $C_{1-6}$ alkyl group may have two or more of these substituents, and two or more substituents may be joined together to form a ring), more preferably a benzyl group, a phenethyl group, a 3-phenylpropyl group, a 1-naphthylmethyl group, a 2-naphthylmethyl group, a 4-methoxybenzyl group, a 6-methoxy-2-naphthylmethyl group, a 4-trifluoromethylbenzyl group, a 4-dimethylaminobenzyl group, a 4-dimethylamino-3-methoxybenzyl group, a 4-dimethylamino-2-naphthylmethyl group, a 4-methoxycarbonylbenzyl group, a 3-hydroxybenzyl group, a 2-hydroxybenzyl group, a 4-hydroxybenzyl group, a 4-hydroxy-3-methoxybenzyl group, a 3-hydroxy-4-methoxybenzyl group, a 3,5-dimethoxy-4-hydroxybenzyl group, a 3-phenoxybenzyl group, a 4-phenoxybenzyl group, a 4-(3-dimethylaminopropoxy)benzyl group, a 4-chlorobenzyl group, a 3-chloro-4-hydroxybenzyl group, or a benzo[1,3]dioxol-5-ylmethyl group, further preferably a benzyl group, a 3-hydroxybenzyl group, a 2-hydroxybenzyl group, a 4-hydroxybenzyl group, a 4-hydroxy-3-methoxybenzyl group, or a phenethyl group.

Examples of the "heteroaryl $C_{1-6}$ alkyl group" represented by $R_2$ include the same heteroaryl $C_{1-6}$ alkyl groups as the functional groups mentioned as the "heteroaryl $C_{1-6}$ alkyl groups" represented by $R_1$. The "heteroaryl $C_{1-6}$ alkyl group" represented by $R_2$ is preferably a pyridyl $C_{1-6}$ alkyl group, a furyl $C_{1-6}$ alkyl group, a pyrrolyl $C_{1-6}$ alkyl group, a quinolyl $C_{1-6}$ alkyl group, or an indolyl $C_{1-6}$ alkyl group, preferably a pyridyl $C_{1-6}$ alkyl group, an indolyl $C_{1-6}$ alkyl group, or a pyrrolyl $C_{1-6}$ alkyl group.

$R_2$ of the compound (I) may be an unsubstituted heteroaryl $C_{1-6}$ alkyl group or a heteroaryl $C_{1-6}$ alkyl group that has a substituent. Examples of the substituent include the same substituents as the substituents mentioned as the substituents of a "$C_{1-10}$ alkyl group" represented by $R_1$. A substituent of a heteroaryl $C_{1-6}$ alkyl group on $R_2$ is preferably an arylalkyl group or an alkyl group, more preferably a phenyl $C_{1-6}$ alkyl group or an alkyl group, further preferably a benzyl group or a methyl group.

More specifically, $R_2$ of the compound (I) is preferably a pyridyl $C_{1-6}$ alkyl group, a furyl $C_{1-6}$ alkyl group, a pyrrolyl $C_{1-6}$ alkyl group, a quinolyl $C_{1-6}$ alkyl group, or an indolyl $C_{1-6}$ alkyl group which may have a phenyl $C_{1-6}$ alkyl group or an alkyl group as a substituent, more preferably a 4-pyridylmethyl group, a 3-pyridylmethyl group, a 2-pyridylmethyl group, a 2-furylmethyl group, a (pyrrol-2-yl)methyl group, a quinolin-5-ylmethyl group, a quinolin-2-ylmethyl group, a quinolin-8-ylmethyl group, a 1-benzylindol-3-ylmethyl group, a 1-methylindol-3-ylmethyl group, an indol-3-ylmethyl group, or an indol-6-ylmethyl group, further preferably a 4-pyridylmethyl group, a 3-pyridylmethyl group, a 2-pyridylmethyl group, an indol-3-ylmethyl group, or a (pyrrol-2-yl)methyl group.

Examples of the "cycloalkyl $C_{1-6}$ alkyl group" represented by $R_2$ include the same cycloalkyl $C_{1-6}$ alkyl group as the functional groups mentioned as the "cycloalkyl $C_{1-6}$ alkyl groups" represented by $R_1$.

The "cycloalkyl $C_{1-6}$ alkyl group" represented by $R_2$ is preferably a cyclohexyl $C_{1-6}$ alkyl group.

$R_2$ of the compound (I) may be an unsubstituted cycloalkyl $C_{1-6}$ alkyl group or a cycloalkyl $C_{1-6}$ alkyl group that has a substituent. Examples of the substituent include the same substituents as the substituents mentioned as the substituents of a "$C_{1-10}$ alkyl group" represented by $R_1$.

More specifically, $R_2$ of the compound (I) is preferably a cyclohexylethyl group or a cyclohexylmethyl group.

Examples of the "heterocycloalkyl $C_{1-6}$ alkyl group" represented by $R_2$ include the same heterocycloalkyl $C_{1-6}$ alkyl groups as the functional groups mentioned as the "heterocycloalkyl $C_{1-6}$ alkyl groups" represented by $R_1$. The "heterocycloalkyl $C_{1-6}$ alkyl group" represented by $R_2$ is preferably a tetrahydrofuryl $C_{1-6}$ alkyl group.

$R_2$ of the compound (I) may be an unsubstituted heterocycloalkyl $C_{1-6}$ alkyl group or a heterocycloalkyl $C_{1-6}$ alkyl group that has a substituent. Examples of the substituent include the same substituents as the substituents mentioned as the substituents of a "$C_{1-10}$ alkyl group" represented by $R_1$.

More specifically, $R_2$ of the compound (I) is preferably a 3-tetrahydrofurylmethyl group or a 3-tetrahydrofuryl ethyl group, more preferably a 3-tetrahydrofurylmethyl group.

Examples of the "aryl group" represented by $R_2$ include the same aryl groups as the functional groups mentioned as the "aryl groups" represented by $R_1$.

$R_2$ of the compound (I) may be an unsubstituted aryl group or an aryl group that has a substituent. Examples of the substituent include the same substituents as the substituents mentioned as the substituents of a "$C_{1-10}$ alkyl group" represented by More specifically, $R_2$ of the compound (I) is preferably a phenyl group which may have a substituent, more preferably an unsubstituted phenyl group.

Examples of the "acyl group" represented by $R_2$ include a formyl group, an acetyl group, a propionyl group, a butyryl group, an isobutyryl group, a varelyl group, an isovarelyl group, a pivaloyl group, a hexanoyl group, a benzoyl group, an aroyl group, and a nicotinoyl group.

$R_2$ of the compound (I) may be an unsubstituted acyl group or an acyl group that has a substituent. Examples of the substituent include the same substituents as the substituents mentioned as the substituents of a "$C_{1-10}$ alkyl group" represented by $R_1$.

More specifically, $R_2$ of the compound (I) is preferably a benzoyl group which may have a substituent, more preferably an unsubstituted benzoyl group.

Of these functional groups, for the compound (I), $R_2$ is preferably a 3,3-dimethylbutyl group; a benzyl group, a 3-hydroxybenzyl group, a 2-hydroxybenzyl group, a 4-hydroxybenzyl group, a 4-hydroxy-3-methoxybenzyl group, or a phenethyl group; a 4-pyridylmethyl group, a 3-pyridylmethyl group, a 2-pyridylmethyl group, an indol-3-ylmethyl group, or a (pyrrol-2-yl)methyl group; or a cyclohexylmethyl group.

[About $R_3$]

$R_3$ each independently represents a hydrogen atom, or a $C_{1-10}$ alkyl group or a dialkylaminocarbonyl group which may have a substituent.

Examples of the "$C_{1-10}$ alkyl group" represented by $R_3$ include the same alkyl groups as the functional groups mentioned as the "$C_{1-10}$ alkyl groups" represented by $R_1$.

$R_3$ of the compound (I) may be an unsubstituted $C_{1-10}$ alkyl group or a $C_{1-10}$ alkyl group that has a substituent. Examples of the substituent include the same substituents as the substituents mentioned as the substituents of a "$C_{1-10}$ alkyl group" represented by $R_1$.

$R_3$ of the compound (I) is particularly a methyl group or an ethyl group, more preferably a methyl group.

Examples of the "dialkylaminocarbonyl group" represented by $R_3$ include di$C_{1-6}$ alkylaminocarbonyl groups such as a dimethylaminocarbonyl group, a diethylaminocarbonyl group, and a di-n-propylaminocarbonyl group.

$R_3$ of the compound (I) is particularly preferably a di-n-propylaminocarbonyl group.

Of these functional groups, for the compound (I), $R_3$ is preferably each independently a hydrogen atom, a methyl group, or a di-n-propylaminocarbonyl group, and $R_3$ is more preferably each independently a hydrogen atom or a methyl group. Of these groups, further preferably, both the two $R_3$ groups are a hydrogen atom, or one $R_3$ group is a hydrogen atom, and the other $R_3$ group is a methyl group.

[About $R_4$]

$R_4$ each independently represents a hydrogen atom, or a $C_{1-10}$ alkyl group which may have a substituent.

Examples of the "$C_{1-10}$ alkyl group" represented by $R_4$ include the same alkyl groups as the functional groups mentioned as the "$C_{1-10}$ alkyl groups" represented by $R_1$. The "$C_{1-10}$ alkyl group" represented by $R_4$ is preferably a methyl group or an ethyl group.

$R_4$ of the compound (I) may be an unsubstituted $C_{1-10}$ alkyl group or a $C_{1-10}$ alkyl group that has a substituent. In addition to the same substituents as the substituents mentioned as the substituents of a "$C_{1-10}$ alkyl group" represented by $R_1$, examples of the substituent include amide groups such as a dialkylaminocarbonyl group and an alkylcarbonylamino group. A substituent of a $C_{1-10}$ alkyl group on $R_4$ is preferably a dialkylaminocarbonyl group or an alkylcarbonylamino group, more preferably a di-n-propylaminocarbonyl group or a 2-acetamide group.

More specifically, examples of the $C_{1-10}$ alkyl group that has a substituent include a diethylaminocarbonylmethyl group, a di-n-propylaminocarbonylmethyl group, a 2-acetamideethyl group, and a 2-acetamide methyl group.

Of these functional groups, preferably, for the compound (I), both the two $R_4$ groups are a hydrogen atom or a methyl group, or one $R_4$ group is a hydrogen atom, and the other $R_4$ group is a methyl group, a 2-acetamideethyl group, or a di-n-propylaminocarbonylmethyl group.

[About $R_5$]

$R_5$ represents a hydrogen atom, or a $C_{1-6}$ alkyl group which may have a substituent. Of these groups, $R_6$ is particularly preferably a hydrogen atom or an unsubstituted methyl group.

Examples of the "$C_{1-6}$ alkyl group" represented by $R_5$ include the same alkyl groups as the functional groups mentioned as the $C_{1-6}$ alkyl groups represented by $R_1$. The "$C_{1-6}$ alkyl group" represented by $R_5$ is particularly preferably a methyl group or an ethyl group.

$R_5$ of the compound (I) may be an unsubstituted $C_{1-6}$ alkyl group or a $C_{1-6}$ alkyl group that has a substituent. In addition to the same substituents as the substituents mentioned as the substituents of a $C_{1-10}$ alkyl group represented by $R_1$, examples of the substituent include amide groups such as a dialkylaminocarbonyl group and an alkylcarbonylamino group.

More specifically, examples of the $C_{1-6}$ alkyl group that has a substituent include a diethylaminocarbonylmethyl group, a di-n-propylaminocarbonylmethyl group, a 2-acetamideethyl group, and a 2-acetamide methyl group.

Groups for $R_1$, $R_2$, $R_3$, $R_4$, and $R_5$ in the compound (I) can each independently be selected from the functional groups mentioned above, and it is needless to say that combinations thereof are not limited.

The most preferred aspects of the compound according to the present invention include the compounds listed below or a salt thereof or a solvate of the compound or a salt thereof. However, it is needless to say that the scope of the present invention is not limited thereto. (1) 1-benzylindolin-5-yl 4-isopropyl phenyl carbamate, (2) 1-phenethyl indolin-5-yl 4-isopropyl phenyl carbamate, (3) 1-(3,3-dimethyl butyl)indolin-5-yl 4-isopropyl phenyl carbamate, (4) 1-benzylindolin-5-yl 4-methoxyphenyl carbamate, (5) 1-benzylindolin-5-yl 2,3-dihydro-1,4-benzodioxin-6-yl carbamate, (6) 1-benzylindolin-5-yl 5-benzo[d][1,3]dioxolyl carbamate, (7) 1-benzylindolin-5-yl 2,3-dihydro-1-benzofuran-5-yl carbamate, (8) 1-benzylindolin-5-yl benzylcarbamate, (9) 1-benzylindolin-5-yl phenethyl carbamate, (10) 1-benzylindolin-5-yl n-hexyl carbamate, (11) 1-benzylindolin-5-yl furfuryl carbamate, (12) 1-benzylindolin-5-yl (S)-1-phenyl ethyl carbamate, (13) 1-benzylindolin-5-yl cyclohexyl carbamate, (14) 1-(4-pyridyl methyl)indolin-5-yl 4-isopropyl phenyl carbamate, (15) 1-(3-pyridyl methyl)indolin-5-yl 4-isopropyl phenyl carbamate, (16) 1-benzylindolin-5-yl 4-methoxybenzylcarbamate, (17) 1-benzylindolin-5-yl 4-methoxyphenethyl carbamate, (18) 1-benzylindolin-5-yl 4-isopropyl phenethyl carbamate, (19) 1-benzylindolin-5-yl cyclohexyl methyl carbamate, (20) 1-benzylindolin-5-yl 2-methyl propyl carbamate, (21) 1-benzylindolin-5-yl cyclopropyl carbamate, (22) 1-benzylindolin-5-yl 3,3-dimethyl butyl carbamate, (23) 1-benzylindolin-5-yl 4-tert-butyl cyclohexyl carbamate, (24) 1-benzylindolin-5-yl 2-indanyl carbamate, (25) 1-benzylindolin-5-yl cyclooctyl carbamate, (26) 1-benzylindolin-5-yl 1-methoxybutan-2-yl carbamate, (27) 1-benzylindolin-5-yl 1-adamantane methyl carbamate, (28) 1-benzylindolin-5-yl 3-methyl thiopropyl carbamate, (29) 1-benzylindolin-5-yl 2-heptyl carbamate, (30) 1-benzylindolin-5-yl 2-tetrahydrofuryl methyl carbamate, (31) 1-benzylindolin-5-yl 2-methyl allyl carbamate, (32) 1-benzylindolin-5-yl 2-(furfuryl thio)ethyl carbamate, (33) 1-benzylindolin-5-yl 4-methyl phenyl carbamate, (34) 1-benzylindolin-5-yl ethyl carbamate, (35) 1-(2-pyridyl methyl)indolin-5-yl 4-isopropyl phenyl carbamate, (36) 1-(3-hydroxybenzyl)indolin-5-yl 4-isopropyl phenyl carbamate, (37) 1-[(pyrrol-2-yl)methyl]indolin-5-yl 4-isopropyl phenyl carbamate, (38) 1-(2-hydroxybenzyl)indolin-5-yl 4-isopropyl phenyl carbamate, (39) 1-(4-hydroxy-3-methoxybenzyl)indolin-5-yl 4-isopropyl phenyl carbamate, (40) 1-(cyclohexylmethyl)indolin-5-yl 4-isopropyl phenyl carbamate, (41) 1-(4-hydroxybenzyl)indolin-5-yl 4-isopropyl phenyl carbamate, (42) 1-(indol-3-yl methyl)indolin-5-yl 4-isopropyl phenyl carbamate, (43) 1-benzylindolin-5-yl 5-indanyl carbamate, (44) 1-benzylindolin-5-yl 4-methyl phenethyl carbamate, (45) 1-benzylindolin-5-yl 1,2,3,4-tetrahydronaphthalen-1-yl carbamate, (46) 1-benzylindolin-5-yl 1-(p-tolyl)ethyl carbamate, (47) 1-benzylindolin-5-yl 2-thiophene methyl carbamate, (48) 1-benzylindolin-5-yl 4-methyl benzylcarbamate, (49) 1-benzylindolin-5-yl 3-methoxybenzylcarbamate, (50) 1-benzylindolin-5-yl 2-pyridyl methyl carbamate, (51) 1-benzylindolin-5-yl 4-pyridyl methyl carbamate, (52) 1-benzylindolin-5-yl 4-chlorophenethyl carbamate, (53) 1-benzylindolin-5-yl 3,4-dimethyl phenyl carbamate, (54) 1-benzylindolin-5-yl n-propyl carbamate, (55) 1-benzylindolin-5-yl 2-methyl phenethyl carbamate, (56) 1-benzylindolin-5-yl 2,4-dimethyl phenethyl carbamate, (57) 1-benzylindolin-5-yl 2-methoxyphenethyl carbamate, (58) 1-benzylindolin-5-yl 2,4-dichlorophenethyl carbamate, (59) 1-benzylindolin-5-yl 2-(4-pyridyl)ethyl carbamate, (60) 1-benzylindolin-5-yl 2-(3-pyridyl)ethyl carbamate, (61) 1-benzylindolin-5-yl (2,5-dihydro-2,5-dimethoxyfuran-2-yl)methyl carbamate, (62) indolin-5-yl benzylcarbamate, (63) 1-benzylindolin-5-yl methyl carbamate, (64) 1-benzylindolin-5-yl 4-dimethyl aminophenyl carbamate, (65) 1-benzylindolin-5-yl 3-(dimethylamino)propyl carbamate, (66) 1-benzylindolin-5-yl 1-benzylpiperidin-4-yl carbamate, (67) 1-benzylindolin-5-yl 2-(1-benzylpiperidin-4-yl)ethyl carbamate, (68) 1-benzylindolin-5-yl 3,4-dimethoxyphenyl carbamate, (69) 1-benzyl-3,3-dimethyl indolin-5-yl 4-isopropyl phenyl carbamate, (70) 1-benzyl-3-methylindolin-5-yl 4-isopropyl phenyl carbamate, (71) 1-(2-pyridyl methyl)indolin-5-yl n-hexyl carbamate, (72) 1-(2-pyridyl methyl)indolin-5-yl cyclohexyl methyl carbamate, (73) 1-(2-pyridyl methyl)indolin-5-yl cyclohexyl carbamate, (74) 1-(2-pyridyl methyl)indolin-5-yl benzylcarbamate, (75) 1-(2-pyridyl methyl)indolin-5-yl 4-dimethyl aminophenyl carbamate, (76) 1-(2-pyridyl methyl)indolin-5-yl 2,2-dimethyl propyl carbamate, (77) 1-benzylindolin-5-yl 3-tetrahydrofuryl methyl carbamate, (78) 1-benzylindolin-5-yl 3-dimethylamino-2,2-dimethyl propyl carbamate, (79) 3-(2-acetamide ethyl)-1-benzylindolin-5-yl 4-isopropyl phenyl carbamate, (80) 1-benzyl-3-(di-n-propyl aminocarbonyl methyl)indolin-5-yl 4-isopropyl phenyl carbamate, (81) 1-benzyl-3-(di-n-propyl aminocarbonyl methyl)-2-methylindolin-5-yl 4-isopropyl phenyl carbamate, (82) O-(1-benzylindolin-5-yl)-N-(cyclohexylmethyl)-N-methyl carbamate, (83) O-(1-benzyl-3,3-dimethyl indolin-5-yl)-N-(cyclohexylmethyl)-N-methyl carbamate, (84) O-(1-benzyl-3,3-dimethyl indolin-5-yl)-N-methyl-N-(4-tetrahydropyranyl methyl)carbamate, (85) N-methyl-O-[1-(2-pyridyl methyl)-3,3-dimethyl indolin-5-yl]-N-(4-tetrahydropyranyl methyl)carbamate, (86) N-methyl-O-[1-(3-pyridyl methyl)-3,3-dimethyl indolin-5-yl]-N-(4-tetrahydropyranyl methyl)carbamate, and (87) N-methyl-O-[1-(4-pyridyl methyl)-3,3-dimethyl indolin-5-yl]-N-(4-tetrahydropyranyl methyl)carbamate.

Furthermore, the "pharmacologically acceptable salt" in the present invention is not particularly limited so long as the salt forms an addition salt and the compound according to the present invention. Examples of the "pharmacologically acceptable salt" include hydrohalides such as hydrofluorides, hydrochlorides, hydrobromides, and hydroiodides; inorganic acid salts such as sulfates, nitrates, perchlorates, phosphates, carbonates, and bicarbonates; organic carboxylic acid salts such as acetates, oxalates, maleates, tartarates, and fumarates; organic sulfonic acid salts such as methanesulfonates, trifluoromethanesulfonates, ethanesulfonates, benzenesulfonates, toluenesulfonate, and camphorsulfonates; amino acid salts such as aspartates and glutamates; salts with an amine such as trimethylamine salts, triethylamine salts, procaine salts, pyridine salts, and phenethylbenzylamine salts; alkali metal salts such as sodium salts and potassium salts; and alkaline earth metal salts such as magnesium salts and calcium salts. Of these salts, hydrochlorides and oxalates are preferred.

A representative method for producing the compound (I) according to the present invention and intermediates thereof will be described below.

<Common Production Method 1>

This process is a method for producing a compound (IV)', a synthesis intermediate of the compound (I) according to the present invention, from a compound (II) via two steps, [Step 1-1a] and [Step 1-1b] or [Step 1-2a] and [Step 1-2b].

this reaction is not particularly limited so long as the solvent does not inhibit the reaction. Examples of the solvent include methanol and ethanol.

The reaction time is not particularly limited and is usually 0.1 to 48 hours for any reaction, preferably 0.5 to 24 hours.

The reaction temperature is usually −78° C. to 150° C. for any reaction, more preferably 0° C. to room temperature.

[Step 1-1b]

This step is a step of obtaining a compound (IV)' by a reaction represented by a reductive amination reaction with an aldehyde compound ($R_2$'CHO, $R_2$'$CH_2$=$R_2$) or an N-alkylation reaction with a halide compound ($R_2$—X). This step is not limited to these reactions, and the compound (IV)' may be obtained using any compound that can be reacted with the compound (IIIa).

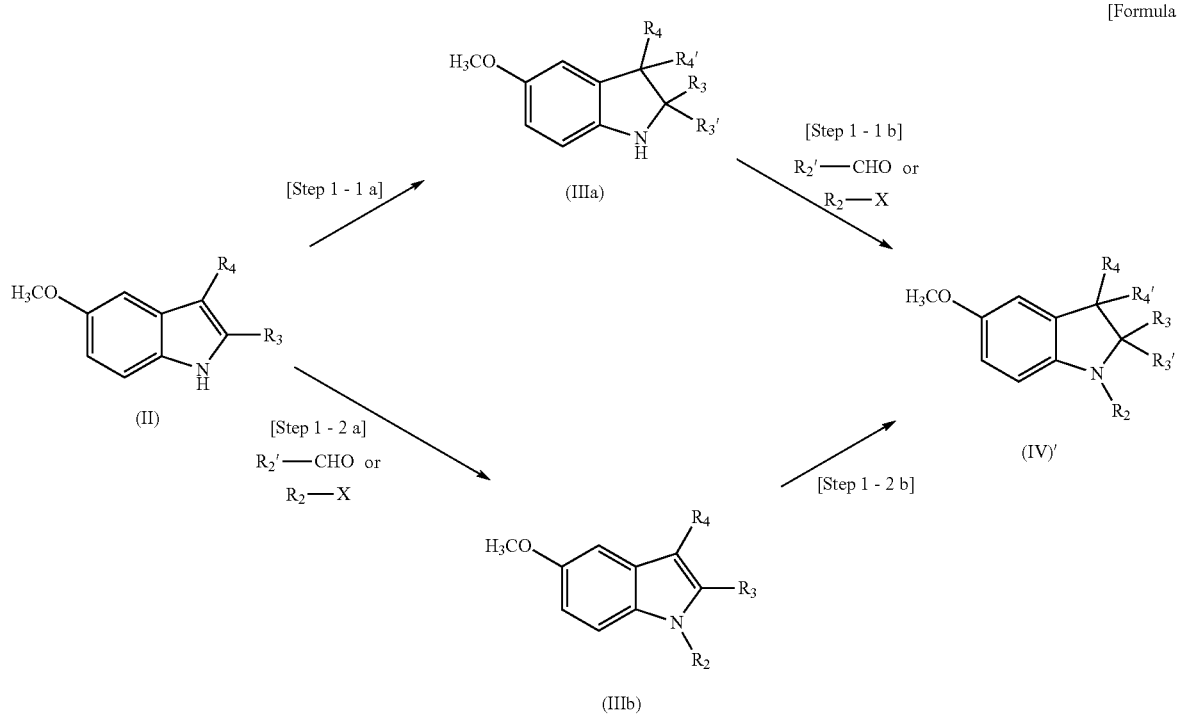

[Formula 7]

wherein $R_2$, $R_3$, and $R_4$ have the same meaning as defined above, and $R_3$' and $R_4$' represent a hydrogen atom.

[Step 1-1a]

This step is a step of obtaining a compound (IIIa) by a reduction reaction of a compound (II) with sodium borohydride, sodium cyanoborohydride, or sodium triacetoxyhydroborate, a reduction reaction with metal magnesium, or the like.

The solvent used in the reduction reaction with sodium borohydride, sodium cyanoborohydride, or sodium triacetoxyhydroborate is not particularly limited so long as the solvent does not inhibit the reaction. Examples of the solvent include acidic solvents such as acetic acid and trifluoroacetic acid. In addition, the solvent may be a mixed solvent with other solvents.

Furthermore, the compound (IIIa) can also be obtained by a reduction reaction with magnesium instead of a reduction reaction with sodium borohydride, sodium cyanoborohydride, or sodium triacetoxyhydroborate. The solvent used in In a reductive amination reaction with an aldehyde compound ($R_2$'CHO, $R_2$'$CH_2$=$R_2$), sodium borohydride, sodium cyanoborohydride, or sodium triacetoxyhydroborate is used as a reducing agent. The solvent used in this reaction is not particularly limited so long as the solvent does not inhibit the reaction. Examples of the solvent include acidic solvents such as acetic acid and trifluoroacetic acid. In addition, the solvent may be a mixed solvent with other solvents.

In an N-alkylation reaction with a halide compound ($R_2$—X), an organic base such as a triethylamine and N,N-diisopropylethylamine or an inorganic base such as sodium hydride and potassium carbonate is used as a base. The solvent used in this reaction is not particularly limited so long as the solvent does not inhibit the reaction. Examples of the solvent include acetonitrile and N,N-dimethylformamide.

The reaction time is not particularly limited and is usually 0.1 to 48 hours for any reaction, preferably 0.5 to 24 hours.

The reaction temperature is usually −78° C. to 150° C. for any reaction, more preferably 0° C. to room temperature.

The synthesis intermediate compound (IV)' can also be produced from the compound (II) via [Step 1-2a] and [Step 1-2b]. In this case, [Step 1-2a] can be performed under the same conditions as for [Step 1-1b]. [Step 1-2b] can be performed under the same conditions as for [Step 1-1a].

Both the production method by two steps [Step 1-1a] and [Step 1-1b] and the production method by two steps [Step 1-2a] and [Step 1-2b] can also be performed in one pot by adding reagents for the second step to the same pot after the reaction of the first step.

<Common Production Method 2>

This process is a method for producing the compound (I-1) according to the present invention via [Step 2-1] and [Step 2-2] from the compound (IV)' synthesized in Common Production Method 1 or a compound (IV) synthesized by another production method.

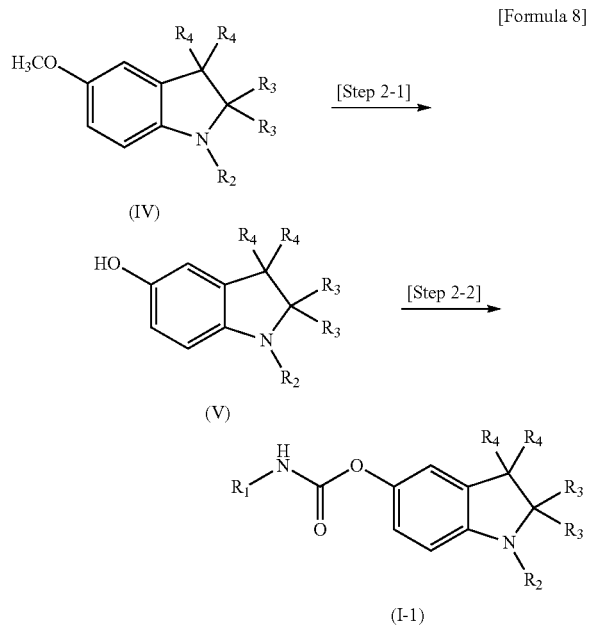

[Formula 8]

wherein $R_1$, $R_2$, $R_3$, and $R_4$ have the same meaning as defined above.

[Step 2-1]

This step is a step for obtaining a corresponding phenol compound (V) by reacting a compound (IV) (including compound (IV)') with $BBr_3$, $AlCl_3$, hydrobromic acid-acetic acid, or the like to eliminate a methyl group of a methoxy group.

This reaction can be performed under conditions generally used for demethylation of a methoxy group on an aromatic ring, such as, for example, a condition similar to the condition described in the literature (T. W. Green and P. G. M. Wuts, "Protective Groups in Organic Chemistry, Third Edition," John Wiley & Sons, 1999, 250-7).

The solvent used in this reaction is not particularly limited so long as the solvent does not inhibit the reaction. Examples of the solvent include dichloromethane and 1,2-dichloroethane.

The reaction time is not particularly limited and is usually 0.1 to 48 hours, preferably 0.1 to six hours.

The reaction temperature is usually −78° C. to 150° C., more preferably 0° C. to room temperature.

[Step 2-2]

This step is a step of obtaining a compound (I-1) by a reaction of reacting a phenol compound (V) and an isocyanate compound ($R_1$—NCO) in the presence of metal sodium, sodium hydride, or the like or by a reaction of reacting an amine compound ($R_1$—$NH_2$) and triphosgene in the presence of a base.

The solvent used in the reaction of reacting a phenol compound (V) and an isocyanate compound ($R_1$—NCO) in the presence of metal sodium, sodium hydride, or the like is not particularly limited so long as the solvent does not inhibit the reaction. Examples of the solvent include diethyl ether, tetrahydrofuran, and mixed solvents thereof.

The solvent used in the reaction of reacting an amine compound ($R_1$—$NH_2$) and a triphosgene in the presence of a base is not particularly limited so long as the solvent does not inhibit the reaction. Examples of the solvent include methylene chloride and tetrahydrofuran. Examples of the base used in the reaction include organic bases such as triethylamine and N,N-diisopropylethylamine.

The reaction time is not particularly limited and is usually one minute to 48 hours for any reaction, preferably five minutes to three hours.

The reaction temperature is usually −78° C. to 150° C. for any reaction, more preferably 0° C. to room temperature.

<Common Production Method 3>

This process is a process of obtaining the compound (I-2) according to the present invention by a contact reduction to debenzylate a compound (I-1)' in which $R_2$ is a benzyl group.

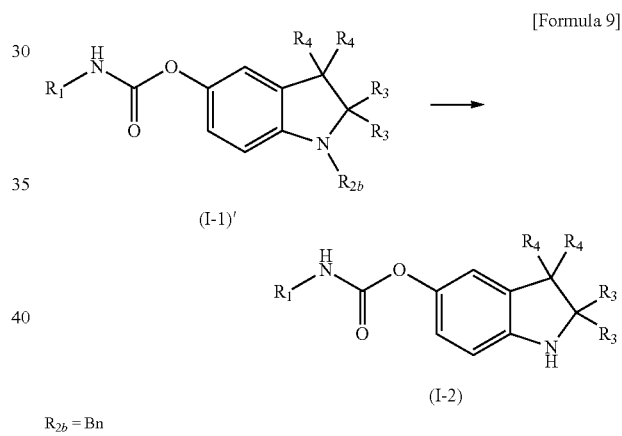

[Formula 9]

$R_{2b} = Bn$ wherein $R_{2b}$ represents Bn, and $R_1$, $R_3$, and $R_4$ have the same meaning as defined above.

This reaction can be performed under the same conditions as conditions usually used for debenzylation such as, for example, a condition similar to the condition described in the literature (T. W. Green and P. G. M. Wuts, "Protective Groups in Organic Chemistry, Third Edition," John Wiley & Sons, 1999, 579-81) under hydrogen atmosphere.

The solvent used in the reaction is not particularly limited so long as the solvent does not inhibit the reaction. Examples of the solvent include methanol, ethanol, isopropanol, tetrahydrofuran, 1,4-dioxane, and ethyl acetate. An acidic solvent such as hydrochloric acid may be used as a cosolvent.

Examples of the metal catalyst used in the reaction include palladium-carbon, palladium hydroxide-carbon, platinum oxide, and Raney nickel.

The reaction condition is not particularly limited. The reaction can be performed at room temperature to the reflux temperature of the solvent under normal pressure to 150 atmospheres, preferably at room temperature to 40° C. under normal pressure.

<Common Production Method 4>

This process is a method for producing the compound (I) according to the present invention from a compound (I-2).

[Formula 10]

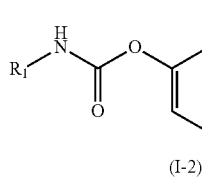
(I-2)

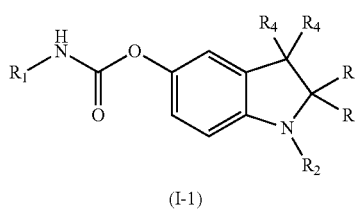
(I-1)

wherein $R_1$, $R_2$, $R_3$, and $R_4$ have the same meaning as defined above.

This step is a step of obtaining a compound (I-1) by a reaction represented by a reductive amination reaction with an aldehyde compound ($R_2'CHO$, $R_2'CH_2{=}R_2$) or an N-alkylation reaction with a halide compound ($R_2$—X). This step is not limited to these reactions, and a compound (I-1) may be obtained by using any compound that can be reacted with the compound (I-2).

In the reductive amination reaction with an aldehyde compound ($R_2'CHO$, ${=}R_2$), sodium borohydride, sodium cyanoborohydride, or sodium triacetoxyhydroborate is used as a reducing agent. The solvent used in this reaction is not particularly limited so long as the solvent does not inhibit the reaction. Examples of the solvent include acidic solvents such as acetic acid and trifluoroacetic acid. In addition, the reaction may be performed with a mixed solvent with other solvents.

In the N-alkylation reaction with a halide compound ($R_2$—X), an organic base such as triethylamine and N,N-diisopropylethylamine or an inorganic base such as sodium hydride and potassium carbonate is used as a base. The solvent used in this reaction is not particularly limited so long as the solvent does not inhibit the reaction. Examples of the solvent include acetonitrile and N,N-dimethylformamide.

The reaction time is not particularly limited and is usually 0.1 to 48 hours for any reaction, preferably 0.5 to 24 hours.

The reaction temperature is usually −78° C. to 150° C. for any reaction, more preferably 0° C. to room temperature.

<Common Production Method 5>

This process is a method for producing the compound (I-3) according to the present invention from the above-mentioned phenol compound (V). The compound (I-3) can be obtained by converting a phenol compound (V) to an intermediate (VI) having a leaving group X and then reacting the intermediate with an N-methylamine compound (VII, $R_1$-(Me)NH) in the presence of a base.

[Formula 11]

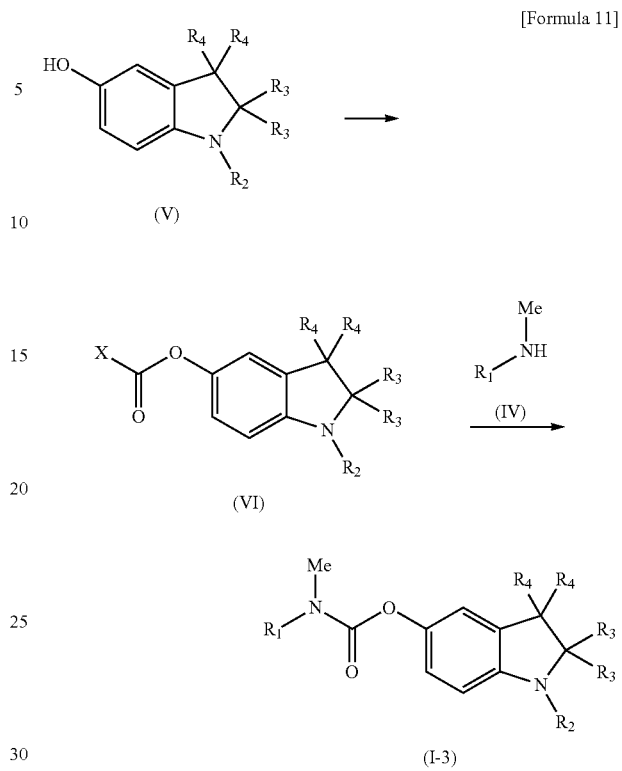

wherein $R_1$, $R_2$, $R_3$, and $R_4$ have the same meaning as defined above.

Conversion to the intermediate (VI) having a leaving group X can be performed by, for example, allowing 4-nitrophenyl (X=4-nitrophenyl)chloroformate or triphosgene (X=Cl) to act on the phenol compound (V) in the presence of a base. The solvent used in the reaction is not particularly limited so long as the solvent does not inhibit the reaction. Examples of the solvent include methylene chloride and tetrahydrofuran. Examples of the base used in the reaction include organic bases such as triethylamine and N,N-diisopropylethylamine.

The solvent used in the reaction of reacting the intermediate (VI) having a leaving group X and the N-methylamine compound (VII, $R_1$-(Me)NH) in the presence of a base is not particularly limited so long as the solvent does not inhibit the reaction. Examples of the solvent include methylene chloride and tetrahydrofuran. Examples of the base used in the reaction include organic bases such as triethylamine and N,N-diisopropylethylamine.

The reaction time is not particularly limited and is usually one minute to 48 hours for any reaction, preferably five minutes to three hours.

The reaction temperature is usually −78° C. to 150° C. for any reaction, more preferably 0° C. to room temperature.

<Common Production Method 6>

Furthermore, the compound (I-3) can also be obtained by reacting a commercially available or separately prepared intermediate (VIII) having a leaving group X with a phenol compound (V) in the presence of a base.

[Formula 12]

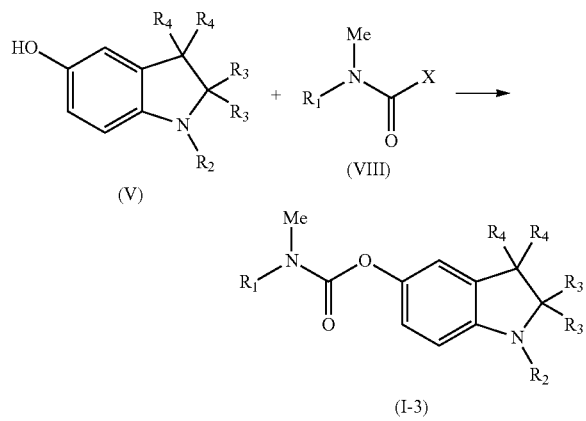

wherein $R_1$, $R_2$, $R_3$, and $R_4$ have the same meaning as defined above.

The solvent used in this reaction is not particularly limited so long as the solvent does not inhibit the reaction. Examples of the solvent include methylene chloride and tetrahydrofuran. Examples of the base used in the reaction include organic bases such as triethylamine and N,N-diisopropylethylamine.

The reaction time is not particularly limited and is usually one minute to 48 hours for any reaction, preferably five minutes to three hours.

The reaction temperature is usually −78° C. to 150° C. for any reaction, more preferably 0° C. to room temperature.

When the compound (I) according to the present invention is obtained as a free form, the compound (I) can be converted to the above-mentioned salt state which the compound (I) can form according to a usual method. Various isomers of the compound (I) according to the present invention that can be obtained can be purified and isolated using a usual separation method (for example, recrystallization or chromatography). Particularly, if an optically active substance of the compound according to the present invention is needed, the optically active substance can be obtained by a usual method such as optical resolution.

A drug product can be prepared from the compound (I) according to the present invention by a common method in the form of tablet, powder, subtilized granule, granule, coated tablet, capsule, syrup, lozenge, inhalant, suppository, injection, ointment, eye ointment, eye drop, nasal drop, ear drop, compress, lotion, or the like. Diluent, binder, lubricant, coloring material, and flavoring agent usually used for preparation of a drug product, as well as, if necessary, stabilizer, emulsifier, absorption promoting agent, surfactant, pH modulator, preservative, antioxidant, and the like can be used. Generally, components used as raw materials of a drug product are mixed and formulated by a usual method. For example, to produce an oral preparation, the compound according to the present invention or a pharmacologically acceptable salt and a diluent as well as, if necessary, a binder, a disintegrating agent, a lubricant, a coloring material, a flavoring agent, and the like are added, and then prepared as a powder, a subtilized granule, a granule, a tablet, a coated tablet, or a capsule by a usual method. Examples of these components include animal or vegetable oils such as soybean oil, beaf tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; silicon resin; silicon oil; surfactants such as polyoxyethylene fatty acid ester, sorbitan fatty acid ester, glycerine fatty acid ester, polyoxyethylene sorbitan fatty acid ester, polyoxyethylene hydrogenated caster oil, and polyoxyethylene-polyoxypropylene block copolymer; water-soluble polymers such as hydroxyethylcellulose, polyacrylic acid, carboxyvinyl polymer, polyethylene glycol, polyvinylpyrrolidone, and methylcellulose; lower alcohols such as ethanol and isopropanol; polyhydric alcohols such as glycerine, propylene glycol, dipropylene glycol, and sorbitol; sugars such as glucose and sucrose; inorganic powders such as anhydrous silicic acid, magnesium aluminium silicate, and aluminium silicate; and purified water. Examples of diluents used include lactose, corn starch, saccharose, glucose, mannitol, sorbit, crystalline cellulose, and silicon dioxide. Examples of binders used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, polypropylene glycol-polyoxyethylene block polymer, and meglumine. Examples of disintegrating agents used include starch, agar, gelatin powder, crystalline cellulose, calcium carbonate, sodium hydrogencarbonate, calcium citrate, dextrin, pectin, and carboxymethylcellulose calcium. Examples of lubricants used include magnesium stearate, talc, polyethylene glycol, silica, and hydrogenated vegetable oil. Coloring materials that are permitted to be added to a drug are used. Examples of flavoring agents used include cocoa powder, menthol, aromatic powder, peppermint oil, borneol, and cinnamon powder. These tablets and granules may of course be sugar-coated or suitably coated as required. A solution such as a syrup or a preparation for injection can be prepared by a usual method by adding the compound according to the present invention or a pharmacologically acceptable salt, a pH modifier, a solubilizing agent, an isotonizing agent, and the like, as well as, if necessary, a dissolving aid, a stabilizer, and the like. The method for producing a topical agent is not limited, and a topical agent can be produced by a usual method. Specifically, various raw materials usually used for drugs, quasi-drugs, cosmetics, and the like can be used as raw materials of a vehicle to prepare a drug product. Specific examples of raw materials of a vehicle include raw materials such as animal and vegetable oils, mineral oils, ester oils, waxes, higher alcohols, fatty acids, silicon oil, surfactants, phospholipids, alcohols, polyhydric alcohols, water-soluble polymers, clay minerals, and purified water. If necessary, pH modifiers, antioxidants, chelating agents, antiseptic-fungicides, coloring agents, flavors, and the like can be further added. However, raw materials for a vehicle of the topical agent according to the present invention are not limited to these examples. Furthermore, if necessary, components such as components having a differentiation inducing action, blood flow promoting agents, disinfectants, antiphlogistics, cell activating agents, vitamins, amino acids, moisturizing agents, and keratolyzing agents can also be mixed. The amounts of the above-mentioned raw materials of a vehicle to be added are usually amounts required to obtain concentrations selected for production of a topical agent.

The dosage form of an agent comprising the compound (I) according to the present invention or a pharmacologically acceptable salt as an active ingredient is not particularly limited, and the agent may be administered orally or parenterally by a usually used method. For example, a drug product is prepared in the dosage form such as tablet, powder, granule, capsule, syrup, lozenge, inhalant, suppository, injection, ointment, eye ointment, eye drop, nasal drop, ear drop, compress, or lotion and can be administered. The dose of the medicament according to the present invention can be suitably selected depending on symptom severity, age, sex, body weight, dosage form, salt type, specific disease type, and the like.

Reference Examples, Examples (and pharmacologically acceptable salts thereof, solvates thereof, medicaments or pharmaceutical compositions comprising the same), and Test Examples are described below as examples, and the compounds according to the present invention are limited in no way to the specific examples described below. Those skilled in the art can make various modifications to the Examples described below as well as the claims according to the present specification to make the best of the present invention, and such modifications are included in the claims according to the present specification.

EXAMPLE

Example 1

Synthesis of 1-methylindolin-5-yl 4-isopropylphenylcarbamate (1) Synthesis of 1-methylindolin-5-ol To a solution of 5-methoxyindole (200 mg, 1.36 mmol) in 1.5 mL of dry N,N-dimethylformamide was added sodium hydride (55%, 66 mg, 1.5 mmol) at 0° C. After the reaction mixture was stirred at the same temperature for 30 min, methyl iodide (0.10 mL, 1.6 mmol) was added with additional stirring at room temperature overnight. After the reaction mixture was quenched with water (5 mL) at 0° C., the solution was extracted with diethyl ether (20 mL) twice. The combined extracts were washed with brine (5 mL), and dried over MgSO$_4$. After filtration, the filtrate was concentrated in vacuo, and the residue was purified by silica gel column chromatography (hexane/ethyl acetate=95/5 to 80/20) to obtain 5-methoxy-1-methylindole (182 mg, 83%).

To a solution of 5-methoxy-1-methylindole (182 mg, 1.13 mmol) in 2.3 mL of acetic acid was added trifluoroacetic acid (1.1 mL). After the reaction mixture was added sodium cyanoborohydride (142 mg, 2.26 mmol) at 0° C., the reaction mixture was stirred at the same temperature for 2 h. After the reaction mixture was basified by 50% sodium hydroxide aqueous solution, the solution was extracted with diethyl ether (20 mL) twice. The combined extracts were washed with brine (5 mL), and dried over MgSO$_4$. After filtration, the filtrate was concentrated in vacuo, and the residue was purified by silica gel column chromatography (hexane/ethyl acetate=95/5 to 80/20) to obtain 5-methoxy-1-methylindoline (131 mg, 71%).

To a solution of 5-methoxy-1-methylindoline (131 mg, 0.802 mmol) in 4.0 mL of dry dichloromethane was added boron tribromide (0.38 mL, 4.0 mmol) under nitrogen at 0° C. After the reaction mixture was stirred at the same temperature for 30 min, methanol (1 mL) was added with additional stirring at room temperature for 5 min. After the reaction mixture was neutralized by saturated NaHCO$_3$ aqueous solution, the solution was extracted with diethyl ether (20 mL) twice. The combined extracts were washed with brine, and dried over MgSO$_4$. After filtration, the filtrate was concentrated in vacuo, and the residue was purified by silica gel column chromatography (hexane/ethyl acetate=90/10 to 50/50) to obtain the title compound (63 mg, 53%).

(2) Synthesis of 1-methylindolin-5-yl 4-isopropylphenylcarbamate

To a solution of 1-methylindolin-5-ol (18 mg, 0.12 mmol) in 0.6 mL of dry diethyl ether was added sodium hydride (55%, 19 mg, 0.43 mmol) at room temperature. After the reaction mixture was stirred at the same temperature for 2 min, 4-isopropylphenylisocyanate (29 μL, 0.18 mmol) was added with additional stirring for 5 min to 10 min. After the reaction mixture was quenched with water (1 mL), the solution was extracted with diethyl ether (10 mL). The extract was washed with brine, and dried over MgSO$_4$. After filtration, the filtrate was concentrated in vacuo, and the residue was purified by silica gel column chromatography (hexane/ethyl acetate=90/10 to 60/40) to obtain the title compound (5.4 mg, 14%).

$^1$H-NMR (CDCl$_3$) δ(ppm): 1.24 (d, J=6.8 Hz, 6H), 2.76 (s, 3H), 2.88 (sep, J=6.8 Hz, 1H), 2.96 (t, J=8.2 Hz, 2H), 3.34 (t, J=8.2 Hz, 2H), 6.47 (d, J=8.2 Hz, 1H), 6.82 (brs, 1H), 6.87 (d, J=8.2 Hz, 2H), 6.92 (s, 1H), 7.18 (d, J=8.2 Hz, 2H), 7.35 (d, J=8.2 Hz, 1H). MS (ESI+) m/z 311.4 (M+1).

Example 2

Synthesis of 1-benzylindolin-5-yl 4-isopropylphenylcarbamate (1) Synthesis of 1-benzylindolin-5-ol To a solution of 5-methoxyindole (147 mg, 1.00 mmol) in 2.5 mL of tetrahydrofuran was added acetic acid (2.5 mL) and sodium cyanoborohydride (220 mg, 3.50 mmol) at room temperature. After the reaction mixture was stirred at the same temperature for 20 min, benzaldehyde (0.20 mL, 2.0 mmol) was added with additional stirring for 1 h. After the reaction mixture was diluted with water (20 mL) and a 1:1 solution (20 mL) of hexane and ethyl acetate, the aqueous layer was extracted with a 1:1 solution (20 mL) of hexane and ethyl acetate. The combined extracts were washed with saturated NaHCO$_3$ aqueous solution, brine, and dried over MgSO$_4$. After filtration, the filtrate was concentrated in vacuo, and the residue was purified by silica gel column chromatography (hexane/ethyl acetate=90/10 to 80/20) to obtain 5-methoxy-1-benzylindoline (158 mg, 66%) as a sticky oil. To 5-methoxy-1-benzylindoline (4.30 g, 18.0 mmol) was added a solution of 50% hydrogen bromide-acetic acid solution (90 mL) at room temperature. After the reaction mixture was stirred at 115° C. for 22 h, the reaction mixture was neutralized by saturated NaHCO$_3$ aqueous solution (200 mL) and the solution was extracted with ethyl acetate (200 mL) twice. The combined extracts were washed with brine, and dried over MgSO$_4$. After filtration, the filtrate was concentrated in vacuo, and the residue was purified by silica gel column chromatography (hexane/ethyl acetate=80/20 to 70/30) to obtain the title compound (3.78 g, 93%) as a sticky oil.

(2) Synthesis of 1-benzylindolin-5-yl 4-isopropylphenylcarbamate

To a solution of 1-benzylindolin-5-ol (1.50 g, 6.66 mmol) in 33 mL of diethyl ether (5 mL/mmol) was added a piece of sodium (1 mg to 10 mg) at room temperature. After the reaction mixture was stirred at the same temperature for 2 min, 4-isopropylphenylisocyanate (1.3 mL, 8.0 mmol, 1.2 equivalent) was added with additional stirring for 5 min to 10 min. After removal of sodium, the filtrate was concentrated in vacuo, and the residue was purified by silica gel column chromatography (hexane/ethyl acetate=90/10 to 0/100) to obtain the title compound (2.24 g, 87%) as a white solid.

$^1$H-NMR (CDCl$_3$) δ(ppm): 1.23 (d, J=6.8 Hz, 6H), 2.88 (sep, J=6.8 Hz, 1H), 2.97 (t, J=8.2 Hz, 2H), 3.34 (t, J=8.2 Hz, 2H), 4.23 (s, 2H), 6.43 (d, J=8.2 Hz, 1H), 6.82 (dd, J=2.4, 8.2

Hz, 1H), 6.76-6.86 (brs, 1H), 6.92 (s, 1H), 7.19 (d, J=8.2 Hz, 2H), 7.25-7.40 (m, 7H). Melting Point 145-150° C., MS (ESI+) m/z 387.4 (M+1).

Example 3

Synthesis of 1-phenethylindolin-5-yl 4-isopropylphenylcarbamate (1) Synthesis of 1-phenethylindolin-5-ol To a solution of 5-methoxyindoline (175 mg, 1.17 mmol) in 3.6 mL of dry N,N-dimethylformamide was added sodium hydride (55%, 70 mg, 1.6 mmol) at 0° C. After the reaction mixture was stirred at the same temperature for 30 min, (2-bromoethyl)benzene (0.22 mL, 1.6 mmol) was added with additional stirring at room temperature overnight. After the reaction mixture was quenched with water at 0° C., the solution was extracted with diethyl ether (20 mL) twice. The combined extracts were washed with brine, and dried over $MgSO_4$. After filtration, the filtrate was concentrated in vacuo, and the residue was purified by silica gel column chromatography (hexane/ethyl acetate=95/5 to 85/15) to obtain 5-methoxy-1-phenethylindole (95 mg, 32%).

To a solution of 5-methoxy-1-phenethylindole (95 mg, 0.38 mmol) in 1.9 mL of dry dichloromethane was added boron tribromide-dichloromethane solution (4 M, 0.47 mL, 1.9 mmol) under nitrogen at 0° C. After the reaction mixture was stirred at room temperature for 30 min, methanol (1 mL) was added with additional stirring at room temperature for 5 min. After the reaction mixture was neutralized by saturated $NaHCO_3$ aqueous solution, the solution was extracted with ethyl acetate. The extract was washed with brine, and dried over $MgSO_4$. After filtration, the filtrate was concentrated in vacuo, and the residue was purified by silica gel column chromatography (chloroform/methanol=100/0 to 95/5) to obtain the title compound (25.3 mg, 28%).

(2) Synthesis of 1-phenethylindolin-5-yl 4-isopropylphenylcarbamate

The title compound was synthesized using the same procedure employed for Example 2 (2), but with 1-phenethylindolin-5-ol (25.3 mg, 0.106 mmol) instead of 1-benzylindolin-5-ol (1.50 g, 6.66 mmol). The product was obtained as a white solid (26.7 mg, 63%) having the following characteristics.

$^1$H-NMR (CDCl$_3$) δ(ppm): 1.23 (d, J=6.9 Hz, 6H), 2.85-2.92 (m, 3H), 2.96 (t, J=8.7 Hz, 2H), 3.31 (t, J=7.8 Hz, 2H), 3.41 (t, J=8.7 Hz, 2H), 6.41 (d, J=8.7 Hz, 1H), 6.83 (dd, J=2.4, 8.7 Hz, 1H), 6.8-6.9 (brs, 1H), 6.90 (brs, 1H), 7.18 (d, J=8.2 Hz, 2H), 7.2-7.4 (m, 7H). Melting Point 128-131° C., MS (ESI+) m/z 401 (M+1).

Example 4

Synthesis of 1-(3-phenylpropyl)indolin-5-yl-4-isopropylphenylcarbamate (1) Synthesis of 1-(3-phenylpropyl)indolin-5-ol The title compound was synthesized using the same procedure employed for Example 3 (1), but with (3-bromopropyl)benzene instead of (2-bromoethyl)benzene. The product was obtained (32.7 mg, 2 steps 11%).

(2) Synthesis of 1-(3-phenylpropyl)indolin-5-yl 4-isopropylphenylcarbamate

The title compound was synthesized using the same procedure employed for Example 2 (2), but with 1-(3-phenylpropyl)indolin-5-ol (16.1 mg, 63.6 μmol) instead of 1-benzylindolin-5-ol (1.50 g, 6.66 mmol). The product was obtained as a white solid (19.6 mg, 74%) having the following characteristics.

$^1$H-NMR (CDCl$_3$) δ(ppm): 1.23 (d, J=6.7 Hz, 6H), 1.92 (tt, J=7.3, 7.8 Hz, 2H), 2.72 (t, J=7.8 Hz, 2H), 2.87 (sep, J=6.7 Hz, 1H), 2.96 (t, J=8.2 Hz, 2H), 3.34 (t, J=7.3 Hz, 2H), 3.35 (t, J=8.2 Hz, 2H), 6.33 (d, J=8.2 Hz, 1H), 6.8-6.83 (brs, 1H), 6.81 (dd, J=2.4, 8.2 Hz, 1H), 6.89 (d, J=2.4 Hz, 1H), 7.15-7.3 (m, 7H), 7.35 (d, J=8.2 Hz, 2H). Melting Point 139-143° C., MS (ESI+) m/z 415 (M+1).

Example 5

Synthesis of 1-(2-cyclohexylethyl)indolin-5-yl-4-isopropylphenylcarbamate (1) Synthesis of 1-(2-cyclohexylethyl)indolin-5-ol The title compound was synthesized using the same procedure employed for Example 3 (1), but with 1-bromo-2-cyclohexylethane instead of (2-bromoethyl)benzene. The product was obtained (34.0 mg, 2 steps 12%).

(2) Synthesis of 1-(2-cyclohexylethyl)indolin-5-yl-4-isopropylphenylcarbamate

The title compound was synthesized using the same procedure employed for Example 2 (2), but with 1-(2-cyclohexylethyl)indolin-5-ol (34.0 mg, 0.139 mmol) instead of 1-benzylindolin-5-ol (1.50 g, 6.66 mmol). The product was obtained as a white solid (37.8 mg, 67%) having the following characteristics. MS (ESI+) m/z 407 (M+1).

Example 6

Synthesis of 1-n-hexylindolin-5-yl-4-isopropylphenylcarbamate (1) Synthesis of 1-n-hexylindolin-5-ol The title compound was synthesized using the same procedure employed for Example 3 (1), but with 1-bromohexane instead of (2-bromoethyl)benzene. The product was obtained (86.5 mg, 2 steps 34%).

(2) Synthesis of 1-n-hexylindolin-5-yl-4-isopropylphenylcarbamate

The title compound was synthesized using the same procedure employed for Example 2 (2), but with 1-n-hexylindolin-5-ol (58.7 mg, 0.268 mmol) instead of 1-benzylindolin-5-ol (1.50 g, 6.66 mmol). The product was obtained as a white solid (64.0 mg, 63%) having the following characteristics.

$^1$H-NMR (CDCl$_3$) δ(ppm): 0.90 (t, J=6.9 Hz, 3H), 1.23 (d, J=6.8 Hz, 6H), 1.3-1.5 (m, 2H), 1.5-1.7 (m, 2H), 2.88 (sep, J=6.9 Hz, 1H), 2.95 (t, J=8.2 Hz, 2H), 3.01 (t, J=7.8 Hz, 2H), 3.34 (t, J=8.2 Hz, 2H), 6.39 (d, J=8.2 Hz, 1H), 6.8-6.85 (brs, 1H), 6.82 (dd, J=2.4, 8.2 Hz, 1H), 6.88 (d, J=2.4 Hz, 1H), 7.18 (d, J=8.2 Hz, 2H), 7.35 (d, J=8.2 Hz, 2H). Melting Point 120-124° C., MS (ESI+) m/z 381 (M+1).

Example 7

Synthesis of 1-(3,3-dimethylbutyl)indolin-5-yl 4-isopropylphenylcarbamate (1) Synthesis of 1-(3,3-dimethylbutyl)indolin-5-ol To a solution of 5-methoxyindoline (180 mg, 1.21 mmol) in 3.6 mL of acetic acid was added 3,3-dimethylbutylaldehyde (0.18 mL, 1.4 mmol) and sodium cyanoborohydride (190 mg, 3.0 mmol) at room temperature, successively. After the reaction mixture was stirred for 2 h, the reaction mixture was basified by saturated NaHCO$_3$ aqueous solution and the solution was extracted with ethyl acetate (20 mL). The extract was washed with brine, and dried over MgSO$_4$. After filtration, the filtrate was concentrated in vacuo, and the residue was purified by silica gel column chromatography (hexane/ethyl acetate=95/5 to 90/10) to obtain 5-methoxy-1-(3,3-dimethylbutyl)indoline (74.6 mg, 26%).

The title compound was synthesized using the same procedure employed for Example 3 (1), but with 5-methoxy-1-(3,3-dimethylbutyl)indoline (74.6 mg, 0.320 mmol) instead of 5-methoxy-1-phenethylindole (95 mg, 0.38 mmol). The product was obtained (31.3 mg, 45%).

(2) Synthesis of 1-(3,3-dimethylbutyl)indolin-5-yl 4-isopropylphenylcarbamate

The title compound was synthesized using the same procedure employed for Example 2 (2), but with 1-(3,3-dimethylbutyl)indolin-5-ol (31.3 mg, 0.143 mmol) instead of 1-benzylindolin-5-ol (1.50 g, 6.66 mmol). The product was obtained as a white solid (37.8 mg, 69%) having the following characteristics. MS (ESI+) m/z 381 (M+1).

Example 8

Synthesis of 1-benzoylindolin-5-yl 4-isopropylphenylcarbamate (1) Synthesis of 1-benzoylindolin-5-ol To a solution of 5-methoxyindoline (202 mg, 1.35 mmol) and N,N-diisopropylethylamine (0.34 mL, 2.0 mmol) in 4.0 mL of dry dichloromethane was added benzoyl chloride (0.23 mL, 2.0 mmol) at 0° C. After the reaction mixture was stirred at room temperature for 1 h, the reaction mixture was diluted with ethyl acetate. The solution was washed with saturated NaHCO$_3$ aqueous solution, brine, and dried over MgSO$_4$. After filtration, the filtrate was concentrated in vacuo, and the residue was purified by silica gel column chromatography (hexane/ethyl acetate=95/5 to 70/30) to obtain 5-methoxy-1-benzoylindoline (224 mg, 65%).

The title compound was synthesized using the same procedure employed for Example 3 (1), but with 5-methoxy-1-benzoylindoline (110 mg, 0.434 mmol) instead of 5-methoxy-1-phenethylindole (95 mg, 0.38 mmol). The product was obtained (37 mg, 36%).

(2) Synthesis of 1-benzoylindolin-5-yl 4-isopropylphenylcarbamate

The title compound was synthesized using the same procedure employed for Example 2 (2), but with 1-benzoylindolin-5-ol (37 mg, 0.15 mmol) instead of 1-benzylindolin-5-ol (1.50 g, 6.66 mmol). The product was obtained having the following characteristics (19.4 mg, 31%). $^1$H-NMR (CDCl$_3$) δ(ppm): 1.23 (d, J=6.9 Hz, 6H), 2.89 (sep, J=6.9 Hz, 1H), 3.13 (t, J=8.2 Hz, 2H), 4.11 (brs, 2H), 6.87 (brs, 1H), 7.07 (brs, 1H), 7.20 (d, J=8.2 Hz, 2H), 7.3-7.6 (m, 9H). MS (ESI+) m/z 401 (M+1).

Example 9

Synthesis of 1-benzylindolin-5-yl 4-methoxyphenylcarbamate

The title compound was synthesized from 1-benzylindolin-5-ol (30.0 mg, 0.133 mmol) using the same procedure employed for Example 2 (2), but with 4-methoxyphenylisocyanate instead of 4-isopropylphenylisocyanate. The product was obtained as a white solid (13.2 mg, 27%) having the following characteristics.

$^1$H-NMR (CDCl$_3$) δ(ppm): 2.96 (t, J=8.2 Hz, 2H), 3.33 (t, J=8.2 Hz, 2H), 3.79 (s, 3H), 4.22 (s, 2H), 6.43 (d, J=8.7 Hz, 1H), 6.75-6.85 (brs, 1H), 6.82 (dd, J=2.4, 8.2 Hz, 1H), 6.86 (d, J=8.2 Hz, 2H), 6.91 (d, J=2.4 Hz, 1H), 7.25-7.40 (m, 7H). Melting Point 160-166° C., MS (ESI+) m/z 375 (M+1).

Example 10

Synthesis of 1-benzylindolin-5-yl 3-phenoxyphenylcarbamate

The title compound was synthesized from 1-benzylindolin-5-ol (30.0 mg, 0.133 mmol) using the same procedure employed for Example 2 (2), but with 3-phenoxyphenylisocyanate instead of 4-isopropylphenylisocyanate. The product was obtained having the following characteristics (16.5 mg, 28%).

MS (ESI+) m/z 437 (M+1).

Example 11

Synthesis of 1-benzylindolin-5-yl 2,3-dihydro-1,4-benzodioxin-6-ylcarbamate

The title compound was synthesized from 1-benzylindolin-5-ol (30.0 mg, 0.133 mmol) using the same procedure employed for Example 2 (2), but with 2,3-dihydro-1,4-benzodioxin-6-ylisocyanate instead of 4-isopropylphenylisocyanate. The product was obtained as a solid (29.1 mg, 50%) having the following characteristics.

MS (ESI+) m/z 403 (M+1).

Example 12

Synthesis of 1-benzylindolin-5-yl 5-benzo[d][1,3]dioxolylcarbamate

The title compound was synthesized from 1-benzylindolin-5-ol (35.0 mg, 0.155 mmol) using the same procedure employed for Example 2 (2), but with 3,4-(methylenedioxy)phenylisocyanate instead of 4-isopropylphenylisocyanate. The product was obtained as a white solid (21.6 mg, 34%) having the following characteristics.

$^1$H-NMR (CDCl$_3$) δ(ppm): 2.95 (t, J=8.2 Hz, 2H), 3.32 (t, J=8.2 Hz, 2H), 4.21 (s, 2H), 5.95 (s, 2H), 6.42 (d, J=8.2 Hz, 1H), 6.7-6.85 (m, 4H), 6.91 (s, 1H), 7.15 (brs, 1H), 7.25-7.4 (m, 4H). Melting Point 132-135° C., MS (ESI+) m/z 389 (M+1).

Example 13

Synthesis of 1-benzylindolin-5-yl 4-phenoxyphenylcarbamate

The title compound was synthesized from 1-benzylindolin-5-ol (35.0 mg, 0.155 mmol) using the same procedure employed for Example 2 (2), but with 4-phenoxyphenylisocyanate instead of 4-isopropylphenylisocyanate. The product was obtained as a white solid (7.4 mg, 11%) having the following characteristics.
$^1$H-NMR (CDCl$_3$) δ(ppm): 2.97 (t, J=8.2 Hz, 2H), 3.34 (t, J=8.2 Hz, 2H), 4.23 (s, 2H), 6.43 (d, J=8.7 Hz, 1H), 6.82 (dd, J=2.4, 8.7 Hz, 1H) 6.87 (brs, 1H), 6.92 (brs, 1H), 6.95-7.05 (m, 4H), 7.08 (d, J=6.9 Hz, 2H), 7.25-7.38 (m, 6H), 7.41 (d, J=8.7 Hz, 2H). Melting Point 155-160° C., MS (ESI+) m/z 437 (M+1).

Example 14

Synthesis of 1-benzylindolin-5-yl 2,3-dihydro-1-benzofuran-5-ylcarbamate

The title compound was synthesized from 1-benzylindolin-5-ol (35.0 mg, 0.155 mmol) using the same procedure employed for Example 2 (2), but with 2,3-dihydro-1-benzofuran-5-ylisocyanate instead of 4-isopropylphenylisocyanate. The product was obtained as a white solid (9.0 mg, 13%) having the following characteristics.
MS (ESI+) m/z 387 (M+1).

Example 15

Synthesis of 1-benzylindolin-5-yl benzylcarbamate

The title compound was synthesized from 1-benzylindolin-5-ol (35.0 mg, 0.155 mmol) using the same procedure employed for Example 2 (2), but with benzylisocyanate instead of 4-isopropylphenylisocyanate. The product was obtained as a white solid (17.0 mg, 31%) having the following characteristics.
$^1$H-NMR (CDCl$_3$) δ(ppm): 2.95 (t, J=8.2 Hz, 2H), 3.32 (t, J=8.2 Hz, 2H), 4.21 (s, 2H), 4.44 (d, J=6.0 Hz, 2H), 5.26 (brs, 1H), 6.41 (d, J=8.2 Hz, 1H), 6.78 (dd, J=1.9, 8.2 Hz, 1H), 6.88 (brs, 1H), 7.25-7.43 (m, 10H). Melting Point 70-72° C., MS (ESI+) m/z 359 (M+1).

Example 16

Synthesis of 1-benzylindolin-5-yl phenethylcarbamate

The title compound was synthesized from 1-benzylindolin-5-ol (35.0 mg, 0.155 mmol) using the same procedure employed for Example 2 (2), but with phenethylisocyanate instead of 4-isopropylphenylisocyanate. The product was obtained as a white solid (22.0 mg, 38%) having the following characteristics.
$^1$H-NMR (CDCl$_3$) δ(ppm): 2.8-3.0 (m, 4H), 3.31 (t, J=8.2 Hz, 2H), 3.52 (q, J=6.4 Hz, 2H), 4.21 (s, 2H), 4.96 (brs, 1H), 6.40 (d, J=8.7 Hz, 1H), 6.74 (dd, J=2.4, 8.7 Hz, 1H), 6.84 (brs, 1H), 7.1-7.4 (m, 10H). Melting Point 95-98° C., MS (ESI+) m/z 373 (M+1).

Example 17

Synthesis of 1-benzylindolin-5-yl n-hexylcarbamate

The title compound was synthesized from 1-benzylindolin-5-ol (35.0 mg, 0.155 mmol) using the same procedure employed for Example 2 (2), but with n-hexylisocyanate instead of 4-isopropylphenylisocyanate. The product was obtained as a white solid (16.7 mg, 30%) having the following characteristics.
$^1$H-NMR (CDCl$_3$) δ(ppm): 0.90 (t, J=6.8 Hz, 3H), 1.25-1.3 (m, 6H), 1.5-1.7 (m, 2H), 2.94 (t, J=8.2 Hz, 2H), 3.24 (q, J=6.7 Hz, 2H), 3.31 (t, J=8.2 Hz, 2H), 4.21 (s, 2H), 4.94 (brs, 1H), 6.41 (d, J=8.2 Hz, 1H), 6.76 (dd, J=2.4, 8.2 Hz, 1H), 6.86 (brs, 1H), 7.2-7.4 (m, 5H). Melting Point 80-82° C., MS (ESI+) m/z 353 (M+1).

Example 18

Synthesis of 1-benzylindolin-5-yl furfurylcarbamate

The title compound was synthesized from 1-benzylindolin-5-ol (35.0 mg, 0.155 mmol) using the same procedure employed for Example 2 (2), but with furfurylisocyanate instead of 4-isopropylphenylisocyanate. The product was obtained as a white solid (15.3 mg, 28%) having the following characteristics.
MS (ESI+) m/z 349 (M+1).

Example 19

Synthesis of 1-benzylindolin-5-yl (S)-1-phenylethylcarbamate

The title compound was synthesized from 1-benzylindolin-5-ol (35.0 mg, 0.155 mmol) using the same procedure employed for Example 2 (2), but with (S)-α-methylbenzylisocyanate instead of 4-isopropylphenylisocyanate. The product was obtained as a white solid (14.8 mg, 27%) having the following characteristics.
MS (ESI+) m/z 373 (M+1).

Example 20

Synthesis of 1-benzylindolin-5-yl cyclohexylcarbamate

The title compound was synthesized from 1-benzylindolin-5-ol (35.0 mg, 0.155 mmol) using the same procedure employed for Example 2 (2), but with cyclohexylisocyanate instead of 4-isopropylphenylisocyanate. The product was obtained as a white solid (14.8 mg, 27%) having the following characteristics.
$^1$H-NMR (CDCl$_3$) δ(ppm): 1.1-2.1 (m, 9H), 2.94 (t, J=8.2 Hz, 2H), 3.31 (t, J=8.2 Hz, 2H), 3.5-3.6 (m, 1H), 4.0-4.15 (m, 1H), 4.21 (s, 2H), 4.82 (brd, J=7.2 Hz, 1H), 6.40 (d, J=8.2 Hz, 1H), 6.76 (d, J=2.4, 8.2 Hz, 1H), 6.86 (brs, 1H), 7.25-7.4 (m, 5H). Melting Point 124-128° C., MS (ESI+) m/z 351 (M+1).

Example 21

Synthesis of 1-benzylindolin-5-yl 4-nitrophenylcarbamate

The title compound was synthesized from 1-benzylindolin-5-ol (70.0 mg, 0.311 mmol) using the same procedure employed for Example 2 (2), but with 4-nitrophenylisocyanate instead of 4-isopropylphenylisocyanate. The product was obtained as a slightly yellow solid (7.1 mg, 6%) having the following characteristics.

$^1$H-NMR (CDCl$_3$) δ(ppm): 2.99 (t, J=8.2 Hz, 2H), 3.37 (t, J=8.2 Hz, 2H), 4.25 (s, 2H), 6.44 (d, J=8.7 Hz, 1H), 6.82 (dd, J=2.4, 8.7 Hz, 1H), 6.91 (brs, 1H), 7.25-7.4 (m, 6H), 7.61 (d, J=8.2 Hz, 2H), 8.23 (d, J=8.2 Hz, 2H). Melting Point 225-229° C., MS (ESI+) m/z 390 (M+1).

Example 22

Synthesis of indolin-5-yl 4-isopropylphenylcarbamate

To a solution of 1-benzylindolin-5-yl 4-isopropylphenylcarbamate (300 mg, 0.776 mmol) in a 2:1 solution (3.0 mL) of isopropylalcohol and 6 M HCl was added palladium 10% on carbon (30 mg) under nitrogen. After the vessel was purged with hydrogen, the reaction mixture was stirred under 1 atm of hydrogen at room temperature overnight. After the vessel was purged with nitrogen, the reaction mixture was filtered to remove palladium 10% on carbon. The filtrate was concentrated in vacuo. After the residue was diluted with ethyl acetate, the solution was washed with saturated NaHCO$_3$ aqueous solution, brine, and dried over MgSO$_4$. After filtration, the filtrate was concentrated in vacuo, and the residue was purified by silica gel column chromatography (hexane/ethyl acetate=85/15 to 40/60) to obtain the title compound as a white solid (220 mg, 96%).

$^1$H-NMR (CDCl$_3$) δ(ppm): 1.23 (d, J=6.8 Hz, 6H), 2.88 (sep, J=6.8 Hz, 1H), 3.04 (t, J=8.7 Hz, 2H), 3.34 (t, J=8.7 Hz, 2H), 6.60 (d, J=8.2 Hz, 1H), 6.79 (dd, J=1.9, 8.2 Hz, 1H), 6.94 (brs, 1H), 7.18 (d, J=8.2 Hz, 2H), 7.35 (d, J=8.2 Hz, 2H). Melting Point 166-170° C., MS (ESI+) m/z 297.3 (M+1).

Example 23

Synthesis of 1-(4-methoxybenzyl)indolin-5-yl 4-isopropylphenylcarbamate

To a solution of indolin-5-yl 4-isopropylphenylcarbamate (15.0 mg, 50.6 µmol) in 0.75 mL of dry dichloromethane was added 4-methoxybenzaldehyde (12.3 µL, 0.101 mmol) at room temperature. After the reaction mixture was stirred at the same temperature for 2 min, acetic acid (29 µL, 0.51 mmol) and sodium triacetoxyhydroborate (38 mg, 0.18 mmol) was added, successively. After the reaction mixture was stirred at the same temperature for 30 min, the reaction mixture was diluted with diethyl ether (2 mL). After the reaction mixture was neutralized by saturated NaHCO$_3$ aqueous solution (1 mL), the organic layer was separated. The separated organic layer was concentrated in vacuo, and the residue was purified by silica gel column chromatography (hexane/ethyl acetate=90/10 to 50/50) to obtain the title compound as a white solid (17.2 mg, 82%).

MS (ESI+) m/z 417.4 (M+1).

Example 24

Synthesis of 1-(4-trifluoromethylbenzyl)indolin-5-yl 4-isopropylphenylcarbamate

The title compound was synthesized using the same procedure employed for Example 23, but with 4-trifluoromethylbenzaldehyde instead of 4-methoxybenzaldehyde. The product was obtained as a white solid (17.2 mg, 75%) having the following characteristics.

MS (ESI+) m/z 455.4 (M+1).

Example 25

Synthesis of 1-(4-dimethylaminobenzyl)indolin-5-yl 4-isopropylphenylcarbamate

The title compound was synthesized using the same procedure employed for Example 23, but with 4-dimethylaminobenzaldehyde instead of 4-methoxybenzaldehyde. The product was obtained as a slightly yellow solid (18.5 mg, 85%) having the following characteristics.

MS (ESI+) m/z 452.4 (M+Na).

Example 26

Synthesis of 1-(4-chlorobenzyl)indolin-5-yl 4-isopropylphenylcarbamate

The title compound was synthesized using the same procedure employed for Example 23, but with 4-chlorobenzaldehyde instead of 4-methoxybenzaldehyde. The product was obtained as a white solid (15.2 mg, 72%) having the following characteristics.

MS (ESI+) m/z 421.3 (M+1).

Example 27

Synthesis of 1-(4-pyridylmethyl)indolin-5-yl 4-isopropylphenylcarbamate

The title compound was synthesized using the same procedure employed for Example 23, but with 4-pyridinecarboxyaldehyde instead of 4-methoxybenzaldehyde. The product was obtained as a white solid (15.0 mg, 77%) having the following characteristics.

MS (ESI+) m/z 388.3 (M+1).

Example 28

Synthesis of 1-(3-pyridylmethyl)indolin-5-yl 4-isopropylphenylcarbamate

The title compound was synthesized using the same procedure employed for Example 23, but with 3-pyridinecarboxyaldehyde instead of 4-methoxybenzaldehyde. The product was obtained as a white solid (17.4 mg, 89%) having the following characteristics.

MS (ESI+) m/z 388.3 (M+1).

Example 29

Synthesis of 1-(1-naphtylmethyl)indolin-5-yl 4-isopropylphenylcarbamate

The title compound was synthesized using the same procedure employed for Example 23, but with 1-naphtaldehyde instead of 4-methoxybenzaldehyde. The product was obtained as a white solid (12.3 mg, 57%) having the following characteristics.

MS (ESI+) m/z 437.3 (M+1).

Example 30

Synthesis of 1-(benzol-[1,3]-dioxol-5-ylmethyl)indolin-5-yl 4-isopropylphenylcarbamate The title compound was synthesized using the same procedure employed for Example 23, but with piperonal instead of 4-methoxybenzaldehyde. The product was obtained as a white solid (16.6 mg, 76%) having the following characteristics.

MS (ESI+) m/z 431.3 (M+1).

Example 31

Synthesis of 1-benzylindolin-5-yl 4-methoxybenzylcarbamate

To a solution of 1-benzylindolin-5-ol (15.0 mg, 66.6 µmol) in 0.50 mL of dry dichloromethane was added triphosgene (6.9 mg, 23 µmol) and N,N-diisopropylethylamine (14 µL, 82 µmol), successively. After the reaction mixture was stirred at room temperature for 10 min, 4-methoxybenzylamine (17 µL, 0.13 mmol) was added. After the reaction mixture was stirred at the same temperature for 30 min, the reaction mixture was diluted with hexane (1 mL) and 1 M HCl (2 mL). The organic layer was purified directly by silica gel column chromatography (eluting with hexane/ethyl acetate or chloroform/methanol) to obtain the title compound as a white solid (6.1 mg, 24%).

MS (ESI+) m/z 389 (M+1).

Example 32

Synthesis of 1-benzylindolin-5-yl 4-methoxyphenethylcarbamate

The title compound was synthesized using the same procedure employed for Example 31, but with 4-methoxyphenethylamine instead of 4-methoxybenzylamine. The product was obtained as a white solid (8.7 mg, 32%) having the following characteristics.

MS (ESI+) m/z 403 (M+1).

Example 33

Synthesis of 1-benzylindolin-5-yl 4-isopropylphenethylcarbamate

The title compound was synthesized using the same procedure employed for Example 31, but with 4-isopropylphenethylamine hydrochloride instead of 4-methoxybenzylamine. The product was obtained as a white solid (5.2 mg, 19%) having the following characteristics.

MS (ESI+) m/z 415 (M+1).

Example 34

Synthesis of 1-benzylindolin-5-yl cyclohexylmethylcarbamate

The title compound was synthesized using the same procedure employed for Example 31, but with cyclohexylmethylamine instead of 4-methoxybenzylamine. The product was obtained as a white solid (9.6 mg, 40%) having the following characteristics.

$^1$H-NMR (CDCl$_3$) δ(ppm): 0.97 (t, J=12 Hz, 2H), 1.1-1.3 (m, 3H), 1.45-1.55 (m, 1H), 1.65-1.8 (m, 5H), 2.95 (t, J=8.2 Hz, 2H), 3.09 (t, J=8.2 Hz, 2H), 3.31 (dd, J=6.3, 6.8 Hz, 2H), 4.21 (s, 2H), 4.95 (brs, 1H), 6.40 (d, J=8.7 Hz, 1H), 6.75 (dd, J=2.4, 8.7 Hz, 1H), 6.86 (d, J=2.4 Hz, 1H), 7.26-7.38 (m, 5H). Melting Point 108-112° C., MS (ESI+) m/z 365 (M+1).

Example 35

Synthesis of 1-benzylindolin-5-yl 2-methylpropylcarbamate

The title compound was synthesized using the same procedure employed for Example 31, but with 2-methylpropylamine instead of 4-methoxybenzylamine. The product was obtained as a white solid (4.7 mg, 22%) having the following characteristics.

MS (ESI+) m/z 325 (M+1).

Example 36

Synthesis of 1-benzylindolin-5-yl 3-methoxy-5-(trifluoromethyl)phenylcarbamate

The title compound was synthesized using the same procedure employed for Example 31, but with 3-methoxy-5-(trifluoromethyl)aniline instead of 4-methoxybenzylamine. The product was obtained having the following characteristics (2.8 mg, 10%).

MS (ESI+) m/z 443 (M+1).

Example 37

Synthesis of 1-benzylindolin-5-yl 5-tert-butyl-2-methoxyphenylcarbamate

The title compound was synthesized using the same procedure employed for Example 31, but with 5-tert-butyl-2-methoxyaniline instead of 4-methoxybenzylamine. The product was obtained as a sticky oil (9.0 mg, 31%) having the following characteristics.

MS (ESI+) m/z 431 (M+1).

Example 38

Synthesis of 1-benzylindolin-5-yl 1-(3-methoxyphenyl)ethylcarbamate

The title compound was synthesized using the same procedure employed for Example 31, but with 1-(3-methoxyphenyl)ethylamine instead of 4-methoxybenzylamine. The product was obtained as a sticky oil (5.7 mg, 21%) having the following characteristics.

MS (ESI+) m/z 403 (M+1).

Example 39

Synthesis of 1-benzylindolin-5-yl 2,4,6-trimethylbenzylcarbamate

The title compound was synthesized using the same procedure employed for Example 31, but with 2,4,6-trimethylbenzylamine instead of 4-methoxybenzylamine. The product was obtained as a white solid (8.2 mg, 31%) having the following characteristics.

MS (ESI+) m/z 401 (M+1).

Example 40

Synthesis of 1-benzylindolin-5-yl 4-isopropoxybenzylcarbamate

The title compound was synthesized using the same procedure employed for Example 31, but with 4-isopropoxybenzylamine instead of 4-methoxybenzylamine. The product was obtained having the following characteristics (2.8 mg, 10%).

MS (ESI+) m/z 417 (M+1).

Example 41

Synthesis of 1-benzylindolin-5-yl cyclopropylcarbamate

The title compound was synthesized using the same procedure employed for Example 31, but with cyclopropylamine instead of 4-methoxybenzylamine. The product was obtained as a white solid (8.0 mg, 39%) having the following characteristics.

MS (ESI+) m/z 309 (M+1).

Example 42

Synthesis of 1-benzylindolin-5-yl 3,3-dimethylbutylcarbamate

The title compound was synthesized using the same procedure employed for Example 31, but with 3,3-dimethylbutylamine instead of 4-methoxybenzylamine. The product was obtained as a white solid (5.5 mg, 24%) having the following characteristics.

MS (ESI+) m/z 353 (M+1).

Example 43

Synthesis of 1-benzylindolin-5-yl 4-tert-butylcyclohexylcarbamate

The title compound was synthesized using the same procedure employed for Example 31, but with 4-tert-butylcyclohexylamine instead of 4-methoxybenzylamine. The product was obtained as a white solid (2.9 mg, 11%) having the following characteristics.

MS (ESI+) m/z 407 (M+1).

Example 44

Synthesis of 1-benzylindolin-5-yl 2-indanylcarbamate

The title compound was synthesized using the same procedure employed for Example 31, but with 2-aminoindane instead of 4-methoxybenzylamine. The product was obtained as a white solid (6.8 mg, 27%) having the following characteristics.

MS (ESI+) m/z 385 (M+1).

Example 45

Synthesis of 1-benzylindolin-5-yl cyclooctylcarbamate

The title compound was synthesized using the same procedure employed for Example 31, but with cyclooctylamine instead of 4-methoxybenzylamine. The product was obtained as a white solid (4.4 mg, 17%) having the following characteristics.

MS (ESI+) m/z 379 (M+1).

Example 46

Synthesis of 1-benzylindolin-5-yl 1-methoxybutan-2-ylcarbamate

The title compound was synthesized using the same procedure employed for Example 31, but with 2-amino-1-methoxybutane instead of 4-methoxybenzylamine. The product was obtained as a sticky oil (6.0 mg, 25%) having the following characteristics.

MS (ESI+) m/z 355 (M+1).

Example 47

Synthesis of 1-benzylindolin-5-yl 1-adamantanemethylcarbamate

The title compound was synthesized using the same procedure employed for Example 31, but with 1-adamantanemethylamine instead of 4-methoxybenzylamine. The product was obtained as a white solid (5.9 mg, 21%) having the following characteristics.

MS (ESI+) m/z 417 (M+1).

Example 48

Synthesis of 1-benzylindolin-5-yl 3-methoxypropylcarbamate

The title compound was synthesized using the same procedure employed for Example 31, but with 3-methoxypropylamine instead of 4-methoxybenzylamine. The product was obtained as a white solid (5.2 mg, 23%) having the following characteristics.

MS (ESI+) m/z 341 (M+1).

Example 49

Synthesis of 1-benzylindolin-5-yl 3-methylthiopropylcarbamate

The title compound was synthesized using the same procedure employed for Example 31, but with 3-methylthiopropylamine instead of 4-methoxybenzylamine. The product was obtained as a solid (5.0 mg, 21%) having the following characteristics.

MS (ESI+) m/z 357 (M+1).

Example 50

Synthesis of 1-benzylindolin-5-yl 2-heptylcarbamate

The title compound was synthesized using the same procedure employed for Example 31, but with 2-heptylamine instead of 4-methoxybenzylamine. The product was obtained as a white solid (5.5 mg, 23%) having the following characteristics.

MS (ESI+) m/z 367 (M+1).

Example 51

Synthesis of 1-benzylindolin-5-yl 2-tetrahydrofurylmethylcarbamate

The title compound was synthesized using the same procedure employed for Example 31, but with tetrahydrofurfurylamine instead of 4-methoxybenzylamine. The product was obtained as a white solid (8.6 mg, 37%) having the following characteristics.

MS (ESI+) m/z 353 (M+1).

Example 52

Synthesis of 1-benzylindolin-5-yl(S)-1-(1-naphthyl)ethylcarbamate

The title compound was synthesized using the same procedure employed for Example 31, but with (S)-1-(1-naphthyl)ethylamine instead of 4-methoxybenzylamine. The product was obtained as a sticky oil (5.1 mg, 18%) having the following characteristics.

MS (ESI+) m/z 423 (M+1).

Example 53

Synthesis of 1-benzylindolin-5-yl 2-methylallylcarbamate

The title compound was synthesized using the same procedure employed for Example 31, but with 2-methylallylamine hydrochloride instead of 4-methoxybenzylamine. The product was obtained as a solid (8.0 mg, 37%) having the following characteristics. Melting Point 75-80° C., MS (ESI+) m/z 323.3 (M+1).

Example 54

Synthesis of 1-benzylindolin-5-yl 2-(furfurylthio)ethylcarbamate

The title compound was synthesized using the same procedure employed for Example 31, but with 2-(furfurylthio)ethylamine instead of 4-methoxybenzylamine. The product was obtained as a sticky oil (12.0 mg, 44%) having the following characteristics.

MS (ESI+) m/z 409.4 (M+1).

Example 55

Synthesis of 1-benzylindolin-5-yl-4-methylphenylcarbamate

The title compound was synthesized from 1-benzylindolin-5-ol (15.0 mg, 66.6 µmol) using the same procedure employed for Example 2 (2), but with 4-methylphenylisocyanate instead of 4-isopropylphenylisocyanate. The product was obtained as a white solid (18.4 mg, 77%) having the following characteristics.

$^1$H-NMR (CDCl$_3$) δ(ppm): 2.32 (s, 3H), 2.97 (t, J=8.2 Hz, 2H), 3.34 (t, J=8.2 Hz, 2H), 4.23 (s, 2H), 6.43 (d, J=8.7 Hz, 1H), 6.79 (brs, 1H), 6.82 (dd, J=2.4, 8.7 Hz, 1H), 6.92 (brs, 1H), 7.12 (d, J=8.2 Hz, 2H), 7.25-7.40 (m, 8H). Melting Point 132-136° C., MS (ESI+) m/z 359.3 (M+1).

Example 56

Synthesis of 1-benzylindolin-5-yl 2-naphthylcarbamate

The title compound was synthesized from 1-benzylindolin-5-ol (15.0 mg, 66.6 µmol) using the same procedure employed for Example 2 (2), but with 2-naphthylisocyanate instead of 4-isopropylphenylisocyanate. The product was obtained as a white solid (14.4 mg, 55%) having the following characteristics.

$^1$H-NMR (CDCl$_3$) δ(ppm): 2.99 (t, J=8.2 Hz, 2H), 3.35 (t, J=8.2 Hz, 2H), 4.25 (s, 2H), 6.45 (d, J=8.7 Hz, 1H), 6.86 (dd, J=2.4, 8.7 Hz, 1H), 6.96 (brs, 1H), 7.02 (brs, 1H), 7.25-7.5 (m, 8H), 7.75-7.85 (m, 3H), 8.06 (brs, 1H). Melting Point 161-167° C., MS (ESI+) m/z 395.3 (M+1).

Example 57

Synthesis of 1-benzylindolin-5-yl ethylcarbamate

The title compound was synthesized from 1-benzylindolin-5-ol (15.0 mg, 66.6 µmol) using the same procedure employed for Example 2 (2), but with ethylisocyanate instead of 4-isopropylphenylisocyanate. The product was obtained having the following characteristics (12.4 mg, 63%).

MS (ESI+) m/z 297.3 (M+1).

Example 58

Synthesis of 1-(4-methoxycarbonylbenzyl)indolin-5-yl 4-isopropylphenylcarbamate

The title compound was synthesized using the same procedure employed for Example 23, but with methyl 4-formylbenzoate instead of 4-methoxybenzaldehyde. The product was obtained as a slightly yellow solid (15.8 mg, 70%) having the following characteristics. Melting Point 149-153° C., MS (ESI+) m/z 445.3 (M+1).

Example 59

Synthesis of 1-(2-naphthylmethyl)indolin-5-yl 4-isopropylphenylcarbamate

The title compound was synthesized using the same procedure employed for Example 23, but with 2-naphthaldehyde instead of 4-methoxybenzaldehyde. The product was obtained as a white solid (15.7 mg, 71%) having the following characteristics. Melting Point 136-140° C., MS (ESI+) m/z 437.3 (M+1).

Example 60

Synthesis of 1-(2-pyridylmethyl)indolin-5-yl 4-isopropylphenylcarbamate

The title compound was synthesized using the same procedure employed for Example 23, but with 2-pyridinecarboxyaldehyde instead of 4-methoxybenzaldehyde. The product was obtained as a white solid (11.4 mg, 58%) having the following characteristics. Melting Point 170-173° C., MS (ESI+) m/z 388.3 (M+1).

Example 61

Synthesis of 1-(2-furylmethyl)indolin-5-yl 4-isopropylphenylcarbamate

The title compound was synthesized using the same procedure employed for Example 23, but with furfural instead of 4-methoxybenzaldehyde. The product was obtained as a white solid (3.8 mg, 20%) having the following characteristics.

Melting Point 168-171° C., MS (ESI+) m/z 377.3 (M+1).

Example 62

Synthesis of 1-(3-hydroxybenzyl)indolin-5-yl 4-isopropylphenylcarbamate

The title compound was synthesized using the same procedure employed for Example 23, but with 3-hydroxybenzaldehyde instead of 4-methoxybenzaldehyde. The product was obtained as a white solid (19.0 mg, 93%) having the following characteristics. Melting Point 50-60° C., MS (ESI+) m/z 403.3 (M+1).

Example 63

Synthesis of 1-(4-dimethylamino-3-methoxybenzyl)indolin-5-yl 4-isopropylphenylcarbamate The title compound was synthesized using the same procedure employed for Example 23, but with 4-dimethylamino-3-methoxybenzaldehyde instead of 4-methoxybenzaldehyde. The product was obtained as a white solid (10.9 mg, 47%) having the following characteristics. Melting Point 152-153° C., MS (ESI+) m/z 460 (M+1).

Example 64

Synthesis of 1-(6-methoxy-2-naphthylmethyl)indolin-5-yl-4-isopropylphenylcarbamate The title compound was synthesized using the same procedure employed for Example 23, but with 6-methoxy-2-naphthaldehyde instead of 4-methoxybenzaldehyde. The product was obtained as a white solid (6.0 mg, 25%) having the following characteristics. Melting Point 151-153° C., MS (ESI+) m/z 467.4 (M+1).

Example 65

Synthesis of 1-[(pyrrol-2-yl)methyl]indolin-5-yl-4-isopropylphenylcarbamate

The title compound was synthesized using the same procedure employed for Example 23, but with pyrrole-2-carboxyaldehyde instead of 4-methoxybenzaldehyde. The product was obtained as a solid (15.9 mg, 84%) having the following characteristics. Melting Point 148-152° C., MS (ESI+) m/z 376.4 (M+1).

Example 66

Synthesis of 1-(2-hydroxybenzyl)indolin-5-yl 4-isopropylphenylcarbamate

The title compound was synthesized using the same procedure employed for Example 23, but with 2-hydroxybenzaldehyde instead of 4-methoxybenzaldehyde. The product was obtained as a white solid (17.0 mg, 83%) having the following characteristics. Melting Point 137-139° C., MS (ESI+) m/z 403.3 (M+1).

Example 67

Synthesis of 1-(4-hydroxy-3-methoxybenzyl)indolin-5-yl-4-isopropylphenylcarbamate The title compound was synthesized using the same procedure employed for Example 23, but with vanillin instead of 4-methoxybenzaldehyde. The product was obtained as a slightly brown solid (13.8 mg, 63%) having the following characteristics.
Melting Point 145-150° C., MS (ESI+) m/z 433.4 (M+1).

Example 68

Synthesis of 1-(3-hydroxy-4-methoxybenzyl)indolin-5-yl-4-isopropylphenylcarbamate The title compound was synthesized using the same procedure employed for Example 23, but with 3-hydroxy-4-methoxybenzaldehyde instead of 4-methoxybenzaldehyde. The product was obtained as a slightly yellow solid (13.1 mg, 60%) having the following characteristics. Melting Point 109-115° C., MS (ESI+) m/z 433.3 (M+1).

Example 69

Synthesis of 1-(3,5-dimethoxy-4-hydroxybenzyl) indolin-5-yl-4-isopropylphenylcarbamate The title compound was synthesized using the same procedure employed for Example 23, but with syringaldehyde instead of 4-methoxybenzaldehyde. The product was obtained as a yellow solid (23.2 mg, quant.) having the following characteristics.
Melting Point 144-149° C., MS (ESI+) m/z 463.4 (M+1).

Example 70

Synthesis of 1-[4-(3-dimethylaminopropoxy)benzyl)indolin-5-yl 4-isopropylphenylcarbamate The title compound was synthesized using the same procedure employed for Example 23, but with 4-(3-dimethylaminopropoxy)benzaldehyde instead of 4-methoxybenzaldehyde. The product was obtained as a yellow solid (20.6 mg, 83%) having the following characteristics.
MS (ESI+) m/z 488.4 (M+1).

Example 71

Synthesis of 1-(4-phenoxybenzyl)indolin-5-yl 4-isopropylphenylcarbamate

The title compound was synthesized using the same procedure employed for Example 23, but with 4-phenoxybenzaldehyde instead of 4-methoxybenzaldehyde. The product was obtained as a white solid (11.0 mg, 45%) having the following characteristics.
MS (ESI+) m/z 479.4 (M+1).

Example 72

Synthesis of 1-(3-phenoxybenzyl)indolin-5-yl 4-isopropyl phenylcarbamate

The title compound was synthesized using the same procedure employed for Example 23, but with 3-phenoxybenzaldehyde instead of 4-methoxybenzaldehyde. The product was obtained as a white solid (12.2 mg, 50%) having the following characteristics. Melting Point 142-143° C., MS (ESI+) m/z 479.4 (M+1).

Example 73

Synthesis of 1-(3-chloro-4-hydroxybenzyl)indolin-5-yl 4-isopropylphenylcarbamate The title compound was synthesized using the same procedure employed for Example 23, but with 3-chloro-4-hydroxybenzaldehyde instead of 4-methoxybenzaldehyde. The product was obtained as a white solid (8.2 mg, 37%) having the following characteristics. Melting Point 170-174° C., MS (ESI+) m/z 437.3 (M+1).

Example 74

Synthesis of 1-(4-dimethylamino-2-naphthylmethyl)indolin-5-yl 4-isopropylphenylcarbamate The title compound was synthesized using the same procedure employed for Example 23, but with 4-dimethylamino-2-naphthaldehyde instead of 4-methoxybenzaldehyde. The product was obtained as a white solid (17.8 mg, 73%) having the following characteristics. Melting Point 75-80° C., MS (ESI+) m/z 502.4 (M+Na).

Example 75

Synthesis of 1-(cyclohexylmethyl)indolin-5-yl 4-isopropylphenylcarbamate

The title compound was synthesized using the same procedure employed for Example 23, but with cyclohexanecarboxyaldehyde instead of 4-methoxybenzaldehyde. The product was obtained as a white solid (10.4 mg, 52%) having the following characteristics.
$^1$H-NMR (CDCl$_3$) δ(ppm): 0.95 (q, J=12 Hz, 2H), 1.1-1.4 (m, 9H), 1.5-1.9 (m, 6H), 2.81 (d, J=7.2 Hz, 1H), 2.88 (sep, J=6.8 Hz, 1H), 2.96 (t, J=8.2 Hz, 2H), 3.37 (t, J=8.2 Hz, 2H), 6.34 (d, J=8.7 Hz, 1H), 6.75-6.85 (m, 2H), 6.86 (brs, 1H), 7.18 (d, J=8.2 Hz, 2H), 7.35 (d, J=8.2 Hz, 2H). Melting Point 150-155° C., MS (ESI+) m/z 393.5 (M+1).

Example 76

Synthesis of 1-(quinolin-5-ylmethyl)indolin-5-yl 4-isopropylphenylcarbamate

The title compound was synthesized using the same procedure employed for Example 23, but with quinoline-5-carboxyaldehyde instead of 4-methoxybenzaldehyde. The product was obtained as a white solid (8.8 mg, 40%) having the following characteristics. Melting Point 195-199° C., MS (ESI+) m/z 438.4 (M+1).

Example 77

Synthesis of 1-(quinolin-2-ylmethyl)indolin-5-yl 4-isopropylphenylcarbamate

The title compound was synthesized using the same procedure employed for Example 23, but with quinoline-2-carboxyaldehyde instead of 4-methoxybenzaldehyde. The product was obtained as a slightly yellow solid (18.6 mg, 84%) having the following characteristics. Melting Point 150-152° C., MS (ESI+) m/z 438.3 (M+1).

Example 78

Synthesis of 1-(4-hydroxybenzyl)indolin-5-yl 4-isopropylphenylcarbamate

The title compound was synthesized using the same procedure employed for Example 23, but with 4-hydroxybenzaldehyde instead of 4-methoxybenzaldehyde. The product was obtained as a slightly yellow solid (18.5 mg, 91%) having the following characteristics.
MS (ESI+) m/z 403.3 (M+1).

Example 79

Synthesis of 1-(1-benzylindol-3-ylmethyl)indolin-5-yl-4-isopropylphenylcarbamate The title compound was synthesized using the same procedure employed for Example 23, but with 1-benzylindole-3-carboxyaldehyde instead of 4-methoxybenzaldehyde. The product was obtained as a white solid (16.1 mg, 62%) having the following characteristics.
Melting Point 170-172° C., MS (ESI+) m/z 538.5 (M+Na).

Example 80

Synthesis of 1-(indol-3-ylmethyl)indolin-5-yl 4-isopropylphenylcarbamate

The title compound was synthesized using the same procedure employed for Example 23, but with indole-3-carboxyaldehyde instead of 4-methoxybenzaldehyde. The product was obtained as a slightly yellow solid (12.5 mg, 58%) having the following characteristics. Melting Point 174-177° C., MS (ESI+) m/z 426.5 (M+1).

Example 81

Synthesis of 1-(1-methylindol-3-ylmethyl)indolin-5-yl-4-isopropylphenylcarbamate The title compound was synthesized using the same procedure employed for Example 23, but with 1-methylindole-3-carboxyaldehyde instead of 4-methoxybenzaldehyde. The product was obtained as a white solid (12.5 mg, 56%) having the following characteristics. Melting Point 162-167° C.

Example 82

Synthesis of 1-(indol-6-ylmethyl)indolin-5-yl 4-isopropylphenylcarbamate

The title compound was synthesized using the same procedure employed for Example 23, but with indole-6-carboxyaldehyde instead of 4-methoxybenzaldehyde. The product was obtained as a white solid (15.6 mg, 73%) having the following characteristics. Melting Point 194-196° C., MS (ESI+) m/z 426.5 (M+1).

Example 83

Synthesis of 1-(3-tetrahydrofurylmethyl)indolin-5-yl-4-isopropylphenylcarbamate

The title compound was synthesized using the same procedure employed for Example 23, but with tetrahydrofuran-3-carboxyaldehyde instead of 4-methoxybenzaldehyde. The

Example 84

Synthesis of 1-(quinolin-8-ylmethyl)indolin-5-yl-4-isopropylphenylcarbamate

The title compound was synthesized using the same procedure employed for Example 23, but with quinoline-8-carboxyaldehyde instead of 4-methoxybenzaldehyde. The product was obtained as a slightly yellow solid (18.3 mg, 83%) having the following characteristics. Melting Point 181-183° C., MS (ESI+) m/z 438.4 (M+1).

Example 85

Synthesis of 1-benzylindolin-5-yl 5-indanylcarbamate

The title compound was synthesized from 1-benzylindolin-5-ol (15.0 mg, 66.6 μmol) using the same procedure employed for Example 2 (2), but with 5-indanylisocyanate instead of 4-isopropylphenylisocyanate. The product was obtained as a solid (14.3 mg, 75%) having the following characteristics.
MS (ESI+) m/z 385.5 (M+1).

Example 86

Synthesis of 1-benzylindolin-5-yl-4-(ethoxycarbonyl)phenylcarbamate

The title compound was synthesized using the same procedure employed for Example 31, but with ethyl 4-aminobenzoate instead of 4-methoxybenzylamine. The product was obtained as a white solid (4.0 mg, 14%) having the following characteristics.
$^1$H-NMR (CDCl$_3$) δ(ppm): 1.39 (t, J=7.2 Hz, 3H), 2.98 (t, J=8.2 Hz, 2H), 3.35 (t, J=8.2 Hz, 2H), 4.24 (s, 2H), 4.36 (q, J=7.2 Hz, 2H), 6.43 (d, J=8.7 Hz, 1H), 6.82 (dd, J=2.4, 8.7 Hz, 1H), 6.92 (d, J=2.4 Hz, 1H), 7.06 (brs, 1H), 7.25-7.4 (m, 5H), 7.51 (d, J=8.7 Hz, 2H), 8.02 (d, J=8.7 Hz, 2H). Melting Point 167-170° C., MS (ESI+) m/z 417.4 (M+1).

Example 87

Synthesis of 1-benzylindolin-5-yl 3-methoxyphenylcarbamate

The title compound was synthesized using the same procedure employed for Example 31, but with m-anisidine instead of 4-methoxybenzylamine. The product was obtained as a sticky oil (2.0 mg, 8%) having the following characteristics.
$^1$H-NMR (CDCl$_3$) δ(ppm): 2.98 (t, J=8.2 Hz, 2H), 3.34 (t, J=8.2 Hz, 2H), 3.80 (s, 3H), 4.23 (s, 2H), 6.44 (d, J=8.2 Hz, 1H), 6.64 (dd, J=2.4, 8.2 Hz, 1H), 6.82 (dd, J=2.4, 8.2 Hz, 1H), 6.85-6.95 (m, 3H), 7.2-7.4 (m, 7H).
MS (ESI+) m/z 375.4 (M+1).

Example 88

Synthesis of 1-benzylindolin-5-yl 3-methylthiophenylcarbamate

The title compound was synthesized using the same procedure employed for Example 31, but with 3-methylthioaniline instead of 4-methoxybenzylamine. The product was obtained as a sticky oil (2.5 mg, 10%) having the following characteristics.
MS (ESI+) m/z 391.3 (M+1).

Example 89

Synthesis of 1-benzylindolin-5-yl 3-bromophenylcarbamate

The title compound was synthesized using the same procedure employed for Example 31, but with 3-bromoaniline instead of 4-methoxybenzylamine. The product was obtained as a sticky oil (1.0 mg, 4%) having the following characteristics.
MS (ESI+) m/z 423.3 (M+1).

Example 90

Synthesis of 1-benzylindolin-5-yl 2-cyanophenylcarbamate

The title compound was synthesized using the same procedure employed for Example 31, but with 2-cyanoaniline instead of 4-methoxybenzylamine. The product was obtained as a solid (2.2 mg, 9%) having the following characteristics.
MS (ESI+) m/z 370.3 (M+1).

Example 91

Synthesis of 1-benzylindolin-5-yl-4-methylphenethylcarbamate

The title compound was synthesized using the same procedure employed for Example 31, but with 4-methylphenethylamine instead of 4-methoxybenzylamine. The product was obtained as a white solid (10.4 mg, 40%) having the following characteristics.
MS (ESI+) m/z 387.4 (M+1)

Example 92

Synthesis of 1-benzylindolin-5-yl quinolin-6-ylcarbamate

The title compound was synthesized using the same procedure employed for Example 31, but with 6-aminoquinoline instead of 4-methoxybenzylamine. The product was obtained as a white solid (4.4 mg, 17%) having the following characteristics.
MS (ESI+) m/z 396.4 (M+1).

Example 93

Synthesis of 1-benzylindolin-5-yl 4-cyclohexylphenylcarbamate

The title compound was synthesized using the same procedure employed for Example 31, but with 4-cyclohexylaniline instead of 4-methoxybenzylamine. The product was obtained as a white solid (6.9 mg, 24%) having the following characteristics.
Melting Point 171-174° C., MS (ESI+) m/z 427.5 (M+1).

Example 94

Synthesis of 1-benzylindolin-5-yl 2-(1,2,2,6,6-pentamethylpiperidin-4-yl)ethylcarbamate The title compound was synthesized using the same procedure employed for Example 31, but with 4-(2-aminoethyl)-1,2,2,6,6-pentamethylpiperidine instead of 4-methoxybenzylamine. The product was obtained as a white solid (1.0 mg, 3%) having the following characteristics.
MS (ESI+) m/z 449.4 (M+1).

Example 95

Synthesis of 1-benzylindolin-5-yl pyridin-4-ylcarbamate

The title compound was synthesized using the same procedure employed for Example 31, but with 4-aminopyridine instead of 4-methoxybenzylamine. The product was obtained as a white solid (8.6 mg, 37%) having the following characteristics.
$^1$H-NMR (CDCl$_3$) δ(ppm): 2.98 (t, J=8.2 Hz, 2H), 3.36 (t, J=8.2 Hz, 2H), 4.24 (s, 2H), 6.43 (d, J=8.2 Hz, 1H), 6.81 (dd, J=1.9, 8.2 Hz, 1H), 6.91 (brs, 1H), 7.17 (brs, 1H), 7.25-7.38 (m, 5H), 7.39 (d, J=6.3 Hz, 2H), 8.50 (d, J=6.3 Hz, 2H), 1.23 (d, J=6.8 Hz, 6H), 2.88 (sep, J=6.8 Hz, 1H), 3.04 (t, J=8.7 Hz, 2H), 3.34 (t, J=8.7 Hz, 2H), 6.60 (d, J=8.2 Hz, 1H), 6.79 (dd, J=1.9, 8.2 Hz, 1H), 6.94 (brs, 1H), 7.18 (d, J=8.2 Hz, 2H), 7.35 (d, J=8.2 Hz, 2H). Melting Point 132-136° C., MS (ESI+) m/z 346.4 (M+1).

Example 96

Synthesis of 1-benzylindolin-5-yl-1,2,3,4-tetrahydronaphthalen-1-ylcarbamate

The title compound was synthesized using the same procedure employed for Example 31, but with 1,2,3,4-tetrahydronaphthylamine instead of 4-methoxybenzylamine. The product was obtained as a white solid (8.8 mg, 33%) having the following characteristics.
MS (ESI+) m/z 399.4 (M+1).

Example 97

Synthesis of 1-benzylindolin-5-yl 1-(p-tolyl)ethylcarbamate

The title compound was synthesized using the same procedure employed for Example 31, but with 1-(p-tolyl)ethylamine instead of 4-methoxybenzylamine. The product was obtained as a white solid (6.1 mg, 24%) having the following characteristics.
MS (ESI+) m/z 387.4 (M+1).

Example 98

Synthesis of 1-benzylindolin-5-yl 2-thiophenemethylcarbamate

The title compound was synthesized using the same procedure employed for Example 31, but with 2-thiophenemethyamine instead of 4-methoxybenzylamine. The product was obtained as a white solid (5.0 mg, 21%) having the following characteristics.
MS (ESI+) m/z 365.3 (M+1).

Example 99

Synthesis of 1-benzylindolin-5-yl-4-methylbenzylcarbamate

The title compound was synthesized using the same procedure employed for Example 31, but with 4-methylbenzylamine instead of 4-methoxybenzylamine. The product was obtained as a white solid (9.8 mg, 40%) having the following characteristics.
MS (ESI+) m/z 373.4 (M+1).

Example 100

Synthesis of 1-benzylindolin-5-yl 3-methoxybenzylcarbamate

The title compound was synthesized using the same procedure employed for Example 31, but with 3-methoxybenzylamine instead of 4-methoxybenzylamine. The product was obtained as a sticky oil (10.2 mg, 39%) having the following characteristics.
MS (ESI+) m/z 389.4 (M+1).

Example 101

Synthesis of 1-benzylindolin-5-yl 2,4-dimethoxybenzylcarbamate

The title compound was synthesized using the same procedure employed for Example 31, but with 2,4-dimethoxybenzylamine instead of 4-methoxybenzylamine. The product was obtained as a white solid (10.5 mg, 38%) having the following characteristics.
MS (ESI+) m/z 419.4 (M+1).

Example 102

Synthesis of 1-benzylindolin-5-yl 2-pyridylmethylcarbamate

The title compound was synthesized using the same procedure employed for Example 31, but with 2-(aminomethyl)pyridine instead of 4-methoxybenzylamine. The product was obtained as a slightly brown solid (8.5 mg, 36%) having the following characteristics.
MS (ESI+) m/z 360.4 (M+1).

Example 103

Synthesis of 1-benzylindolin-5-yl 4-pyridylmethylcarbamate

The title compound was synthesized using the same procedure employed for Example 31, but with 4-(aminomethyl)pyridine instead of 4-methoxybenzylamine. The product was obtained as a white solid (9.8 mg, 41%) having the following characteristics.
MS (ESI+) m/z 360.4 (M+1).

Example 104

Synthesis of 1-benzylindolin-5-yl 4-chlorophenethylcarbamate

The title compound was synthesized using the same procedure employed for Example 31, but with 4-chlorophenethylamine instead of 4-methoxybenzylamine. The product was obtained as a sticky oil (4.3 mg, 16%) having the following characteristics.
MS (ESI+) m/z 407.3 (M+1).

Example 105

Synthesis of 1-benzylindolin-5-yl 3-trifluoromethylphenylcarbamate

The title compound was synthesized from 1-benzylindolin-5-ol (15.0 mg, 66.6 μmol) using the same procedure employed for Example 1 (2), but with 3-trifluoromethylphenylisocyanate instead of 4-isopropylphenylisocyanate. The product was obtained as a sticky oil (1.2 mg, 4%) having the following characteristics.
MS (ESI+) m/z 413.3 (M+1).

Example 106

Synthesis of 1-benzylindolin-5-yl-4-n-butylphenylcarbamate

The title compound was synthesized from 1-benzylindolin-5-ol (15.0 mg, 66.6 μmol) using the same procedure employed for Example 1 (2), but with 4-n-butylphenylisocyanate instead of 4-isopropylphenylisocyanate. The product was obtained as a white solid (5.6 mg, 21%) having the following characteristics.
$^1$H-NMR (CDCl$_3$) δ(ppm): 0.92 (t, J=7.2 Hz, 3H), 1.3-1.4 (m, 2H), 1.5-1.7 (m, 2H), 2.57 (t, J=7.7 Hz, 6H), 2.97 (t, J=8.2 Hz, 2H), 3.34 (t, J=8.2 Hz, 2H), 4.23 (s, 2H), 6.43 (d, J=8.2 Hz, 1H), 6.75-6.85 (m, 2H), 6.92 (s, 1H), 7.13 (d, J=8.2 Hz, 2H), 7.25-7.40 (m, 6H). Melting Point 131-134° C., MS (ESI+) m/z 401.4 (M+1).

Example 107

Synthesis of 1-benzylindolin-5-yl-4-n-hexyloxyphenylcarbamate

The title compound was synthesized from 1-benzylindolin-5-ol (15.0 mg, 66.6 μmol) using the same procedure employed for Example 1 (2), but with 4-n-hexyloxyphenylisocyanate instead of 4-isopropylphenylisocyanate. The product was obtained as a solid (1.3 mg, 4%) having the following characteristics.
$^1$H-NMR (CDCl$_3$) δ(ppm): 0.85-0.95 (m, 3H), 1.3-1.4 (m, 4H), 1.42-1.5 (m, 2H), 1.7-1.82 (m, 2H), 2.97 (t, J=8.2 Hz, 2H), 3.34 (t, J=8.2 Hz, 2H), 3.93 (t, J=6.8 Hz, 2H), 4.23 (s, 2H), 6.43 (d, J=8.7 Hz, 1H), 6.8-6.95 (m, 3H), 7.25-7.38 (m, 9H). Melting Point 138-142° C., MS (ESI+) m/z 445.5 (M+1).

Example 108

Synthesis of 1-benzylindolin-5-yl 4-phenylphenylcarbamate

The title compound was synthesized from 1-benzylindolin-5-ol (15.0 mg, 66.6 μmol) using the same procedure employed for Example 1 (2), but with 4-phenylphenylisocyanate instead of 4-isopropylphenylisocyanate. The product was obtained as a white solid (0.9 mg, 3%) having the following characteristics.
$^1$H-NMR (CDCl$_3$) δ(ppm): 2.96 (t, J=8.2 Hz, 2H), 3.35 (t, J=8.2 Hz, 2H), 4.24 (s, 2H), 6.44 (d, J=8.2 Hz, 1H), 6.84 (dd, J=1.9, 8.2 Hz, 1H), 6.94 (m, 2H), 7.25-7.48 (m, 8H), 7.52 (d, J=8.2 Hz, 2H), 7.55-7.60 (m, 4H). Melting Point 175-178° C., MS (ESI+) m/z 421.4 (M+1).

Example 109

Synthesis of 1-benzylindolin-5-yl-4-acetylphenylcarbamate

The title compound was synthesized from 1-benzylindolin-5-ol (15.0 mg, 66.6 μmol) using the same procedure employed for Example 1 (2), but with 4-acetylphenylisocyanate instead of 4-isopropylphenylisocyanate. The product was obtained as a solid (0.4 mg, 2%) having the following characteristics.
$^1$H-NMR (CDCl$_3$) δ(ppm): 2.58 (s, 3H), 2.99 (t, J=8.2 Hz, 2H), 3.36 (t, J=8.2 Hz, 2H), 4.24 (s, 2H), 6.43 (d, J=8.7 Hz, 1H), 6.82 (dd, J=2.4, 8.7 Hz, 1H), 6.92 (brs, 1H), 7.05 (brs, 1H), 7.2-7.4 (m, 5H), 7.54 (d, J=8.7 Hz, 2H), 7.96 (d, J=8.7 Hz, 2H). Melting Point 186-196° C., MS (ESI+) m/z 387.4 (M+1).

Example 110

Synthesis of 1-benzylindolin-5-yl phenylcarbamate

The title compound was synthesized from 1-benzylindolin-5-ol (15.0 mg, 66.6 μmol) using the same procedure employed for Example 2 (2), but with phenylisocyanate instead of 4-isopropylphenylisocyanate. The product was obtained as a white solid (7.3 mg, 32%) having the following characteristics.
$^1$H-NMR (CDCl$_3$) δ(ppm): 2.98 (t, J=8.2 Hz, 2H), 3.34 (t, J=8.2 Hz, 2H), 4.23 (s, 2H), 6.43 (d, J=8.7 Hz, 1H), 6.83 (dd, J=2.4, 8.7 Hz, 1H), 6.86 (brs, 1H), 6.92 (brs, 1H), 7.09 (t, J=7.7 Hz, 1H), 7.25-7.40 (m, 7H), 7.44 (d, J=7.7 Hz, 2H). Melting Point 105-112° C., MS (ESI+) m/z 345.3 (M+1).

Example 111

Synthesis of 1-benzylindolin-5-yl-4-chlorophenylcarbamate

The title compound was synthesized from 1-benzylindolin-5-ol (15.0 mg, 66.6 μmol) using the same procedure employed for Example 1 (2), but with 4-chlorophenylisocyanate instead of 4-isopropylphenylisocyanate. The product was obtained as a slightly brown solid (2.0 mg, 8%) having the following characteristics.
$^1$H-NMR (CDCl$_3$) δ(ppm): 2.97 (t, J=8.2 Hz, 2H), 3.35 (t, J=8.2 Hz, 2H), 4.23 (s, 2H), 6.43 (d, J=8.7 Hz, 1H), 6.81 (dd, J=2.4, 8.7 Hz, 1H), 6.87 (brs, 1H), 6.91 (d, J=2.4 Hz, 1H), 7.25-7.45 (m, 7H), 7.45 (d, J=8.7 Hz, 2H). Melting Point 188-193° C., MS (ESI+) m/z 379.4 (M+1).

Example 112

Synthesis of 1-benzylindolin-5-yl-4-(1H-pyrrol-1-yl) phenylcarbamate

The title compound was synthesized from 1-benzylindolin-5-ol (15.0 mg, 66.6 μmol) using the same procedure employed for Example 1 (2), but with 1-(4-isocyanatephenyl)-1H-pyrrole instead of 4-isopropylphenylisocyanate. The product was obtained as a solid (2.4 mg, 9%) having the following characteristics.
MS (ESI+) m/z 410.5 (M+1).

Example 113

Synthesis of 1-benzylindolin-5-yl 3,4-dimethylphenylcarbamate

The title compound was synthesized from 1-benzylindolin-5-ol (15.0 mg, 66.6 µmol) using the same procedure employed for Example 2 (2), but with 3,4-dimethylphenylisocyanate instead of 4-isopropylphenylisocyanate. The product was obtained as a sticky oil (10.5 mg, 42%) having the following characteristics.
MS (ESI+) m/z 373.4 (M+1).

Example 114

Synthesis of 1-benzylindolin-5-yl n-propylcarbamate

The title compound was synthesized from 1-benzylindolin-5-ol (15.0 mg, 66.6 µmol) using the same procedure employed for Example 2 (2), but with n-propylisocyanate instead of 4-isopropylphenylisocyanate. The product was obtained as a white solid (12.3 mg, 60%) having the following characteristics.
MS (ESI+) m/z 311.4 (M+1).

Example 115

Synthesis of 1-benzylindolin-5-yl 2-methylphenethylcarbamate

The title compound was synthesized using the same procedure employed for Example 31, but with 2-methylphenethylamine instead of 4-methoxybenzylamine. The product was obtained as a sticky oil (4.4 mg, 17%) having the following characteristics.
MS (ESI+) m/z 387.4 (M+1).

Example 116

Synthesis of 1-benzylindolin-5-yl 2,4-dimethylphenethylcarbamate

The title compound was synthesized using the same procedure employed for Example 31, but with 2,4-dimethylphenethylamine instead of 4-methoxybenzylamine. The product was obtained as a white solid (6.7 mg, 25%) having the following characteristics.
MS (ESI+) m/z 401.5 (M+1).

Example 117

Synthesis of 1-benzylindolin-5-yl 2-methoxyphenethylcarbamate

The title compound was synthesized using the same procedure employed for Example 31, but with 2-methoxyphenethylamine instead of 4-methoxybenzylamine. The product was obtained as a white solid (9.2 mg, 34%) having the following characteristics.
MS (ESI+) m/z 403.5 (M+1).

Example 118

Synthesis of 1-benzylindolin-5-yl 2,4-dichlorophenethylcarbamate

The title compound was synthesized using the same procedure employed for Example 31, but with 2,4-dichlorophenethylamine instead of 4-methoxybenzylamine. The product was obtained as a white solid (5.6 mg, 19%) having the following characteristics.
MS (ESI+) m/z 441.3 (M+1).

Example 119

Synthesis of 1-benzylindolin-5-yl 2-(4-pyridyl)ethylcarbamate

The title compound was synthesized using the same procedure employed for Example 31, but with 2-(4-pyridyl)ethylamine instead of 4-methoxybenzylamine. The product was obtained as a sticky oil (8.7 mg, 35%) having the following characteristics.
MS (ESI+) m/z 374.4 (M+1).

Example 120

Synthesis of 1-benzylindolin-5-yl 2-(3-pyridyl)ethylcarbamate

The title compound was synthesized using the same procedure employed for Example 31, but with 2-(3-pyridyl)ethylamine instead of 4-methoxybenzylamine. The product was obtained as a sticky oil (10.2 mg, 41%) having the following characteristics.
MS (ESI+) m/z 374.4 (M+1).

Example 121

Synthesis of 1-benzylindolin-5-yl 2-(piperidin-1-yl)ethylcarbamate

The title compound was synthesized using the same procedure employed for Example 31, but with 1-(2-aminoethyl)piperidine instead of 4-methoxybenzylamine. The product was obtained as a white solid (11.7 mg, 46%) having the following characteristics.
MS (ESI+) m/z 380A (M+1).

Example 122

Synthesis of 1-benzylindolin-5-yl (2,5-dihydro-2,5-dimethoxyfuran-2-yl)methylcarbamate The title compound was synthesized using the same procedure employed for Example 31, but with 2,5-dihydro-2,5-dimethoxyfurfurylamine instead of 4-methoxybenzylamine. The product was obtained as a sticky oil (8.6 mg, 31%) having the following characteristics.
MS (ESI+) m/z 411.4 (M+1).

Example 123

Synthesis of indolin-5-yl phenylcarbamate

To a solution of 1-benzylindolin-5-yl phenylcarbamate (30 mg, 87 µmol) in 3.0 mL of isopropylalcohol was added palladium hydroxide 10% on carbon (60 mg) under nitrogen. After the vessel was purged with hydrogen, the reaction mixture was stirred under 1 atm of hydrogen at room temperature for 3 h. After the vessel was purged with nitrogen, the reaction mixture was filtered to remove palladium hydroxide 10% on carbon. The filtrate was concentrated in vacuo, and the residue was purified by silica gel column chromatography (hexane/ethyl acetate=85/15 to 40/60) to obtain the title compound as a white solid (11.5 mg, 52%).
MS (ESI+) m/z 255.4 (M+1).

Example 124

Synthesis of indolin-5-yl 4-dimethylaminophenylcarbamate

The title compound was synthesized from 1-benzylindolin-5-yl 4-dimethylaminophenylcarbamate (30 mg, 77 μmol) using the same procedure employed for Example 123 (silica gel column chromatography: chloroform/methanol=99/1 to 90/10). The product was obtained as a white solid (4.0 mg, 17%) having the following characteristics.
MS (ESI+) m/z 298.5 (M+1).

Example 125

Synthesis of indolin-5-yl (S)-1-(1-naphthyl)ethylcarbamate

The title compound was synthesized from 1-benzylindolin-5-yl (S)-1-(1-naphthyl)ethylcarbamate (27.2 mg, 64.4 μmol) using the same procedure employed for Example 123. The product was obtained as a white solid (6.2 mg, 29%) having the following characteristics.
MS (ESI+) m/z 333.3 (M+1).

Example 126

Synthesis of indolin-5-yl cyclohexylcarbamate

The title compound was synthesized from 1-benzylindolin-5-yl cyclohexylcarbamate (48.0 mg, 137 μmol) using the same procedure employed for Example 123. The product was obtained as a white solid (10.6 mg, 30%) having the following characteristics.
MS (ESI+) m/z 261.5 (M+1).

Example 127

Synthesis of indolin-5-yl benzylcarbamate

The title compound was synthesized from 1-benzylindolin-5-yl benzylcarbamate (41.8 mg, 117 μmol) using the same procedure employed for Example 123. The product was obtained as a white solid (5.8 mg, 18%) having the following characteristics.
$^1$H-NMR (CDCl$_3$) δ(ppm): 3.02 (t, J=8.2 Hz, 2H), 3.57 (t, J=8.2 Hz, 2H), 4.45 (d, J=5.8 Hz, 2H), 5.25 (brs, 1H), 6.58 (d, J=8.7 Hz, 1H), 6.76 (dd, J=2.4, 8.7 Hz, 1H), 6.90 (brs, 1H), 7.25-7.4 (m, 5H). Melting Point 95-99° C., MS (ESI+) m/z 269.5 (M+1).

Example 128

Synthesis of indolin-5-yl phenethylcarbamate

The title compound was synthesized from 1-benzylindolin-5-yl phenethylcarbamate (26.9 mg, 72.2 μmol) using the same procedure employed for Example 123. The product was obtained as a white solid (4.8 mg, 24%) having the following characteristics.
MS (ESI+) m/z 283.4 (M+1).

Example 129

Synthesis of indolin-5-yl methylcarbamate

The title compound was synthesized from 1-benzylindolin-5-yl methylcarbamate (43.8 mg, 155 μmol) using the same procedure employed for Example 123. The product was obtained having the following characteristics (4.9 mg, 16%).
$^1$H-NMR (CDCl$_3$) δ(ppm): 2.91 (d, J=4.8 Hz, 3H), 3.01 (t, J=8.2 Hz, 2H), 3.56 (t, J=8.2 Hz, 2H), 5.0-5.1 (brs, 1H), 6.56 (d, J=8.7 Hz, 1H), 6.72 (dd, J=2.4, 8.7 Hz, 1H), 6.87 (brs, 1H). Melting Point 109-112° C., MS (ESI+) m/z 193.5 (M+1).

Example 130

Synthesis of indolin-5-yl ethylcarbamate

The title compound was synthesized from 1-benzylindolin-5-yl ethylcarbamate (47.7 mg, 161 μmol) using the same procedure employed for Example 123. The product was obtained as a white solid (4.0 mg, 12%) having the following characteristics.
MS (ESI+) m/z 207 (M+1).

Example 131

Synthesis of 1-benzylindolin-5-yl methylcarbamate

The title compound was synthesized from 1-benzylindolin-5-ol (55.8 mg, 0.248 mmol) using the same procedure employed for Example 2 (2), but with methylisocyanate instead of 4-isopropylphenylisocyanate. The product was obtained as a white solid (43.8 mg, 63%) having the following characteristics.
$^1$H-NMR (CDCl$_3$) δ(ppm): 2.88 (d, J=4.8 Hz, 3H), 2.95 (t, J=8.2 Hz, 2H), 3.31 (t, J=8.2 Hz, 2H), 4.21 (s, 2H), 4.86 (brs, 1H), 6.40 (d, J=8.2 Hz, 1H), 6.76 (d, J=8.2 Hz, 1H), 6.85 (d, J=8.2 Hz, 1H), 7.25-7.4 (m, 5H). Melting Point 77-80° C., MS (ESI+) m/z 283.4 (M+1).

Example 132

Synthesis of indolin-5-yl (S)-1-phenylethylcarbamate

The title compound was synthesized from 1-benzylindolin-5-yl (S)-1-phenylethylcarbamate (36 mg, 97 μmol) using the same procedure employed for Example 123. The product was obtained as a white solid (8.3 mg, 30%) having the following characteristics.
MS (ESI+) m/z 283.4 (M+1).

Example 133

Synthesis of 1-benzylindolin-5-yl 4-dimethylaminophenylcarbamate

The title compound was synthesized from 1-benzylindolin-5-ol (45.0 mg, 0.200 mmol) using the same procedure employed for Example 2 (2), but with 4-dimethylaminophenylisocyanate instead of 4-isopropylphenylisocyanate. The product was obtained as a slightly brown solid (34.8 mg, 45%) having the following characteristics.

$^1$H-NMR (CDCl$_3$) δ(ppm): 2.92 (s, 6H), 2.97 (t, J=8.2 Hz, 2H), 3.33 (t, J=8.2 Hz, 2H), 4.22 (s, 2H), 6.43 (d, J=8.7 Hz, 1H), 6.67 (brs, 1H), 6.72 (d, J=8.7 Hz, 2H), 6.82 (dd, J=2.4, 8.7 Hz, 1H), 6.92 (brs, 1H), 7.25-7.4 (m, 7H). Melting Point 134-139° C., MS (ESI+) m/z 388.4 (M+1).

Example 134

Synthesis of 1-benzylindolin-5-yl 4-tert-butylphenylcarbamate

The title compound was synthesized from 1-benzylindolin-5-ol (50.0 mg, 0.222 mmol) using the same procedure employed for Example 2 (2), but with 4-tert-butylphenylisocyanate instead of 4-isopropylphenylisocyanate. The product was obtained as a white solid (34.1 mg, 38%) having the following characteristics.

$^1$H-NMR (CDCl$_3$) δ(ppm): 1.31 (s, 9H), 2.97 (t, J=8.2 Hz, 2H), 3.34 (t, J=8.2 Hz, 2H), 4.23 (s, 2H), 6.43 (d, J=8.7 Hz, 1H), 6.78-6.82 (brs, 1H), 6.82 (dd, J=2.4, 8.7 Hz, 1H), 6.92 (d, J=2.4 Hz, 1H), 7.26-7.40 (m, 9H). Melting Point 175-178° C., MS (ESI+) m/z 401.4 (M+1).

Example 135

Synthesis of indolin-5-yl 4-tert-butylphenylcarbamate

The title compound was synthesized from 1-benzylindolin-5-yl 4-tert-butylphenylcarbamate (30 mg, 75 μmol) using the same procedure employed for Example 123. The product was obtained as a white solid (8.4 mg, 36%) having the following characteristics.

MS (ESI+) m/z 311.4 (M+1).

Example 136

Synthesis of 1-benzylindolin-5-yl 2-(dimethylamino)ethylcarbamate

The title compound was synthesized from 1-benzylindolin-5-ol (25.0 mg, 111 μmol) using the same procedure employed for Example 31, but with 2-(dimethylamino)ethylamine instead of 4-methoxybenzylamine. The product was obtained as a white solid (11.0 mg, 29%) having the following characteristics.

MS (ESI+) m/z 340.5 (M+1).

Example 137

Synthesis of 1-benzylindolin-5-yl 3-(dimethylamino)propylcarbamate

The title compound was synthesized from 1-benzylindolin-5-ol (25.0 mg, 111 μmol) using the same procedure employed for Example 31, but with 3-(dimethylamino)propylamine instead of 4-methoxybenzylamine. The product was obtained as a white solid (21.5 mg, 55%) having the following characteristics.

MS (ESI+) m/z 354.5 (M+1).

Example 138

Synthesis of 1-benzylindolin-5-yl 1-benzylpiperidin-4-ylcarbamate

The title compound was synthesized from 1-benzylindolin-5-ol (25.0 mg, 111 μmol) using the same procedure employed for Example 31, but with 1-benzylpiperidin-4-ylamine instead of 4-methoxybenzylamine. The product was obtained as a white solid (16.5 mg, 34%) having the following characteristics.

MS (ESI+) m/z 442.5 (M+1).

Example 139

Synthesis of 1-benzylindolin-5-yl 2-(1-benzylpiperidin-4-yl)ethylcarbamate

The title compound was synthesized from 1-benzylindolin-5-ol (25.0 mg, 111 μmol) using the same procedure employed for Example 31, but with 2-(1-benzylpiperidin-4-yl)ethylamine instead of 4-methoxybenzylamine. The product was obtained as a slightly yellow solid (15.5 mg, 30%) having the following characteristics.

MS (ESI+) m/z 470.6 (M+1).

Example 140

Synthesis of 1-benzylindolin-5-yl 3,4-dimethoxyphenylcarbamate

The title compound was synthesized from 1-benzylindolin-5-ol (30.0 mg, 0.133 mmol) using the same procedure employed for Example 2 (2), but with 3,4-dimethoxyphenylisocyanate instead of 4-isopropylphenylisocyanate. The product was obtained as a white solid (26.9 mg, 50%) having the following characteristics.

$^1$H-NMR (CDCl$_3$) δ(ppm): 2.97 (t, J=8.2 Hz, 2H), 3.34 (t, J=8.2 Hz, 2H), 3.86 (s, 3H), 3.87 (s, 3H), 4.23 (s, 2H), 6.43 (d, J=8.7 Hz, 1H), 6.74-6.84 (m, 4H), 6.91 (s, 1H), 7.26-7.38 (m, 6H). Melting Point 51-56° C., MS (ESI+) m/z 405.3 (M+1).

Example 141

Synthesis of indolin-5-yl-4-methoxyphenylcarbamate

The title compound was synthesized from 1-benzylindolin-5-yl 4-methoxyphenylcarbamate (20 mg, 53 μmol) using the same procedure employed for Example 123. The product was obtained as a white solid (4.8 mg, 32%) having the following characteristics. Melting Point 220-224° C., MS (ESI+) m/z 285.2 (M+1).

Example 142

Synthesis of indolin-5-yl 3,4-dimethoxyphenylcarbamate

The title compound was synthesized from 1-benzylindolin-5-yl 3,4-dimethoxyphenylcarbamate (26.9 mg, 65.5 μmol) using the same procedure employed for Example 123. The product was obtained as a white solid (1.4 mg, 7%) having the following characteristics. Melting Point 140-144° C., MS (ESI+) m/z 315.3 (M+1).

Example 143

Synthesis of indolin-5-yl cyclohexylmethylcarbamate

The title compound was synthesized from 1-benzylindolin-5-yl cyclohexylmethylcarbamate (81.5 mg, 0.224 mmol) using the same procedure employed for Example 22. The

Example 144

Synthesis of indolin-5-yl 4-methoxyphenylcarbamate

The title compound was synthesized from 1-benzylindolin-5-yl 4-methoxyphenylcarbamate (79.0 mg, 0.224 mmol) using the same procedure employed for Example 22. The product was obtained as a slightly yellow solid (45.2 mg, 77%) having the following characteristics. Melting Point 79-82° C., MS (ESI+) m/z 263.3 (M+1).

Example 145

Synthesis of 1-benzyl-3,3-dimethylindolin-5-yl-4-isopropylphenylcarbamate (1) Synthesis of N-(4-methoxyphenyl)-N-(2-methylallyl)acetamide To a solution of p-acetanisidide (1.00 g, 6.05 mmol), potassium carbonate (0.92 g, 6.7 mmol), sodium hydroxide (0.27 g, 6.8 mmol) and tetra-n-butylammoniumbromide (0.39 g, 1.2 mmol) in 10 mL of toluene was added 3-chloro-2-methyl-1-propene (0.71 mL, 7.3 mmol) at room temperature. After the reaction mixture was stirred at 75° C. for 4 h, the reaction mixture was cooled to room temperature, and was diluted with ethyl acetate. The solution was washed with water, 3 M HCl, saturated NaHCO$_3$ aqueous solution and brine, successively, and dried over MgSO$_4$. After filtration, the filtrate was concentrated in vacuo, and the residue was purified by silica gel column chromatography (hexane/ethyl acetate=80/20 to 60/40) to obtain the title compound (1.26 g, 95%).

(2) Synthesis of 1-acetyl-3,3-dimethylindolin-5-ol

A solution of N-(4-methoxyphenyl)-N-(2-methylallyl)acetamide (1.00 g, 4.56 mmol) and aluminium chloride (2.0 g, 15.0 mmol) in 1.0 mL of chlorobenzene was stirred at 110° C. for 3 h. After the reaction mixture was cooled to 0° C., the reaction mixture was diluted with water and ethyl acetate. The separated organic layer was washed with 1 M HCl, saturated NaHCO$_3$ aqueous solution and brine, successively, and dried over MgSO$_4$. After filtration, the filtrate was concentrated in vacuo, and the residue was purified by silica gel column chromatography (hexane/ethyl acetate=70/30 to 20/80) to obtain the title compound (0.31 g, 33%), and followed by recrystallization (hexane/ethyl acetate) to obtain the title compound (0.17 g) as a white solid.

(3) Synthesis of 1-benzyl-3,3-dimethylindolin-5-ol

A solution of 1-acetyl-3,3-dimethylindolin-5-ol (150 mg, 0.73 mmol) in 1.5 mL of 6 M HCl was stirred at 105° C. for 17 h. After the reaction mixture was diluted with toluene, the separated aqueous layer was neutralized by saturated NaHCO$_3$ aqueous solution, and extracted with ethyl acetate. The extract was washed with brine, and dried over MgSO$_4$. After filtration, the filtrate was concentrated in vacuo to obtain crude 3,3-dimethylindolin-5-ol (128 mg). To a solution of the above product in a 1:1 solution (2.0 mL) of acetic acid and tetrahydrofuran was added benzaldehyde (0.15 mL, 0.15 mmol) at room temperature. After being stirred at the same temperature for 1 h, sodium cyanoborohydride (10.4 mg, 0.165 mmol) was added with additional stirring for 1 h. After the reaction mixture was neutralized by saturated NaHCO$_3$ aqueous solution, the reaction mixture was diluted with ethyl acetate. The separated organic layer was washed with brine, and dried over MgSO$_4$. After filtration, the filtrate was concentrated in vacuo, and the residue was purified with silica gel column chromatography (hexane/ethyl acetate=90/10 to 80/20) to obtain the title compound (108 mg, 56%).

(4) Synthesis of 1-benzyl-3,3-dimethylindolin-5-yl 4-isopropylphenylcarbamate

The title compound was synthesized from 1-benzyl-3,3-dimethylindolin-5-ol (50.0 mg, 0.197 mmol) using the same procedure employed for Example 2 (2). The product was obtained as a slightly brown solid (18.8 mg, 23%) having the following characteristics.

$^1$H-NMR (CDCl$_3$) δ(ppm): 1.24 (d, J=7.2 Hz, 6H), 1.30 (s, 6H), 2.89 (sep, J=7.2 Hz, 1H), 3.10 (s, 2H), 4.24 (s, 2H), 6.42 (d, J=8.2 Hz, 1H), 6.8-6.87 (m, 3H), 7.19 (d, J=8.2 Hz, 2H), 7.26-7.4 (m, 7H). Melting Point 143-147° C., MS (ESI+) m/z 415.5 (M+1).

Example 146

Synthesis of 1-benzyl-3-methylindolin-5-yl-4-isopropylphenylcarbamate (1) Synthesis of 1-[N-benzyl-N-(4-methoxyphenyl)amino]propan-2-on To a solution of N-benzyl-p-anisidine (2.00 g, 9.38 mmol) in 19 mL of ethanol was added lithium bromide (1.22 g, 14.0 mmol), NaHCO$_3$ (1.58 g, 18.8 mmol), chloroacetone (0.87 mL, 10.8 mmol) at room temperature, successively. After the reaction mixture was stirred at 80° C. for 3 h, the reaction mixture was added water, and extracted with ethyl acetate. The organic layer was washed with brine, and dried over MgSO$_4$. After filtration, the filtrate was concentrated in vacuo, and the residue was purified by silica gel column chromatography (hexane/ethyl acetate=95/5 to 80/20) to obtain the title compound (2.09 g, 83%).

(2) Synthesis of 1-benzyl-5-methoxy-3-methylindole

A solution of 1-[N-benzyl-N-(4-methoxyphenyl)amino]propan-2-on (863 mg, 3.20 mmol) in 9.6 mL of ethanol was added zinc chloride (1.3 g, 9.6 mmol) at room temperature. After the reaction mixture was stirred over night, zinc chloride (1.3 g, 9.6 mmol) was added with additional stirring for 10 h. After the reaction mixture was concentrated in vacuo, the residue was diluted with ethyl acetate, and washed with water, 1 M HCl, saturated NaHCO$_3$ aqueous solution and brine, successively, and dried over MgSO$_4$. After filtration, the filtrate was concentrated in vacuo, and the residue was purified by silica gel column chromatography (hexane/ethyl acetate=95/5 to 80/20) to obtain the title compound (503 mg, 62%).

(3) Synthesis of 1-benzyl-5-methoxy-3-methylindoline

To a solution of 1-benzyl-5-methoxy-3-methylindole (200 mg, 0.796 mmol) in a 1:1 solution (2.4 mL) of acetic acid and tetrahydrofuran was added sodium cyanoborohydride (150 mg, 2.38 mmol) at room temperature. After being stirred overnight, sodium cyanoborohydride (50 mg, 0.80 mmol) was added with additional stirring for 6 h. After the reaction mixture was neutralized by saturated NaHCO$_3$ aqueous solution, the reaction mixture was diluted with ethyl acetate. The separated organic layer was washed with brine, and dried over MgSO$_4$. After filtration, the filtrate was concentrated in vacuo, and the residue was purified with silica gel column chromatography (hexane/ethyl acetate=100/0 to 90/10) to obtain the title compound (62.4 mg, 31%).

(4) Synthesis of 1-benzyl-3-methylindolin-5-ol

To 1-benzyl-5-methoxy-3-methylindoline (78.5 mg, 0.310 mmol) was added a solution of 50% hydrogen bromide-acetic acid solution (0.80 mL) at room temperature. After the reaction mixture was stirred at 105° C. overnight, the reaction mixture was neutralized by saturated NaHCO$_3$ aqueous solution, and the solution was extracted with ethyl acetate. The extract was washed with brine, and dried over MgSO$_4$. After filtration, the filtrate was concentrated in vacuo, and the residue was purified by silica gel column chromatography (hexane/ethyl acetate=90/10 to 80/20) to obtain the title compound (59.5 mg, 80%).

(5) Synthesis of 1-benzyl-3-methylindolin-5-yl-4-isopropylphenylcarbamate

The title compound was synthesized from 1-benzyl-3-methylindolin-5-ol (30.0 mg, 0.125 mmol) using the same procedure employed for Example 2 (2). The product was obtained as a solid (17.8 mg, 36%) having the following characteristics.
$^1$H-NMR (CDCl$_3$) δ(ppm): 1.24 (d, J=6.8 Hz, 6H), 1.30 (d, J=6.8 Hz, 3H), 2.8-2.92 (m, 2H), 3.31 (sep, J=6.8 Hz, 1H), 3.53 (t, J=8.7 Hz, 1H), 4.10 (d, J=15 Hz, 1H), 4.34 (d, J=15 Hz, 1H), 6.44 (d, J=8.7 Hz, 1H), 6.8-6.9 (brs, 1H), 6.83 (dd, J=2.4, 8.7 Hz, 1H), 6.89 (brs, 1H), 7.19 (d, J=8.7 Hz, 2H), 7.26-7.4 (m, 7H). Melting Point 150-154° C., MS (ESI+) m/z 401.5 (M+1).

Example 147

Synthesis of 1-(2-pyridylmethyl)indolin-5-yl n-hexylcarbamate (1) Synthesis of 1-(2-pyridylmethyl)indolin-5-ol To a solution of 5-methoxyindole (758 mg, 5.15 mmol) in a 1:1 solution (7.7 mL) of acetic acid and tetrahydrofuran was added sodium cyanoborohydride (1.13 g, 18.0 mmol) at room temperature. After being stirred for 1 h, 2-pyridinecarboxyaldehyde (0.98 mL, 10.3 mmol) was added with additional stirring for 1 h. After the reaction mixture was neutralized by saturated NaHCO$_3$ aqueous solution, the reaction mixture was diluted with ethyl acetate. The separated organic layer was washed with brine, and dried over MgSO$_4$. After filtration, the filtrate was concentrated in vacuo, and the residue was purified with silica gel column chromatography (hexane/ethyl acetate=80/20 to 40/60) to obtain 1-(2-pyridylmethyl)-5-methoxyindoline (543 mg, 44%). To the above product was added a solution of 50% hydrogen bromide-acetic acid solution (10 mL) at room temperature. After the reaction mixture was stirred at 105° C. for 30 min, the reaction mixture was neutralized by saturated NaHCO$_3$ aqueous solution, and the solution was extracted with ethyl acetate. The extract was washed with brine, and dried over MgSO$_4$. After filtration, the filtrate was concentrated in vacuo, and the residue was purified by silica gel column chromatography (hexane/ethyl acetate=80/20 to 70/30) to obtain the title compound (313 mg, 61%) as a sticky oil.

(2) Synthesis of 1-(2-pyridylmethyl)indolin-5-yl n-hexylcarbamate

To a solution of 1-(2-pyridylmethyl)indolin-5-ol (20 mg, 88 μmol) in 0.5 mL of diethyl ether was added a piece of sodium (1 mg to 10 mg) at room temperature. After the reaction mixture was stirred at the same temperature for 2 min, n-hexylisocyanate (15 μL, 0.11 mmol, 1.2 equivalent) was added with additional stirring for 5 min to 10 min. After removal of sodium, the filtrate was concentrated in vacuo, and the residue was purified by silica gel column chromatography (hexane/ethyl acetate=80/20 to 30/70) to obtain the title compound (21.2 mg, 68%) as a slightly brown solid.
MS (ESI+) m/z 354.5 (M+1).

Example 148

Synthesis of 1-(2-pyridylmethyl)indolin-5-yl cyclohexylmethylcarbamate

The title compound was synthesized using the same procedure employed for Example 147 (2), but with cyclohexylmethylisocyanate instead of n-hexylisocyanate. The product was obtained as a white solid (27.6 mg, 85%) having the following characteristics.
MS (ESI+) m/z 366.5 (M+1).

Example 149

Synthesis of 1-(2-pyridylmethyl)indolin-5-yl cyclohexylcarbamate

The title compound was synthesized using the same procedure employed for Example 147 (2), but with cyclohexylisocyanate instead of n-hexylisocyanate. The product was obtained as a white solid (25.7 mg, 83%) having the following characteristics.
MS (ESI+) m/z 352.4 (M+1).

Example 150

Synthesis of 1-(2-pyridylmethyl)indolin-5-yl benzylcarbamate

The title compound was synthesized using the same procedure employed for Example 147 (2), but with benzylisocyanate instead of n-hexylisocyanate. The product was obtained as a white solid (22.5 mg, 71%) having the following characteristics.
MS (ESI+) m/z 360.5 (M+1).

Example 151

Synthesis of 1-(2-pyridylmethyl)indolin-5-yl 4-methoxyphenylcarbamate

The title compound was synthesized using the same procedure employed for Example 147 (2), but with 4-methoxyphenylisocyanate instead of n-hexylisocyanate. The product

Example 152

Synthesis of 1-(2-pyridylmethyl)indolin-5-yl 4-dimethylaminophenylcarbamate

The title compound was synthesized using the same procedure employed for Example 147 (2), but with 4-dimethylaminophenylisocyanate instead of n-hexylisocyanate. The product was obtained as a white solid (16.7 mg, 49%) having the following characteristics.
MS (ESI+) m/z 389.5 (M+1).

Example 153

Synthesis of 1-benzylindolin-5-yl 2,2-dimethylpropylcarbamate

The title compound was synthesized from 1-benzylindolin-5-ol (26 mg, 0.10 mmol) using the same procedure employed for Example 31, but with 2,2-dimethylpropylamine instead of 4-methoxybenzylamine. The product was obtained as a white solid (12.0 mg, 35%) having the following characteristics.
MS (ESI+) m/z 339.4 (M+1).

Example 154

Synthesis of 1-benzylindolin-5-yl (1-ethylpyrrolidin-2-yl)methylcarbamate

The title compound was synthesized from 1-benzylindolin-5-ol (26 mg, 0.10 mmol) using the same procedure employed for Example 31, but with (1-ethylpyrrolidin-2-yl)methylamine instead of 4-methoxybenzylamine. The product was obtained as a white solid (4.5 mg, 12%) having the following characteristics.
MS (ESI+) m/z 380.4 (M+1).

Example 155

Synthesis of 1-benzylindolin-5-yl 3-tetrahydrofurylmethylcarbamate

The title compound was synthesized from 1-benzylindolin-5-ol (26 mg, 0.10 mmol) using the same procedure employed for Example 31, but with 3-tetrahydrofurylmethylamine instead of 4-methoxybenzylamine. The product was obtained as a white solid (4.5 mg, 13%) having the following characteristics.
MS (ESI+) m/z 353.4 (M+1).

Example 156

Synthesis of 1-benzylindolin-5-yl 3-dimethylamino-2,2-dimethylpropylcarbamate

The title compound was synthesized from 1-benzylindolin-5-ol (26 mg, 0.10 mmol) using the same procedure employed for Example 31, but with 3-dimethylamino-2,2-dimethylpropylamine instead of 4-methoxybenzylamine. The product was obtained as a sticky oil (10.4 mg, 27%) having the following characteristics.
MS (ESI+) m/z 382.5 (M+1).

Example 157

Synthesis of 1-phenylindolin-5-yl 4-isopropylphenylcarbamate

To a solution of indolin-5-yl 4-isopropylphenylcarbamate (50 mg, 0.17 mmol) in 3.4 mL of acetonitrile was added 2-(trimethylsilyl)phenyl trifluoromethanesulfonate (41 μL, 0.17 mmol) and caesium fluoride (51 mg, 0.34 mmol) at room temperature, successively. After the reaction mixture was stirred at the same temperature overnight, the reaction mixture was diluted with ethyl acetate. The organic layer was washed with water and brine, and dried over MgSO$_4$. After filtration, the filtrate was concentrated in vacuo, and the residue was purified by silica gel column chromatography (hexane/ethyl acetate=95/5 to 80/20) to obtain the title compound as a white solid (5.2 mg, 8%).
MS (ESI+) m/z 373.4 (M+1).

Example 158

Synthesis of 3-(di-n-propylaminocarbonylmethyl)-1-methylindolin-5-yl 4-isopropylphenylcarbamate (1) Synthesis of 3-(di-n-propylaminocarbonylmethyl)-5-methoxyindole A solution of 5-methoxyindole-3-acetic acid (500 mg, 2.44 mmol) in 4.8 mL of N,N-dimethylformamide was added di-n-propylamine (0.60 mL, 7.2 mmol) and EDCI (1.90 g, 9.6 mmol) at room temperature. After the reaction mixture was stirred at the same temperature for 12 h, the reaction mixture was diluted with diethyl ether, and washed with water and brine, and dried over MgSO$_4$. After filtration, the filtrate was concentrated in vacuo, and the residue was purified by silica gel column chromatography to obtain the title compound (360 mg, 51%).

(2) Synthesis of 3-(di-n-propylaminocarbonylmethyl)-5-methoxy-1-methylindole

To a solution of 3-(di-n-propylaminocarbonylmethyl)-5-methoxyindole (180 mg, 0.62 mmol) in 1.8 mL of N,N-dimethylformamide was added sodium hydride (55%, 40 mg, 0.93 mmol) at 0° C. After the reaction mixture was stirred at the same temperature for 30 min, methyl iodide (0.10 mL, 1.2 mmol) was added with additional stirring at room temperature for 12 h. After the reaction mixture was diluted with diethyl ether, and washed with water and brine, and dried over MgSO$_4$. After filtration, the filtrate was concentrated in vacuo, and the residue was purified by silica gel column chromatography (hexane/ethyl acetate=95/5 to 80/20) to obtain the title compound (126 mg, 67%).

(3) Synthesis of 3-(di-n-propylaminocarbonylmethyl)-5-methoxy-1-methylindoline

To a solution of 3-(di-n-propylaminocarbonylmethyl)-5-methoxy-1-methylindole (78.5 mg, 0.310 mmol) in 0.75 mL of trifluoroacetic acid was added sodium cyanoborohydride (79 mg, 1.3 mmol) at room temperature. After the reaction mixture was stirred at the same temperature for 12 h, the reaction mixture was diluted with diethyl ether, and neutralized by 40% sodium hydroxide aqueous solution. The separated organic layer was washed with saturated NaHCO$_3$ aqueous solution and brine, and dried over MgSO$_4$. After filtration, the filtrate was concentrated in vacuo, and the residue was purified by silica gel column chromatography to obtain the title compound (63 mg, 83%).

(4) Synthesis of 3-(di-n-propylaminocarbonylmethyl)-1-methylindolin-5-yl 4-isopropylphenylcarbamate To a solution of 3-(di-n-propylaminocarbonylmethyl)-5-methoxy-1-methylindoline (62 mg, 0.20 mmol) in 1.0 mL of dry dichloromethane was added boron tribromide (0.116 mL, 1.20 mmol) at 0° C. After the reaction mixture was stirred at room temperature for 30 min, methanol (0.2 mL) was added. After the reaction mixture was diluted with diethyl ether, the solution was washed with saturated NaHCO$_3$ aqueous solution and brine, and dried over MgSO$_4$. After filtration, the filtrate was concentrated in vacuo to obtain crude 3-(di-n-propylaminocarbonylmethyl)-1-methylindolin-5-ol. The title compound was synthesized using the same procedure employed for Example 2 (2), but with the above product instead of 1-benzylindolin-5-ol. The product was obtained as a white solid (28.6 mg, 2 steps 32%) having the following characteristics.
MS (ESI+) m/z 452.4 (M+1).

Example 159

Synthesis of 3-(di-n-propylaminocarbonylmethyl)-1,2-dimethylindolin-5-yl 4-isopropylphenylcarbamate (1) Synthesis of 3-(di-n-propylaminocarbonylmethyl)-5-methoxy-2-methylindole The title compound was synthesized using the same procedure employed for Example 158 (1), but with 5-methoxy-2-methylindole-3-acetic acid (534 mg, 2.44 mmol) instead of 5-methoxyindole-3-acetic acid (500 mg, 2.44 mmol). The product was obtained (0.65 g, 88%).

(2) Synthesis of 3-(di-n-propylaminocarbonylmethyl)-1,2-dimethylindolin-5-yl-4-isopropylphenylcarbamate The title compound was synthesized using the same procedure employed for Example 158 (2) to (4), but with 3-(di-n-propylaminocarbonylmethyl)-5-methoxy-2-methylindole (0.65 g, 2.2 mmol) instead of 3-(di-n-propylaminocarbonyl-methyl)-5-methylindole. The product was obtained as a white solid (41.0 mg, 3 steps 4%).
MS (ESI+) m/z 466.5 (M+1).

Example 160

Synthesis of 3-(2-acetamidethyl)-1-benzylindolin-5-yl-4-isopropylphenylcarbamate (1) Synthesis of 3-(2-acetamidethyl)-1-benzyl-5-methoxyindole To a solution of 3-(2-acetamidethyl)-5-methoxyindole (100 mg, 0.431 mmol) in 0.86 mL of N,N-dimethylformamide was added sodium hydride (55%, 28 mg, 0.65 mmol) at 0° C. After the reaction mixture was stirred at room temperature for 30 min, benzyl bromide (77 μL, 0.65 mmol) was added with additional stirring for 12 h. After the reaction mixture was diluted with diethyl ether, and washed with water and brine, and dried over MgSO$_4$. After filtration, the filtrate was concentrated in vacuo, and the residue was purified by silica gel column chromatography to obtain the title compound (88 mg, 63%).

(2) Synthesis of 3-(2-acetamidethyl)-1-benzylindolin-5-yl-4-isopropylphenylcarbamate The title compound was synthesized using the same procedure employed for Example 158 (3) and (4), but with 3-(2-acetamidethyl)-1-benzyl-5-methoxyindole (44.0 mg, 0.137 mmol) instead of 3-(di-n-propylaminocarbonylmethyl)-5-methoxyindole. The product was obtained as a white solid (7.0 mg, 3 steps 11%).
$^1$H-NMR (CDCl$_3$) δ(ppm): 1.23 (d, J=6.8 Hz, 6H), 1.7-1.8 (m, 1H), 1.85-2.05 (m, 6H), 2.88 (sep, J=6.8 Hz, 1H), 3.05 (dd, J=7.2, 9.2 Hz, 1H), 3.2-3.4 (m, 3H), 3.48 (t, J=9.2 Hz, 1H), 4.21 (s, 2H), 5.57 (brs, 1H), 6.45 (d, J=8.2 Hz, 1H), 6.84 (dd, J=2.4, 8.7 Hz, 1H), 6.90 (brs, 1H), 7.18 (d, J=8.7 Hz, 2H), 7.25-7.4 (m, 8H). Melting Point 74-78° C., MS (ESI+) m/z 472.6 (M+1).

Example 161

Synthesis of 1-benzyl-3-(di-n-propylaminocarbonyl-methyl)indolin-5-yl 4-isopropylphenylcarbamate The title compound was synthesized using the same procedure employed for Example 160 (1) and (2), but with 3-(di-n-propylaminocarbonylmethyl)-5-methoxyindole (180 mg, 0.62 mmol) instead of 3-(2-acetamidethyl)-5-methoxyindole. The product was obtained as a white solid (36.0 mg, 4 steps 11%). $^1$H-NMR (CDCl$_3$) δ(ppm): 0.86 (t, J=6.8 Hz, 3H), 0.88 (t, J=6.8 Hz, 3H), 1.23 (d, J=6.8 Hz, 6H), 1.5-1.6 (m, 4H), 2.58 (dd, J=9.7, 16 Hz, 1H), 2.70 (dd, J=4.8, 16 Hz, 1H), 2.88 (sep, J=6.8 Hz, 1H), 3.03 (dd, J=6.3, 9.2 Hz, 1H), 3.12 (dt, J=3.9, 8.2 Hz, 2H), 3.15-3.25 (m, 1H), 3.28-3.38 (m, 1H), 3.64 (t, J=9.2 Hz, 1H), 3.75-3.85 (m, 1H), 4.22 (s, 2H), 6.43 (d, J=8.2 Hz, 1H), 6.85 (dd, J=2.4, 8.2 Hz, 1H), 6.89 (brs, 1H), 6.91 (brs, 1H), 7.18 (d, J=8.7 Hz, 2H), 7.25-7.4 (m, 7H). Melting Point 157-161° C., MS (ESI+) m/z 528.6 (M+1).

Example 162

Synthesis of 1-benzyl-3-(di-n-propylaminocarbonyl-methyl)-2-methylindolin-5-yl 4-isopropyl phenylcarbamate The title compound was synthesized using the same procedure employed for Example 160 (1) and (2), but with 3-(di-n-propylaminocarbonylmethyl)-5-methoxy-2-methylindole (180 mg, 0.596 mmol) instead of 3-(2-acetamidethyl)-5-methoxyindole. The product was obtained as a white solid (6.1 mg, 4 steps 1.9%).
$^1$H-NMR (CDCl$_3$) δ(ppm): 0.86 (t, J=6.8 Hz, 3H), 0.88 (t, J=6.8 Hz, 3H) 1.23 (d, J=6.8 Hz, 6H), 1.25 (d, J=5.8 Hz, 2H), 1.5-1.6 (m, 4H), 2.55 (dd, J=9.7, 16 Hz, 1H), 2.63 (dd, J=4.8, 16 Hz, 1H), 2.88 (sep, J=6.8 Hz, 1H), 3.1-3.25 (m, 3H), 3.3-3.5 (m, 3H), 4.18 (d, J=16 Hz, 1H), 4.36 (d, J=16 Hz, 1H), 6.25 (d, J=8.7 Hz, 1H), 6.79 (dd, J=2.4, 8.7 Hz, 1H), 6.87 (d, J=2.4 Hz, 1H), 7.18 (d, J=8.7 Hz, 2H), 7.2-7.4 (m, 7H). MS (ESI+) m/z 542.8 (M+1).

Example 163

Synthesis of 2-(di-n-propylaminocarbonyl)-1-benzylindolin-5-yl 4-isopropylphenylcarbamate (1) Synthesis of 2-(di-n-propylaminocarbonyl)-5-methoxyindole To a solution of 5-methoxyindole-2-carboxylic acid (500 mg, 2.62 mmol) in 13 mL of N,N-dimethylformamide was added di-n-propylamine (1.07 mL, 7.8 mmol) and HATU (1.09 g, 2.88 mmol) at 0° C. After the reaction mixture was stirred at room temperature for 12 h, the reaction mixture was diluted with diethyl ether, and washed with water and brine, and dried over $MgSO_4$. After filtration, the filtrate was concentrated in vacuo, and the residue was purified by silica gel column chromatography to obtain the title compound (0.53 g, 74%).

(2) Synthesis of 2-(di-n-propylaminocarbonyl)-5-methoxy-1-benzylindole

The title compound was synthesized using the same procedure employed for Example 160 (1), but with 2-(di-n-propylaminocarbonyl)-5-methoxyindole (0.45 g, 1.64 mmol) instead of 3-(2-acetamidethyl)-5-methoxyindole. The product was obtained (0.64 g, quant.).

(3) Synthesis of 2-(di-n-propylaminocarbonyl)-5-methoxy-1-benzylindoline

To a solution of 2-(di-n-propylaminocarbonyl)-5-methoxy-1-benzylindole (654 mg, 1.79 mmol) in 18 mL of methanol was added magnesium turnings (0.87 g, 36 mmol) at 0° C. After the reaction mixture was stirred for 12 h with slowly warming up to room temperature, the reaction mixture was diluted with ethyl acetate, and washed with 1 M HCl, saturated $NaHCO_3$ aqueous solution and brine, and dried over $MgSO_4$. After filtration, the filtrate was concentrated in vacuo, and the residue was purified by silica gel column chromatography to obtain the title compound (405 mg, 62%).

(4) Synthesis of 3-(2-acetamidethyl)-1-benzylindolin-5-yl-4-isopropylphenylcarbamate The title compound was synthesized using the same procedure employed for Example 158 (4), but with 2-(di-n-propylaminocarbonyl)-5-methoxy-1-benzylindoline (94.0 mg, 0.256 mmol) instead of 3-(di-n-propylaminocarbonylmethyl)-5-methoxy-1-methylindoline. The product was obtained as a white solid (28.5 mg, 2 steps 22%) having the following characteristics.

$^1$H-NMR (CDCl$_3$) δ(ppm): 0.76 (t, J=7.2 Hz, 3H), 0.88 (t, J=7.2 Hz, 3H), 1.23 (d, J=6.8 Hz, 6H), 1.2-1.7 (m, 4H), 2.85-3.1 (m, 4H), 3.15-3.25 (m, 1H), 3.28-3.4 (m, 2H), 4.14 (d, J=15 Hz, 1H), 4.47 (dd, J=7.7, 9.7 Hz, 1H), 4.56 (d, J=15 Hz, 1H), 6.37 (d, J=8.2 Hz, 1H), 6.76-6.83 (m, 2H), 7.03 (brs, 1H), 7.17 (d, J=8.7 Hz, 2H), 7.2-7.4 (m, 7H). Melting Point 62-66° C., MS (ESI+) m/z 514 (M+1).

Example 164

Synthesis of 1-(2-pyridylmethyl)-3,3-dimethylindolin-5-yl n-hexylcarbamate (1) Synthesis of 1-(2-pyridylmethyl)-3,3-dimethylindolin-5-ol To a solution of 3,3-dimethylindolin-5-ol monohydrochloride (200 mg, 1 mmol) in a 1:1 solution (2.0 mL) of acetic acid and tetrahydrofuran was added pyridine-2-carboxyaldehyde (214 mg, 2 mmol) and sodium acetate (123 mg, 1.5 mmol) at room temperature. After being stirred at the same temperature for 1 h, the reaction mixture was neutralized by saturated $NaHCO_3$ aqueous solution, and diluted with ethyl acetate. The separated organic layer was washed with brine, and dried over $MgSO_4$. After filtration, the filtrate was concentrated in vacuo, and the residue was purified with silica gel column chromatography (hexane/ethyl acetate=50/50 to 20/80) to obtain the title compound (172 mg, 68%).

$^1$H-NMR (CDCl$_3$) δ(ppm): 1.31 (s, 6H), 3.14 (s, 2H), 4.32 (s, 2H), 6.28 (d, J=8.2 Hz, 1H), 6.52 (dd, J=2.4, 8.2 Hz, 1H), 6.61 (d, J=2.4 Hz, 1H), 7.18 (dd, J=4.8, 7.7 Hz, 1H), 7.44 (d, J=7.7 Hz, 1H), 7.66 (dd, J=7.2, 7.7 Hz, 1H), 8.57 (dd, J=4.8 Hz, 1H). MS (ESI+) m/z 255.4 (M+1).

(2) Synthesis of 1-(2-pyridylmethyl)-3,3-dimethylindolin-5-yl n-hexyl carbamate

The title compound was synthesized from 1-(2-pyridylmethyl)-3,3-dimethylindolin-5-ol (20.0 mg, 0.09 mmol) using the same procedure employed for Example 2 (2), but with n-hexylisocyanate instead of 4-isopropylphenylisocyanate. The product was obtained as a white solid (14.3 mg, 48%) having the following characteristics.

MS (ESI+) m/z 382.4 (M+1).

Example 165

Synthesis of 1-(2-pyridylmethyl)-3,3-dimethylindolin-5-yl cyclohexylmethylcarbamate The title compound was synthesized from 1-(2-pyridylmethyl)-3,3-dimethylindolin-5-ol (20.0 mg, 0.09 mmol) using the same procedure employed for Example 2 (2), but with cyclohexylmethylisocyanate instead of 4-isopropylphenylisocyanate. The product was obtained as a white solid (16.5 mg, 53%) having the following characteristics.

MS (ESI+) m/z 394.4 (M+1).

Example 166

Synthesis of 1-(2-pyridylmethyl)-3,3-dimethylindolin-5-yl cyclohexylcarbamate

The title compound was synthesized from 1-(2-pyridylmethyl)-3,3-dimethylindolin-5-ol (20.0 mg, 0.09 mmol) using the same procedure employed for Example 2 (2), but with cyclohexylisocyanate instead of 4-isopropylphenylisocyanate. The product was obtained as a white solid (15.4 mg, 52%) having the following characteristics.

MS (ESI+) m/z 380.4 (M+1).

Example 167

Synthesis of 1-(2-pyridylmethyl)-3,3-dimethylindolin-5-yl benzylcarbamate

The title compound was synthesized from 1-(2-pyridylmethyl)-3,3-dimethylindolin-5-ol (20.0 mg, 0.09 mmol) using the same procedure employed for Example 2 (2), but with benzylisocyanate instead of 4-isopropylphenylisocyanate.

The product was obtained as a white solid (15.5 mg, 51%) having the following characteristics.
MS (ESI+) m/z 388.3 (M+1).

Example 168

Synthesis of 1-(2-pyridylmethyl)-3,3-dimethylindolin-5-yl 4-methoxyphenylcarbamate The title compound was synthesized from 1-(2-pyridylmethyl)-3,3-dimethylindolin-5-ol (20.0 mg, 0.09 mmol) using the same procedure employed for Example 2 (2), but with 4-methoxyphenylisocyanate instead of 4-isopropylphenylisocyanate. The product was obtained as a white solid (14.6 mg, 46%) having the following characteristics.
MS (ESI+) m/z 404.4 (M+1).

Example 169

Synthesis of 1-(2-pyridylmethyl)-3,3-dimethylindolin-5-yl 4-dimethylaminophenylcarbamate The title compound was synthesized from 1-(2-pyridylmethyl)-3,3-dimethylindolin-5-ol (20.0 mg, 0.09 mmol) using the same procedure employed for Example 2 (2), but with 4-dimethylaminophenylisocyanate instead of 4-isopropylphenylisocyanate. The product was obtained as a white solid (5.2 mg, 16%) having the following characteristics.
MS (ESI+) m/z 417.4 (M+1).

Example 170

Synthesis of 1-(3-pyridylmethyl)-3,3-dimethylindolin-5-yl n-hexylcarbamate (1) Synthesis of 1-(3-pyridylmethyl)-3,3-dimethylindolin-5-ol The title compound was synthesized using the same procedure employed for Example 164 (1), but with pyridine-3-carboxyaldehyde (200 mg, 1 mmol) instead of pyridine-2-carboxyaldehyde. The product was obtained (149 mg, 59%).
MS (ESI+) m/z 255.4 (M+1).

(2) Synthesis of 1-(3-pyridylmethyl)-3,3-dimethylindolin-5-yl n-hexylcarbamate

The title compound was synthesized from 1-(3-pyridylmethyl)-3,3-dimethylindolin-5-ol (20.0 mg, 0.09 mmol) using the same procedure employed for Example 2 (2), but with n-hexylisocyanate instead of 4-isopropylphenylisocyanate. The product was obtained as a white solid (10.7 mg, 36%) having the following characteristics.
MS (ESI+) m/z 382.4 (M+1).

Example 171

Synthesis of 1-(3-pyridylmethyl)-3,3-dimethylindolin-5-yl cyclohexylmethylcarbamate The title compound was synthesized from 1-(3-pyridylmethyl)-3,3-dimethylindolin-5-ol (20.0 mg, 0.09 mmol) using the same procedure employed for Example 2 (2), but with cyclohexylmethylisocyanate instead of 4-isopropylphenylisocyanate. The product was obtained as a white solid (11.6 mg, 38%) having the following characteristics.
MS (ESI+) m/z 394.4 (M+1).

Example 172

Synthesis of 1-(3-pyridylmethyl)-3,3-dimethylindolin-5-yl cyclohexylcarbamate

The title compound was synthesized from 1-(3-pyridylmethyl)-3,3-dimethylindolin-5-ol (20.0 mg, 0.09 mmol) using the same procedure employed for Example 2 (2), but with cyclohexylisocyanate instead of 4-isopropylphenylisocyanate. The product was obtained as a white solid (12.5 mg, 42%) having the following characteristics.
MS (ESI+) m/z 380.4 (M+1).

Example 173

Synthesis of 1-(3-pyridylmethyl)-3,3-dimethylindolin-5-yl benzylcarbamate

The title compound was synthesized from 1-(3-pyridylmethyl)-3,3-dimethylindolin-5-ol (20.0 mg, 0.09 mmol) using the same procedure employed for Example 2 (2), but with benzylisocyanate instead of 4-isopropylphenylisocyanate. The product was obtained as a white solid (12.8 mg, 40%) having the following characteristics.
MS (ESI+) m/z 388.4 (M+1).

Example 174

Synthesis of 1-(3-pyridylmethyl)-3,3-dimethylindolin-5-yl 4-methoxyphenylcarbamate The title compound was synthesized from 1-(3-pyridylmethyl)-3,3-dimethylindolin-5-ol (20.0 mg, 0.09 mmol) using the same procedure employed for Example 2 (2), but with 4-methoxyphenylisocyanate instead of 4-isopropylphenylisocyanate. The product was obtained as a white solid (4.2 mg, 14%) having the following characteristics.
MS (ESI+) m/z 404.4 (M+1).

Example 175

Synthesis of 1-(3-pyridylmethyl)-3,3-dimethylindolin-5-yl 4-dimethylaminophenylcarbamate The title compound was synthesized from 1-(3-pyridylmethyl)-3,3-dimethylindolin-5-ol (20.0 mg, 0.09 mmol) using the same procedure employed for Example 2 (2), but with 4-dimethylaminophenylisocyanate instead of 4-isopropylphenylisocyanate. The product was obtained as a white solid (4.7 mg, 14%) having the following characteristics.
MS (ESI+) m/z 417.4 (M+1).

Example 176

Synthesis of 1-(3-pyridylmethyl)-3,3-dimethylindolin-5-yl 4-isopropylphenylcarbamate The title compound was synthesized from 1-(3-pyridylmethyl)-3,3-dimethylindolin-5-ol (20.0 mg, 0.09 mmol) using the same procedure employed for Example 2 (2). The product was obtained as a white solid (8.7 mg, 27%) having the following characteristics.
MS (ESI+) m/z 416.4 (M+1).

Example 177

Synthesis of 1-(4-pyridylmethyl)-3,3-dimethylindolin-5-yl n-hexylcarbamate (1) Synthesis of 1-(4-pyridylmethyl)-3,3-dimethylindolin-5-ol The title compound was synthesized using the same procedure employed for Example 164 (1), but with pyridine-4-carboxyaldehyde (200 mg, 1 mmol) instead of pyridine-2-carboxyaldehyde. The product was obtained (144 mg, 57%).
$^1$H-NMR (CDCl$_3$) δ(ppm): 1.30 (s, 6H), 3.05 (s, 2H), 4.16 (s, 2H), 6.25 (d, J=8.2 Hz, 1H), 6.52 (dd, J=2.4, 8.2 Hz, 1H), 6.62 (d, J=2.4 Hz, 1H), 7.31 (br d, J=6.3 Hz, 2H), 8.56 (br d, J=6.3 Hz, 2H). MS (ESI+) m/z 255.4 (M+1).

(2) Synthesis of 1-(4-pyridylmethyl)-3,3-dimethylindolin-5-yl n-hexylcarbamate

The title compound was synthesized from 1-(4-pyridylmethyl)-3,3-dimethylindolin-5-ol (20.0 mg, 0.09 mmol) using the same procedure employed for Example 2 (2), but with n-hexylisocyanate instead of 4-isopropylphenylisocyanate. The product was obtained as a white solid (10.4 mg, 35%) having the following characteristics.
MS (ESI+) m/z 382.3 (M+1).

Example 178

Synthesis of 1-(4-pyridylmethyl)-3,3-dimethylindolin-5-yl cyclohexylmethylcarbamate The title compound was synthesized from 1-(4-pyridylmethyl)-3,3-dimethylindolin-5-ol (20.0 mg, 0.09 mmol) using the same procedure employed for Example 2 (2), but with cyclohexylmethylisocyanate instead of 4-isopropylphenylisocyanate. The product was obtained as a white solid (5.8 mg, 19%) having the following characteristics.
MS (ESI+) m/z 394.3 (M+1).

Example 179

Synthesis of 1-(4-pyridylmethyl)-3,3-dimethylindolin-5-yl cyclohexylcarbamate

The title compound was synthesized from 1-(4-pyridylmethyl)-3,3-dimethylindolin-5-ol (20.0 mg, 0.09 mmol) using the same procedure employed for Example 2 (2), but with cyclohexylisocyanate instead of 4-isopropylphenylisocyanate. The product was obtained as a white solid (10.1 mg, 34%) having the following characteristics.
MS (ESI+) m/z 380.4 (M+1).

Example 180

Synthesis of 1-(4-pyridylmethyl)-3,3-dimethylindolin-5-yl benzylcarbamate

The title compound was synthesized from 1-(4-pyridylmethyl)-3,3-dimethylindolin-5-ol (20.0 mg, 0.09 mmol) using the same procedure employed for Example 2 (2), but with benzylisocyanate instead of 4-isopropylphenylisocyanate. The product was obtained as a white solid (11.7 mg, 38%) having the following characteristics.
MS (ESI+) m/z 388.3 (M+1).

Example 181

Synthesis of 1-(4-pyridylmethyl)-3,3-dimethylindolin-5-yl-4-methoxyphenylcarbamate The title compound was synthesized from 1-(4-pyridylmethyl)-3,3-dimethylindolin-5-ol (20.0 mg, 0.09 mmol) using the same procedure employed for Example 2 (2), but with 4-methoxyphenylisocyanate instead of 4-isopropylphenylisocyanate. The product was obtained as a white solid (4.2 mg, 13%) having the following characteristics.
MS (ESI+) m/z 404.4 (M+1).

Example 182

Synthesis of 1-(4-pyridylmethyl)-3,3-dimethylindolin-5-yl 4-dimethylaminophenylcarbamate The title compound was synthesized from 1-(4-pyridylmethyl)-3,3-dimethylindolin-5-ol (20.0 mg, 0.09 mmol) using the same procedure employed for Example 2 (2), but with 4-dimethylaminophenylisocyanate instead of 4-isopropylphenylisocyanate. The product was obtained as a white solid (2.1 mg, 6%) having the following characteristics.
$^1$H-NMR (CDCl$_3$) δ(ppm): 1.32 (s, 6H), 2.92 (s, 6H), 3.14 (s, 2H), 4.23 (s, 2H), 6.34 (d, J=8.2 Hz, 1H), 6.7 (m, 1H), 6.72 (d, J=8.9 Hz, 2H), 6.87 (brs, 1H), 7.25 (m, 2H), 7.29 (br d, J=5.3 Hz, 2H), 8.57 (brd, J=5.3 Hz, 2H).
MS (ESI+) m/z 417.2 (M+1).

Example 183

Synthesis of 1-(4-pyridylmethyl)-3,3-dimethylindolin-5-yl-4-isopropylphenylcarbamate The title compound was synthesized from 1-(4-pyridylmethyl)-3,3-dimethylindolin-5-ol (20.0 mg, 0.09 mmol) using the same procedure employed for Example 2 (2). The product was obtained as a white solid (7.4 mg, 23%) having the following characteristics.
MS (ESI+) m/z 416.4 (M+1).

Example 184

Synthesis of 1-benzyl-3,3-dimethylindolin-5-yl n-hexylcarbamate

The title compound was synthesized from 1-benzyl-3,3-dimethylindolin-5-ol (20.0 mg, 0.09 mmol) using the same procedure employed for Example 2 (2), but with n-hexylisocyanate instead of 4-isopropylphenylisocyanate. The product was obtained as a white solid (3.4 mg, 11%) having the following characteristics.
MS (ESI+) m/z 381.4 (M+1).

Example 185

Synthesis of 1-benzyl-3,3-dimethylindolin-5-yl cyclohexylmethylcarbamate

The title compound was synthesized from 1-benzyl-3,3-dimethylindolin-5-ol (20.0 mg, 0.09 mmol) using the same procedure employed for Example 2 (2), but with cyclohexylmethylisocyanate instead of 4-isopropylphenylisocyanate. The product was obtained as a white solid (10.5 mg, 34%) having the following characteristics.
MS (ESI+) m/z 393.4 (M+1).

Example 186

Synthesis of 1-benzyl-3,3-dimethylindolin-5-yl cyclohexylcarbamate

The title compound was synthesized from 1-benzyl-3,3-dimethylindolin-5-ol (20.0 mg, 0.09 mmol) using the same procedure employed for Example 2 (2), but with cyclohexylisocyanate instead of 4-isopropylphenylisocyanate. The product was obtained as a white solid (12.2 mg, 41%) having the following characteristics.
MS (ESI+) m/z 379.4 (M+1).

Example 187

Synthesis of 1-benzyl-3,3-dimethylindolin-5-yl benzylcarbamate

The title compound was synthesized from 1-benzyl-3,3-dimethylindolin-5-ol (20.0 mg, 0.09 mmol) using the same procedure employed for Example 2 (2), but with benzylisocyanate instead of 4-isopropylphenylisocyanate. The product was obtained as a white solid (10.3 mg, 36%) having the following characteristics.
MS (ESI+) m/z 387.4 (M+1).

Example 188

Synthesis of 1-benzylindolin-5-yl-4-tetrahydropyranylmethylcarbamate

The title compound was synthesized from 1-benzylindolin-5-ol (46.5 mg, 0.18 mmol) using the same procedure employed for Example 31, but with 4-aminomethyltetrahydropyran instead of 4-methoxybenzylamine. The product was obtained as a white solid (25.8 mg, 40%) having the following characteristics.
MS (ESI+) m/z 367.4 (M+1).

Example 189

Synthesis of 1-(2-pyridylmethyl)-3,3-dimethylindolin-5-yl-4-isopropylphenylcarbamate The title compound was synthesized from 1-(2-pyridylmethyl)-3,3-dimethylindolin-5-ol (20.0 mg, 0.09 mmol) using the same procedure employed for Example 2 (2). The product was obtained as a white solid (25.6 mg, 78%) having the following characteristics.
MS (ESI+) m/z 416.4 (M+1).

Example 190

Synthesis of 1-benzyl-3,3-dimethylindolin-5-yl-4-methoxyphenylcarbamate

The title compound was synthesized from 1-benzyl-3,3-dimethylindolin-5-ol (20.0 mg, 0.09 mmol) using the same procedure employed for Example 2 (2), but with 4-methoxyphenylisocyanate instead of 4-isopropylphenylisocyanate. The product was obtained as a white solid (25.4 mg, 80%) having the following characteristics.
MS (ESI+) m/z 403.4 (M+1).

Example 191

Synthesis of 1-benzyl-3,3-dimethylindolin-5-yl-4-dimethylaminophenylcarbamate

The title compound was synthesized from 1-benzyl-3,3-dimethylindolin-5-ol (20.0 mg, 0.09 mmol) using the same procedure employed for Example 2 (2), but with 4-dimethylaminophenylisocyanate instead of 4-isopropylphenylisocyanate. The product was obtained as a white solid (14.2 mg, 43%) having the following characteristics.
MS (ESI+) m/z 416.4 (M+1).

Example 192

Synthesis of 1-(2-pyridylmethyl)-3,3-dimethylindolin-5-yl 2-(furfurylthio)ethylcarbamate The title compound was synthesized from 1-(2-pyridylmethyl)-3,3-dimethylindolin-5-yl dihydrochloride (50.0 mg, 0.15 mmol) using the same procedure employed for Example 31, but with 2-(furfurylthio)ethylamine instead of 4-methoxybenzylamine. The product was obtained as a white solid (22.9 mg, 34%) having the following characteristics.
$^1$H-NMR (CDCl$_3$) δ(ppm): 1.32 (s, 6H), 2.71 (t, J=6.4 Hz, 2H), 3.23 (s, 2H), 3.41 (dt, J=6.2, 6.3 Hz, 2H), 3.76 (s, 2H), 4.38 (s, 2H), 5.32 (m, 1H), 6.22 (d, J=3.0 Hz, 1H), 6.31 (m, 1H), 6.33 (d, J=8.3 Hz, 1H), 6.76 (dd, J=2.3, 8.3 Hz, 1H), 6.80 (d, J=2.3 Hz, 1H), 7.19 (dd, J=5, 7 Hz, 1H), 7.37 (br s, 1H), 7.40 (d, J=7.7 Hz, 1H), 7.66 (ddd, J=1.7, 7.7, 7.7 Hz, 1H), 8.57 (br d, J=5 Hz, 1H). MS (ESI+) m/z 438 (M+1).

Example 193

Synthesis of 1-(2-pyridylmethyl)-3,3-dimethylindolin-5-yl 3-tetrahydrofurylmethylcarbamate To a suspension of 1-(2-pyridylmethyl)-3,3-dimethylindolin-5-ol dihydrochloride (50.0 mg, 0.15 mmol) in 1 mL of dry tetrahydrofuran was added 4-nitrophenyl chloroformate (34 mg, 0.165 mmol) and diisopropylethylamine (91 µL, 0.52 mmol) under ice-cooled conditions. After the reaction mixture was stirred at room temperature for 1 h, 3-tetrahydrofurylmethylamine (17 µL, 0.165 mmol) and diisopropylethylamine (39 µL, 0.225 mmol) was added with additional stirring overnight. After the reaction mixture was added with water (10 mL), the solution was extracted with ethyl acetate (10 mL). The extract was washed with brine, and dried over MgSO$_4$. After filtration, the filtrate was concentrated in vacuo, and the residue was purified by silica gel column chromatography (hexane/ethyl acetate=50/50 to 10/90) to obtain the title compound (10.7 mg, 18%) as a white solid having the following characteristics.
$^1$H-NMR (CDCl$_3$) δ(ppm): 1.32 (s, 6H), 1.67 (m, 1H), 2.07 (m, 1H), 2.53 (m, 1H), 3.23 (s, 2H), 3.28 (m, 2H), 3.57 (m, 1H), 3.76 (m, 1H), 3.83-3.93 (m, 2H), 4.37 (s, 2H), 5.13 (m, 1H), 6.33 (d, J=8.3 Hz, 1H), 6.76 (dd, J=2.3, 8.3 Hz, 1H), 6.80 (d, J=2.3 Hz, 1H), 7.19 (dd, J=5, 7 Hz, 1H), 7.40 (d, J=7.7 Hz, 1H), 7.66 (ddd, J=1.7, 7.7, 7.7 Hz, 1H), 8.57 (br d, J=5 Hz, 1H). MS (ESI+) m/z 382 (M+1).

Example 194

Synthesis of 1-benzyl-3,3-dimethylindolin-5-yl 3-tetrahydrofurylmethylcarbamate

The title compound was synthesized from 1-benzyl-3,3-dimethylindolin-5-ol monohydrochloride (50.0 mg, 0.17 mmol) using the same procedure employed for Example 31, but with 3-tetrahydrofurylmethylamine instead of 4-methoxybenzylamine. The product was obtained as a white solid (7.0 mg, 11%) having the following characteristics.
$^1$H-NMR (CDCl$_3$) δ(ppm): 1.28 (s, 6H), 1.67 (m, 1H), 2.07 (m, 1H), 2.53 (m, 1H), 3.08 (s, 2H), 3.28 (m, 2H), 3.57 (m, 1H), 3.76 (m, 1H), 3.83-3.93 (m, 2H), 4.22 (s, 2H), 5.10 (m, 1H), 6.39 (d, J=8.0 Hz, 1H), 6.77 (dd, J=2.4, 8 Hz, 1H), 6.78 (d, J=2 Hz, 1H), 7.24-7.36 (m, 5H). MS (ESI+) m/z 381 (M+1).

Example 195

Synthesis of 1-benzyl-3,3-dimethylindolin-5-yl 2-(2,4-dichlorophenyl)ethylcarbamate The title compound was synthesized from 1-benzyl-3,3-dimethylindolin-5-ol monohydrochloride (50.0 mg, 0.17 mmol) using the same procedure employed for Example 31, but with 2-(2,4-dichlorophenyl)ethylamine instead of 4-methoxybenzylamine. The product was obtained as a white solid (16.4 mg, 20%) having the following characteristics.
$^1$H-NMR (CDCl$_3$) δ(ppm): 1.28 (s, 6H), 3.00 (t, J=7.0 Hz, 2H), 3.08 (s, 2H), 3.50 (dt, J=7, 7 Hz, 2H), 4.22 (s, 2H), 4.99 (m, 1H), 6.39 (d, J=8.5 Hz, 1H), 6.74 (dd, J=2.2, 8 Hz, 1H), 6.75 (d, J=2 Hz, 1H), 7.2 (m, 2H), 7.24-7.36 (m, 5H), 7.40 (d, J=1.3 Hz, 1H). MS (ESI+) m/z 469 (M+1).

Example 196

Synthesis of 1-benzyl-3,3-dimethylindolin-5-yl 2-(furfurylthio)ethylcarbamate

The title compound was synthesized from 1-benzyl-3,3-dimethylindolin-5-ol monohydrochloride (50.0 mg, 0.17 mmol) using the same procedure employed for Example 31, but with 2-(furfurylthio)ethylamine instead of 4-methoxybenzylamine. The product was obtained as a white solid (30.9 mg, 41%) having the following characteristics.
$^1$H-NMR (CDCl$_3$) δ(ppm): 1.28 (s, 6H), 2.71 (t, J=6.4 Hz, 2H), 3.08 (s, 2H), 3.41 (dt, J=6, 6.2 Hz, 2H), 3.76 (s, 2H), 4.22 (s, 2H), 5.29 (m, 1H), 6.22 (d, J=2.7 Hz, 1H), 6.31 (m, 1H), 6.39 (d, J=8.3 Hz, 1H), 6.76 (dd, J=2.2, 8 Hz, 1H), 6.78 (d, J=2 Hz, 1H), 7.24-7.36 (m, 5H), 7.37 (br s, 1H). MS (ESI+) m/z 437 (M+1).

Example 197

Synthesis of 1-benzyl-3,3-dimethylindolin-5-yl-4-tetrahydropyranylmethylcarbamate The title compound was synthesized from 1-benzyl-3,3-dimethylindolin-5-ol monohydrochloride (50.0 mg, 0.17 mmol) using the same procedure employed for Example 31, but with 4-aminomethyltetrahydropyran instead of 4-methoxybenzylamine. The product was obtained as a white solid (39.2 mg, 57%) having the following characteristics.
$^1$H-NMR (CDCl$_3$) δ(ppm): 1.28 (s, 6H), 1.36 (m, 2H), 1.67 (d, J=13 Hz, 2H), 1.81 (m, 1H), 3.08 (s, 2H), 3.16 (t, J=6.5 Hz, 2H), 3.39 (dt, J=2, 11 Hz, 2H), 4.00 (dd, J=4.11 Hz, 2H), 4.22 (s, 2H), 5.03 (m, 1H), 6.39 (d, J=8.1 Hz, 1H), 6.76 (dd, J=2.3, 8 Hz, 1H), 6.78 (d, J=2 Hz, 1H), 7.24-7.36 (m, 5H). MS (ESI+) m/z 395 (M+1).

Example 198

Synthesis of 1-(2-pyridylmethyl)-3,3-dimethylindolin-5-yl 2-(2,4-dichlorophenyl)ethylcarbamate The title compound was synthesized from 1-(2-pyridylmethyl)-3,3-dimethylindolin-5-ol dihydrochloride (50.0 mg, 0.15 mmol) using the same procedure employed for Example 31, but with 2-(2,4-dichlorophenyl)ethylamine instead of 4-methoxybenzylamine. The product was obtained as a white solid (30.1 mg, 42%) having the following characteristics.
$^1$H-NMR (CDCl$_3$) δ(ppm): 1.32 (s, 6H), 3.00 (t, J=7 Hz, 2H), 3.23 (s, 2H), 3.50 (dt, J=7, 7 Hz, 2H), 4.37 (s, 2H), 5.02 (m, 1H), 6.33 (d, J=8.3 Hz, 1H), 6.73 (dd, J=2, 8.3 Hz, 1H), 6.77 (d, J=2 Hz, 1H), 7.14-7.22 (m, 3H), 7.39 (d, J=7 Hz, 1H), 7.40 (d, J=1 Hz, 1H), 7.66 (ddd, J=1.7, 7.6, 7.6 Hz, 1H), 8.57 (br d, J=5 Hz, 1H). MS (ESI+) m/z 470 (M+1).

Example 199

Synthesis of 1-(2-pyridylmethyl)-3,3-dimethylindolin-5-yl 4-tetrahydropyranylmethylcarbamate The title compound was synthesized from 1-(2-pyridylmethyl)-3,3-dimethylindolin-5-ol dihydrochloride (50.0 mg, 0.15 mmol) using the same procedure employed for Example 31, but with 4-aminomethyltetrahydropyran instead of 4-methoxybenzylamine. The product was obtained as a white solid (13.0 mg, 22%) having the following characteristics.
$^1$H-NMR (CDCl$_3$) δ(ppm): 1.32 (s, 6H), 1.36 (m, 2H), 1.66 (d, J=13 Hz, 2H), 1.81 (m, 1H), 3.16 (t, J=6.5 Hz, 2H), 3.23 (s, 2H), 3.39 (br t, J=11 Hz, 2H), 4.00 (dd, J=4.11 Hz, 2H), 4.38 (s, 2H), 5.07 (m, 1H), 6.33 (d, J=8.3 Hz, 1H), 6.76 (dd, J=2.2, 8.3 Hz, 1H), 6.80 (d, J=2 Hz, 1H), 7.19 (m, 1H), 7.40 (d, J=7.7 Hz, 1H), 7.66 (ddd, J=1, 7.7, 7.7 Hz, 1H), 8.57 (br d, J=5 Hz, 1H). MS (ESI+) m/z 396 (M+1).

Example 200

Synthesis of 1-(3-pyridylmethyl)-3,3-dimethylindolin-5-yl 2-(furfurylthio)ethylcarbamate (1) Synthesis of 1-(3-pyridylmethyl)-3,3-dimethylindolin-5-yl 4-nitrophenylcarbonate To a suspension of 1-(3-pyridylmethyl)-3,3-dimethylindolin-5-ol dihydrochloride (100.0 mg, 0.30 mmol) in 1 mL of dry tetrahydrofuran was added 4-nitrophenyl chloroformate (68 mg, 0.33 mmol) and diisopropylethylamine (182 μL, 1.04 mmol) under ice-cooled conditions. After the reaction mixture was stirred at room temperature for 1 h, the reaction mixture was purified by silica gel column chromatography (hexane/ethyl acetate=50/50 to 10/90) to obtain the title compound (79.2 mg, 62%) as an orange solid having the following characteristics.
$^1$H-NMR (CDCl$_3$) δ(ppm): 1.31 (s, 6H), 3.14 (s, 2H), 4.29 (s, 2H), 6.44 (d, J=8.2 Hz, 1H), 6.93-6.96 (m, 2H), 7.35 (dd, J=4.8, 7.8 Hz, 1H), 7.48 (d, J=9.0 Hz, 2H), 7.74 (d, J=7.8 Hz, 1H), 8.31 (d, J=9.0 Hz, 2H), 8.55 (dd, J=2.0, 4.8 Hz, 1H), 8.61 (d, J=2.0 Hz, 1H). MS (ESI+) m/z 420 (M+1).

(2) Synthesis of 1-(3-pyridylmethyl)-3,3-dimethylindolin-5-yl 2-(furfurylthio)ethylcarbamate To a suspension of 1-(3-pyridylmethyl)-3,3-dimethylindolin-5-yl 4-nitrophenylcarbonate (20 mg, 0.05 mmol) in 1 mL of acetonitrile was added 2-(furfurylthio)ethylamine (8 μL, 0.06 mmol). After the reaction mixture was stirred for 1 h, the reaction mixture was concentrated in vacuo, and the residue was purified by silica gel column chromatography (hexane/ethyl acetate=90/10 to 0/100) to obtain the title compound (11.6 mg, 56%) as a white solid having the following characteristics. $^1$H-NMR (CDCl$_3$) δ(ppm): 1.28 (s, 6H), 2.71 (t, J=6.4 Hz, 2H), 3.07 (s, 2H), 3.41 (dt, J=6.2, 6.3 Hz, 2H), 3.76 (s, 2H), 4.23 (s, 2H), 5.34 (m, 1H), 6.22 (d, J=3.0 Hz, 1H), 6.32 (m, 1H), 6.41 (m, 1H), 6.79 (m, 1H), 6.80 (br s, 1H), 7.28 (dd, J=4.9, 7.7 Hz, 1H), 7.37 (br s, 1H), 7.69 (d, J=7.8 Hz, 1H), 8.54 (br d, J=5 Hz, 1H), 8.60 (d, J=1.5 Hz, 1H). MS (ESI+) m/z 438 (M+1).

Example 201

Synthesis of 1-(3-pyridylmethyl)-3,3-dimethylindolin-5-yl 4-tetrahydropyranylmethylcarbamate The title compound was synthesized from 1-(3-pyridylmethyl)-3,3-dimethylindolin-5-yl 4-nitrophenylcarbonate (20.0 mg, 0.05 mmol) using the same procedure employed for Example 200 (2), but with 4-aminomethyltetrahydropyran instead of 2-(furfurylthio)ethylamine. The product was obtained as a white solid (9.5 mg, 32%) having the following characteristics.
$^1$H-NMR (CDCl$_3$) δ(ppm): 1.28 (s, 6H), 1.36 (m, 2H), 1.66 (d, J=13 Hz, 2H), 1.81 (m, 1H), 3.07 (s, 2H), 3.16 (t, J=6.5 Hz, 2H), 3.40 (br t, J=11 Hz, 2H), 4.00 (dd, J=4.11 Hz, 2H), 4.23 (s, 2H), 5.08 (m, 1H), 6.41 (d, J=8.1 Hz, 1H), 6.79 (dd, J=2.8 Hz, 1H), 6.80 (br s, 1H), 7.28 (dd, J=4.8, 7.7 Hz, 1H), 7.69 (d, J=7.8 Hz, 1H), 8.54 (br d, J=4 Hz, 1H), 8.60 (br s, 1H). MS (ESI+) m/z 396 (M+1).

Example 202

Synthesis of 1-(3-pyridylmethyl)-3,3-dimethylindolin-5-yl 3-tetrahydrofurylmethylcarbamate The title compound was synthesized from 1-(3-pyridylmethyl)-3,3-dimethylindolin-5-yl 4-nitrophenylcarbonate (20.0 mg, 0.05 mmol) using the same procedure employed for Example 200 (2), but with 3-tetrahydrofurylmethylamine instead of 2-(furfurylthio)ethylamine. The product was obtained as a white solid (4.6 mg, 25%) having the following characteristics.
MS (ESI+) m/z 382 (M+1).

Example 203

Synthesis of 1-(3-pyridylmethyl)-3,3-dimethylindolin-5-yl 2-(2,4-dichlorophenyl)ethylcarbamate The title compound was synthesized from 1-(3-pyridylmethyl)-3,3-dimethylindolin-5-yl 4-nitrophenylcarbonate (20.0 mg, 0.05 mmol) using the same procedure employed for Example 200 (2), but with 2-(2,4-dichlorophenyl)ethylamine instead of 2-(furfurylthio)ethylamine. The product was obtained as a white solid (7.1 mg, 32%) having the following characteristics.
$^1$H-NMR (CDCl$_3$) δ(ppm): 1.29 (s, 6H), 3.00 (t, J=7 Hz, 2H), 3.07 (s, 2H), 3.50 (dt, J=7, 7 Hz, 2H), 4.23 (s, 2H), 5.04 (m, 1H), 6.40 (d, J=8.9 Hz, 1H), 6.76 (dd, J=1.9 Hz, 1H), 6.77 (br s, 1H), 7.15-7.25 (m, 2H), 7.28 (dd, J=4.8, 7.7 Hz, 1H), 7.40 (d, J=1 Hz, 1H), 7.69 (d, J=7.8 Hz, 1H), 8.53 (dd, J=1.4, 4.7 Hz, 1H), 8.60 (d, J=1.7 Hz, 1H). MS (ESI+) m/z 470 (M+1).

Example 204

Synthesis of 1-(4-pyridylmethyl)-3,3-dimethylindolin-5-yl 4-tetrahydropyranylmethylcarbamate

(1) Synthesis of 1-(4-pyridylmethyl)-3,3-dimethylindolin-5-yl 4-nitrophenylcarbonate To a suspension of 1-(4-pyridylmethyl)-3,3-dimethylindolin-5-ol dihydrochloride (100.0 mg, 0.30 mmol) in 1 mL of dry tetrahydrofuran was added 4-nitrophenyl chloroformate (68 mg, 0.33 mmol) and diisopropylethylamine (182 μL, 0.52 mmol) under ice-cooled conditions. After the reaction mixture was stirred at room temperature for 1 h, the reaction mixture was purified by silica gel column chromatography (hexane/ethyl acetate=50/50 to 10/90) to obtain the title compound (64.9 mg, 25%) as an orange solid having the following characteristics.
$^1$H-NMR (CDCl$_3$) δ(ppm): 1.35 (s, 6H), 3.20 (s, 2H), 4.27 (s, 2H), 6.34 (d, J=8.4 Hz, 1H), 6.90-6.95 (m, 2H), 7.33 (d, J=5.4 Hz, 2H), 7.48 (d, J=9.0 Hz, 2H), 8.31 (d, J=9.0 Hz, 2H), 8.58 (d, J=5.4 Hz, 2H). MS (ESI+) m/z 420 (M+1).

(2) Synthesis of 1-(4-pyridylmethyl)-3,3-dimethylindolin-5-yl 4-tetrahydropyranylethylcarbamate To a suspension of 1-(4-pyridylmethyl)-3,3-dimethylindolin-5-yl 4-nitrophenylcarbonate (16 mg, 0.04 mmol) in 1 mL of acetonitrile was added 4-aminomethyltetrahydropyran (7 μL, 0.06 mmol). After the reaction mixture was stirred for 1 h, the reaction mixture was concentrated in vacuo, and the residue was purified by silica gel column chromatography (hexane/ethyl acetate=50/50 to 10/90) to obtain the title compound (9.8 mg, 65%) as a white solid having the following characteristics.
$^1$H-NMR (CDCl$_3$) δ(ppm): 1.32 (s, 6H), 1.36 (m, 2H), 1.66 (d, J=13 Hz, 2H), 1.80 (m, 1H), 3.13 (s, 2H), 3.16 (t, J=6.5 Hz, 2H), 3.39 (br t, J=11 Hz, 2H), 4.00 (dd, J=4.11 Hz, 2H), 4.22 (s, 2H), 5.10 (m, 1H), 6.31 (d, J=8.4 Hz, 1H), 6.76 (dd, J=2.3, 8.4 Hz, 1H), 6.81 (d, J=2.3 Hz, 1H), 7.29 (d, J=5.8 Hz, 1H), 8.56 (d, J=5.8 Hz, 2H). MS (ESI+) m/z 396 (M+1).

Example 205

Synthesis of 1-(4-pyridylmethyl)-3,3-dimethylindolin-5-yl 3-tetrahydrofurylmethylcarbamate The title compound was synthesized from 1-(4-pyridylmethyl)-3,3-dimethylindolin-5-yl 4-nitrophenylcarbonate (16 mg, 0.04 mmol) using the same procedure employed for Example 204 (2), but with 3-tetrahydrofurylmethylamine instead of 4-aminomethyltetrahydropyran. The product was obtained as a white solid (9.3 mg, 64%) having the following characteristics.
$^1$H-NMR (CDCl$_3$) δ(ppm): 1.32 (s, 6H), 1.67 (m, 1H), 2.07 (m, 1H), 2.53 (m, 1H), 3.13 (s, 2H), 3.28 (m, 2H), 3.58 (m, 1H), 3.76 (m, 1H), 3.8-4.0 (m, 2H), 4.22 (s, 2H), 5.16 (m, 1H), 6.31 (d, J=8.4 Hz, 1H), 6.77 (dd, J=2.3, 8.4 Hz, 1H), 6.81 (d, J=2.3 Hz, 1H), 7.29 (d, J=5.8 Hz, 1H), 8.56 (d, J=5.8 Hz, 2H). MS (ESI+) m/z 382 (M+1).

Example 206

Synthesis of 1-(4-pyridylmethyl)-3,3-dimethylindolin-5-yl 2-(furfurylthio)ethylcarbamate The title compound was synthesized from 1-(4-pyridylmethyl)-3,3-dimethylindolin-5-yl 4-nitrophenylcarbonate (16 mg, 0.04 mmol) using the same procedure employed for Example 204 (2), but with 2-(furfurylthio)ethylamine instead of 4-aminomethyltetrahydropyran. The product was obtained as a white solid (11.4 mg, 68%) having the following characteristics.
$^1$H-NMR (CDCl$_3$) δ(ppm): 1.32 (s, 6H), 2.71 (t, J=6.4 Hz, 2H), 3.13 (s, 2H), 3.41 (dt, J=6.2, 6.3 Hz, 2H), 3.76 (s, 2H), 4.22 (s, 2H), 5.35 (m, 1H), 6.22 (d, J=3.0 Hz, 1H), 6.30 (d, J=8.4 Hz, 1H), 6.32 (m, 1H), 6.77 (dd, J=2.2, 8.4 Hz, 1H), 6.81 (d, J=2.2 Hz, 1H), 7.29 (d, J=5.4 Hz, 1H), 7.37 (br s, 1H), 8.56 (d, J=5.9 Hz, 2H). MS (ESI+) m/z 438 (M+1).

Example 207

Synthesis of 1-(4-pyridylmethyl)-3,3-dimethylindolin-5-yl 2-(2,4-dichlorophenyl)ethylcarbamate The title compound was synthesized from 1-(4-pyridylmethyl)-3,3-dimethylindolin-5-yl 4-nitrophenylcarbonate (16 mg, 0.04 mmol) using the same procedure employed for Example 204 (2), but with 2-(2,4-dichlorophenyl)ethylamine instead of 4-aminomethyltetrahydropyran. The product was obtained as a white solid (11.6 mg, 65%) having the following characteristics.
$^1$H-NMR (CDCl$_3$) δ(ppm): 1.32 (s, 6H), 3.00 (t, J=7 Hz, 2H), 3.13 (s, 2H), 3.50 (dt, J=7, 7 Hz, 2H), 4.22 (s, 2H), 5.06 (m, 1H), 6.30 (d, J=8.3 Hz, 1H), 6.75 (dd, J=2, 8.3 Hz, 1H), 6.78 (d, J=2 Hz, 1H), 7.15-7.25 (m, 2H), 7.29 (d, J=5.2 Hz, 1H), 7.40 (br s, 1H), 8.56 (d, J=5.3 Hz, 2H). MS (ESI+) m/z 470 (M+1).

Example 208

Synthesis of 1-benzylindolin-5-yl (1-methyl-4-piperidinyl)methylcarbamate (1) Synthesis of 1-benzylindolin-5-yl-4-nitrophenylcarbonate To a suspension of 1-benzylindolin-5-ol monohydrochloride (200.0 mg, 0.76 mmol) in 5 mL of dry tetrahydrofuran was added 4-nitrophenyl chloroformate (200 mg, 0.99 mmol) and diisopropylethylamine (273 μL, 1.6 mmol) under ice-cooled conditions. After the reaction mixture was stirred at room temperature for 1 h, the reaction mixture was purified by silica gel column chromatography (hexane/ethyl acetate=100/0 to 80120) to obtain the title compound (125.9 mg, 42%) as an orange solid having the following characteristics.
MS (ESI+) m/z 391 (M+1).

(2) Synthesis of 1-benzylindolin-5-yl(1-methyl-4-piperidinyl)methylcarbamate

To a suspension of 1-benzylindolin-5-yl 4-nitrophenylcarbonate (20 mg, 0.05 mmol) in 1 mL of acetonitrile was added 4-aminomethyl-1-methylpiperidine (10 μL, 0.06 mmol). After the reaction mixture was stirred for 1 h, the reaction mixture was concentrated in vacuo, and the residue was purified by silica gel column chromatography (hexane/ethyl acetate=50/50 to 10/90) to obtain the title compound (10.7 mg, 55%) as a white solid having the following characteristics.
$^1$H-NMR (CDCl$_3$) δ(ppm): 1.2-1.8 (m, 5H), 1.92 (t, J=12 Hz, 2H), 2.87 (d, J=12 Hz, 2H), 2.94 (t, J=8.4 Hz, 2H), 3.15 (t, J=6.4 Hz, 2H), 3.31 (t, J=8.4 Hz, 2H), 4.21 (s, 2H), 5.03 (br s, 1H), 6.40 (d, J=8.4 Hz, 1H), 6.75 (dd, J=2.4, 8.4 Hz, 1H), 6.85 (d, J=2.4 Hz, 1H), 7.2-7.4 (m, 5H). MS (ESI+) m/z 380 (M+1).

Example 209

Synthesis of 1-(4-pyridylmethyl)indolin-5-yl cyclohexylmethylcarbamate (1) Synthesis of 1-(4-pyridylmethyl)indolin-5-ol The title compound was synthesized from 5-methoxyindole (1 g, 6.8 mmol) using the same procedure employed for Example 147 (1), but with 4-pyridinecarboxyaldehyde instead of 2-pyridinecarboxyaldehyde. The product was obtained as a white solid (1.53 g, 100%) having the following characteristics.
MS (ESI+) m/z 227 (M+1).

(2) Synthesis of 1-(4-pyridylmethyl)indolin-5-yl-4-nitrophenylcarbonate

To a suspension of 1-(4-pyridylmethyl)indolin-5-ol (500 mg, 2.2 mmol) in 5 mL of dichloromethane was added 4-nitrophenyl chloroformate (668 mg, 3.3 mmol) and triethylamine (370 μL, 2.65 mmol) under ice-cooled conditions. After the reaction mixture was stirred at room temperature for 1 h, the reaction mixture was purified by silica gel column chromatography (hexane/ethyl acetate=70/30 to 0/100) to obtain the title compound (205 mg, 24%) as an orange solid having the following characteristics.
$^1$H-NMR (CDCl$_3$) δ(ppm): 3.06 (t, J=8.3 Hz, 2H), 3.30 (t, J=8.3 Hz, 2H), 4.26 (s, 2H), 6.34 (d, J=8.4 Hz, 1H), 6.82 (dd, J=2.4, 8.4 Hz, 1H), 7.02 (s, 1H), 7.31 (d, J=5.4 Hz, 2H), 7.47 (d, J=9.0 Hz, 2H), 8.31 (d, J=9.0 Hz, 2H), 8.58 (d, J=5.4 Hz, 2H). MS (ESI+) m/z 392 (M+1).

(3) Synthesis of 1-(4-pyridylmethyl)indolin-5-yl cyclohexylmethylcarbamate

To a suspension of 1-(4-pyridylmethyl)indolin-5-yl 4-nitrophenylcarbonate (50 mg, 0.13 mmol) in 1 mL of acetonitrile was added aminomethylcyclohexane (20 μL, 0.16 mmol). After the reaction mixture was stirred for 1 h, the reaction mixture was concentrated in vacuo, and the residue was purified by silica gel column chromatography (hexane/ethyl acetate=20/80 to 0/100) to obtain the title compound (29.3 mg, 63%) as a white solid having the following characteristics.
$^1$H-NMR (CDCl$_3$) δ(ppm): 0.97 (t, J=10 Hz, 2H), 1.1-1.3 (m, 3H), 1.4-1.6 (m, 1H), 1.6-1.8 (m, 5H), 3.04 (t, J=8.4 Hz, 2H), 3.20 (t, J=6.4 Hz, 2H), 3.38-3.48 (m, 4H), 4.04 (dd, J=3.8, 12 Hz, 2H), 4.25 (s, 2H), 4.99 (br s, 1H), 6.31 (d, J=8.4 Hz, 1H), 6.76 (dd, J=2.4, 8.4 Hz, 1H), 6.89 (d, J=2.4 Hz, 1H), 7.30 (d, J=5.3 Hz, 2H), 8.56 (d, J=5.3 Hz, 2H). MS (ESI+) m/z 366 (M+1).

Example 210

Synthesis of 1-(4-pyridylmethyl)indolin-5-yl-4-tetrahydropyranylmethylcarbamate

The title compound was synthesized from 1-(4-pyridylmethyl)indolin-5-yl 4-nitrophenylcarbonate (50 mg, 0.13 mmol) using the same procedure employed for Example 209 (3), but with 4-aminomethyltetrahydropyran instead of aminomethylcyclohexane. The product was obtained as a white solid (27.6 mg, 59%) having the following characteristics.

$^1$H-NMR (CDCl$_3$) δ(ppm): 1.39 (dq, J=4.5, 12 Hz, 2H), 1.69 (d, J=12 Hz, 2H), 1.7-1.9 (m, 1H), 3.00 (t, J=8.4 Hz, 2H), 3.09 (t, J=6.4 Hz, 2H), 3.4-3.5 (m, 4H), 4.04 (dd, J=3.8 Hz, 12 Hz, 2H), 4.21 (s, 2H), 5.11 (t, J=5.7 Hz, 1H), 6.35 (d, J=8.4 Hz, 1H), 6.79 (dd, J=2.0, 8.4 Hz, 1H), 6.93 (d, J=2.0 Hz, 1H), 7.34 (d, J=5.9 Hz, 2H), 8.60 (d, J=5.9 Hz, 2H). MS (ESI+) m/z 368 (M+1).

Example 211

Synthesis of 1-(3-pyridylmethyl)indolin-5-yl cyclohexylmethylcarbamate (1) Synthesis of 1-(3-pyridylmethyl)indolin-5-ol The title compound was synthesized from 5-methoxyindole (1 g, 6.8 mmol) using the same procedure employed for Example 147 (1), but with 3-pyridinecarboxyaldehyde instead of 2-pyridinecarboxyaldehyde. The product was obtained as a white solid (790 mg, 52%) having the following characteristics.

MS (ESI+) m/z 403 (M+1).

(2) Synthesis of 1-(3-pyridylmethyl)indolin-5-yl 4-nitrophenylcarbonate

The title compound was synthesized from a suspension of 1-(3-pyridylmethyl)indolin-5-ol (790 mg, 3.5 mmol) in 8 mL of dichloromethane using the same procedure employed for Example 209 (2). The product was obtained as an orange solid (952 mg, 70%) having the following characteristics.

$^1$H-NMR (CDCl$_3$) δ(ppm): 3.01 (t, J=8.2 Hz, 2H), 3.37 (t, J=8.2 Hz, 2H), 4.26 (s, 2H), 6.45 (d, J=8.2 Hz, 1H), 6.82 (dd, J=2.4, 8.2 Hz, 1H), 7.00 (s, 1H), 7.29 (dd, J=4.8, 7.8 Hz, 1H), 7.47 (d, J=9.0 Hz, 2H), 7.70 (d, J=7.8 Hz, 1H), 8.31 (d, J=9.0 Hz, 2H), 8.55 (dd, J=2.0, 4.8 Hz, 1H), 8.61 (d, J=2.0 Hz, 1H). MS (ESI+) m/z 392 (M+1).

(3) Synthesis of 1-(3-pyridylmethyl)indolin-5-yl cyclohexylmethylcarbamate

To a suspension of 1-(3-pyridylmethyl)indolin-5-yl 4-nitrophenylcarbonate (50 mg, 0.13 mmol) in 1 mL of acetonitrile was added aminomethylcyclohexane (20 μL, 0.16 mmol). After the reaction mixture was stirred for 1 h, the reaction mixture was concentrated in vacuo, and the residue was purified by silica gel column chromatography (hexane/ethyl acetate=20/80 to 0/100) to obtain the title compound (44.3 mg, 95%) as a white solid having the following characteristics.

$^1$H-NMR (CDCl$_3$) δ(ppm): 0.97 (t, J=10 Hz, 2H), 1.1-1.3 (m, 3H), 1.4-1.6 (m, 1H), 1.6-1.8 (m, 5H), 2.96 (t, J=8.2 Hz, 2H), 3.09 (t, J=6.4 Hz, 2H), 3.30 (d, J=8.2 Hz, 2H), 4.22 (s, 2H), 4.99 (br s, 1H), 6.41 (d, J=8.4 Hz, 1H), 6.75 (dd, J=2.4, 8.4 Hz, 1H), 6.86 (d, J=2.4 Hz, 1H), 7.27 (dd, J=4.8, 7.9 Hz, 1H), 7.70 (dt, J=1.8, 7.9 Hz, 1H), 8.54 (dd, J=1.8, 4.8 Hz, 1H), 8.60 (d, J=1.8 Hz, 1H). MS (ESI+) m/z 366 (M+1).

Example 212

Synthesis of 1-(3-pyridylmethyl)indolin-5-yl 4-tetrahydropyranylmethylcarbamtate The title compound was synthesized from 1-(3-pyridylmethyl)indolin-5-yl 4-nitrophenylcarbonate (50 mg, 0.13 mmol) using the same procedure employed for Example 211 (3), but with 4-aminomethyltetrahydropyran instead of aminomethylcyclohexane. The product was obtained as a white solid (44.1 mg, 94%) having the following characteristics.

$^1$H-NMR (CDCl$_3$) δ(ppm): 1.35 (dq, J=4.5, 12 Hz, 2H), 1.65 (d, J=12 Hz, 2H), 1.75-1.85 (m, 1H), 2.96 (t, J=8.4 Hz, 2H), 3.16 (1, J=6.4 Hz, 2H), 3.31 (t, J=8.4 Hz, 2H), 3.39 (dt, J=1.5, 12 Hz, 2H), 3.99 (dd, J=3.7, 12 Hz, 2H), 4.22 (s, 2H), 5.07 (t, J=5.7 Hz, 1H), 6.41 (d, J=8.4 Hz, 1H), 6.77 (dd, J=2.4, 8.4 Hz, 1H), 6.88 (d, J=2.4 Hz, 1H), 7.27 (dd, J=4.8, 7.9 Hz, 1H), 7.70 (d, J=7.8 Hz, 1H), 8.54 (dd, J=1.6, 4.8 Hz, 1H), 8.60 (d, J=1.6 Hz, 1H). MS (ESI+) m/z 368 (M+1).

Example 213

Synthesis of 1-(2-pyridylmethyl)indolin-5-yl 4-tetrahydropyranylmethylcarbamate (1) Synthesis of 1-(2-pyridylmethyl)indolin-5-yl 4-nitrophenylcarbonate To a suspension of 1-(2-pyridylmethyl)indolin-5-ol dihydrochloride (500 mg, 1.7 mmol) in 8 mL of dichloromethane was added 4-nitrophenyl chloroformate (505 mg, 2.55 mmol) and triethylamine (815 μL, 5.95 mmol) under ice-cooled conditions. After the reaction mixture was stirred at room temperature for 1 h, the reaction mixture was purified by silica gel column chromatography (hexane/ethyl acetate=50/50 to 30/70) to obtain the title compound (403 mg, 61%) as an orange solid having the following characteristics.

$^1$H-NMR (CDCl$_3$) δ(ppm): 3.06 (t, J=8.4 Hz, 2H), 3.52 (t, J=8.4 Hz, 2H), 4.40 (s, 2H), 6.39 (d, J=8.5 Hz, 1H), 6.89 (dd, J=2.4, 8.4 Hz, 1H), 7.00 (d, J=2.4 Hz, 1H), 7.20 (dd, J=5.5, 7.0 Hz, 1H), 7.40 (d, J=7.8 Hz, 1H), 7.47 (d, J=9.2 Hz, 2H), 7.67 (dt, J=1.8, 7.8 Hz, 1H), 8.31 (d, J=9.2 Hz, 2H), 8.60 (ddd, J=1.0, 1.0, 4.8 Hz, 1H). MS (ESI+) m/z 392 (M+1).

(2) Synthesis of 1-(2-pyridylmethyl)indolin-5-yl 4-tetrahydropyranylmethylcarbamate To a suspension of 1-(2-pyridylmethyl)indolin-5-yl 4-nitrophenylcarbonate (50 mg, 0.13 mmol) in 1 mL of acetonitrile was added 4-aminomethyltetrahydropyran (18 μL, 0.16 mmol). After the reaction mixture was stirred for 1 h, the reaction mixture was concentrated in vacuo, and the residue was purified by silica gel column chromatography (hexane/ethyl acetate=20/80 to 0/100) to obtain the title compound (39.4 mg, 84%) as a white solid having the following characteristics.

$^1$H-NMR (CDCl$_3$) δ(ppm): 1.35 (dq, J=4.5, 12 Hz, 2H), 1.65 (d, J=12 Hz, 2H), 1.75-1.85 (m, 1H), 3.01 (t, J=8.4 Hz, 2H), 3.15 (t, J=6.4 Hz, 2H), 3.39 (dt, J=1.5, 12 Hz, 2H), 3.46 (t, J=8.4 Hz, 2H), 3.99 (dd, J=3.7, 12 Hz, 2H), 4.22 (s, 2H), 5.07 (t, J=5.7 Hz, 1H), 6.34 (d, J=8.4 Hz, 1H), 6.74 (dd, J=2.4, 8.4 Hz, 1H), 6.87 (d, J=2.4 Hz, 1H), 7.18 (dd, J=5.5, 7.0 Hz, 1H), 7.41 (d, J=7.8 Hz, 1H), 7.65 (dt, J=1.8, 7.8 Hz, 1H), 8.57 (ddd, J=1.0, 1.0, 4.8 Hz, 1H). MS (ESI+) m/z 368 (M+1).

Example 214

Synthesis of O-(1-benzylindolin-5-yl)-N-(cyclohexylmethyl)-N-methylcarbamate (1) Synthesis of tert-butyl N-(cyclohexylmethyl)carbamate To a solution of cyclohexylmethylamine (500 mg, 4.4 mmol) in 5.0 mL of tetrahydrofuran was added triethylamine (537 mg, 5.3 mmol) and di-tert-butyl dicarbonate (1.0 g, 4.6 mmol) under ice-cooled conditions. After being stirred for 1 h, the reaction mixture was added water, and diluted with ethyl acetate. The separated organic layer was washed with brine, and dried over $Na_2SO_4$. After filtration, the filtrate was concentrated in vacuo to obtain the title compound (799 mg, 85%).
$^1$H-NMR (CDCl$_3$) δ(ppm): 0.80-1.0 (m, 2H), 1.1-1.3 (m, 3H), 1.44 (s, 9H), 1.6-1.8 (m, 6H), 2.96 (t, J=6.4 Hz, 1H), 4.57 (br s, 1H).

(2) Synthesis of tert-butyl N-(cyclohexylmethyl)-N-methyl carbamate

To a solution of tert-butyl N-(cyclohexylmethyl)carbamate (790 mg, 3.7 mmol) and iodomethane (588 mg, 4.1 mmol) in 8.0 mL of tetrahydrofuran was added sodium hydride (60%, 4.4 mmol) under ice-cooled conditions. After the reaction mixture was stirred at room temperature overnight, the solution was added with saturated $NH_4Cl$ aqueous solution, and diluted with ethyl acetate. The separated organic layer was washed with brine, and dried over $Na_2SO_4$. After filtration, the filtrate was concentrated in vacuo, and the residue was purified by silica gel column chromatography (hexane/ethyl acetate=100/0 to 80/20) to obtain the title compound (379 mg, 45%).
$^1$H-NMR (CDCl$_3$) δ(ppm): 0.80-1.0 (m, 2H), 1.1-1.3 (m, 3H), 1.45 (s, 9H), 1.6-1.8 (m, 6H), 2.84 (s, 3H), 3.03 (br s, 1H).

(3) Synthesis of N-(cyclohexylmethyl)-N-methylamine monohydrochloride

To a solution of tert-butyl N-(cyclohexylmethyl)-N-methylcarbamate (370 mg, 1.6 mmol) in 4.0 mL of ethyl acetate was added 4 M HCl-ethyl acetate (4 mL). After being stirred at room temperature for 1.5 h, the reaction mixture was concentrated in vacuo, and the residue was rinsed with hexane to obtain the title compound (266 mg, 100%).
$^1$H-NMR (DMSO-d6) δ(ppm): 0.80-1.0 (m, 2H), 1.1-1.3 (m, 3H), 1.6-1.8 (m, 6H), 2.70 (d, J=6.9 Hz, 2H), 3.35 (s, 3H), 8.81 (br s, 2H).

(4) Synthesis of O-(1-benzylindolin-5-yl)-N-(cyclohexylmethyl)-N-methylcarbamate To a solution of 1-benzylindolin-5-yl 4-nitrophenylcarbonate (30 mg, 0.08 mmol) and N-(cyclohexylmethyl)-N-methylamine monohydrochloride (15 mg, 0.12 mmol) in 1 mL of acetonitrile was added triethylamine (13 μL, 0.12 mmol) under ice-cooled conditions. After the reaction mixture was stirred for 1 h, the reaction mixture was concentrated in vacuo, and the residue was purified by silica gel column chromatography (hexane/ethyl acetate=100/0 to 80/20) to obtain the title compound (29.0 mg, 100%) as a colorless sticky oil having the following characteristics.
$^1$H-NMR (CDCl$_3$) δ(ppm): 0.98 (m, 2H), 1.1-1.3 (m, 3H), 1.45-1.55 (m, 1H), 1.6-1.8 (m, 5H), 2.94 (t, J=8.2 Hz, 2H), 2.97 (s, 1.5H, carbamoyl-N-Me), 3.04 (s, 1.5H, carbamoyl-N-Me), 3.17 (d, J=6.9 Hz, 1H), 3.24 (d, J=7.1 Hz, 1H), 3.30 (t, J=8.2 Hz, 2H), 4.21 (s, 2H), 6.42 (d, J=8.4 Hz, 1H), 6.74 (m, 1H), 6.83 (br s, 0.5H), 6.86 (br s, 0.5H), 7.23-7.38 (m, 5H). MS (ESI+) m/z 379 (M+1).

Example 215

Synthesis of O-(1-benzylindolin-5-yl)-N-methyl-N-(4-tetrahydropyranylmethyl)carbamate (1) Synthesis of tert-butyl N-(4-tetrahydropyranylmethyl)carbamate To a solution of 4-aminomethyltetrahydropyran (500 mg, 4.4 mmol) in 5.0 mL of tetrahydrofuran was added triethylamine (537 mg, 5.3 mmol) and di-tert-butyl dicarbonate (1.0 g, 4.6 mmol) under ice-cooled conditions. After being stirred for 1 h, the reaction mixture was added water, and diluted with ethyl acetate. The separated organic layer was washed with brine, and dried over $Na_2SO_4$. After filtration, the filtrate was concentrated in vacuo, and the residue was purified by silica gel column chromatography (hexane/ethyl acetate=80120 to 50/50) to obtain the title compound (855 mg, 91%).
$^1$H-NMR (CDCl$_3$) δ(ppm): 1.2-1.4 (m, 2H), 1.44 (s, 9H), 1.6-1.8 (m, 3H), 3.02 (t, J=6.4 Hz, 1H), 3.37 (br t, J=11 Hz, 2H), 3.97 (dd, J=4.11 Hz, 2H), 4.62 (br s, 1H).

(2) Synthesis of tert-butyl N-methyl-N-(4-tetrahydropyranylmethyl)carbamate

To a solution of tert-butyl N-(4-tetrahydropyranylmethyl)carbamate (610 mg, 2.8 mmol) and iodomethane (805 mg, 5.6 mmol) in 6.0 mL of N,N-dimethylformamide was added sodium hydride (60%, 227 mg, 5.6 mmol) under ice-cooled conditions. After the reaction mixture was stirred at room temperature overnight, the solution was added with saturated $NH_4Cl$ aqueous solution, and diluted with ethyl acetate. The separated organic layer was washed with brine, and dried over $Na_2SO_4$. After filtration, the filtrate was concentrated in vacuo, and the residue was purified by silica gel column chromatography (hexane/ethyl acetate=90/10 to 70/30) to obtain the title compound (607 mg, 95%).
$^1$H-NMR (CDCl$_3$) δ(ppm): 1.2-1.4 (m, 2H), 1.46 (s, 9H), 1.55 (br d, J=13 Hz, 2H), 1.9-2.0 (br s, 1H), 2.86 (s, 3H), 3.10 (d, J=7.2 Hz, 2H), 3.36 (dt, J=2.0, 11 Hz, 1H), 3.98 (br d, J=11 Hz, 2H).

(3) Synthesis of N-methyl-N-(4-tetrahydropyranylmethyl)amine monohydrochloride

To a solution of tert-butyl N-methyl-N-(4-tetrahydropyranylmethyl)carbamate (600 mg, 2.6 mmol) in 4.0 mL of ethyl acetate was added 4 M HCl-ethyl acetate (4 mL). After being stirred at room temperature for 1.5 h, the reaction mixture was concentrated in vacuo, and the residue was rinsed with hexane to obtain the title compound (356 mg, 82%).

(4) Synthesis of O-(1-benzylindolin-5-yl)-N-methyl-N-(4-tetrahydropyranylmethyl)carbamate To a solution of 1-benzylindolin-5-yl 4-nitrophenylcarbonate (30 mg, 0.08 mmol) and N-methyl-N-(4-tetrahydropyranylmethyl)amine monohydrochloride (15 mg, 0.12 mmol) in 1 mL of acetonitrile was added triethylamine (13 µL, 0.12 mmol) under ice-cooled conditions. After the reaction mixture was stirred for 1 h, the reaction mixture was concentrated in vacuo, and the residue was purified by silica gel column chromatography (hexane/ethyl acetate=85/15 to 65/35) to obtain the title compound (23.2 mg, 79%) as a colorless sticky oil having the following characteristics.

¹H-NMR (CDCl₃) δ(ppm): 1.39 (m, 2H), 1.62 (m, 2H), 1.96 (m, 1H), 2.95 (t, J=8.2 Hz, 2H), 2.98 (s, 1.5H, carbamoyl-N-Me), 3.05 (s, 1.5H, carbamoyl-N-Me), 3.23 (d, J=7.2 Hz, 1H), 3.27-3.35 (m, 3H), 3.39 (br t, J=11 Hz, 2H), 4.00 (br t, J=11 Hz, 2H), 4.22 (s, 2H), 6.42 (d, J=8.4 Hz, 1H), 6.74 (m, 1H), 6.83 (br s, 0.5H), 6.85 (br s, 0.5H), 7.23-7.38 (m, 5H). MS (ESI+) m/z 381 (M+1).

Example 216

Synthesis of O-(1-benzyl-3,3-dimethylindolin-5-yl)-N-(cyclohexylmethyl)-N-methylcarbamate (1) Synthesis of 1-benzyl-3,3-dimethylindolin-5-yl 4-nitrophenylcarbonate To a suspension of 1-benzyl-3,3-dimethylindolin-5-ol monohydrochloride (200.0 mg, 0.69 mmol) in 1 mL of dry tetrahydrofuran was added 4-nitrophenyl chloroformate (68 mg, 1.56 mmol) and triethylamine (289 µL, 3.0 mmol) under ice-cooled conditions. After the reaction mixture was stirred at room temperature for 1 h, the reaction mixture was concentrated in vacuo, and the residue was purified by silica gel column chromatography (hexane/ethyl acetate=100/0 to 80/20) to obtain the title compound (282 mg, 98%) as an orange solid having the following characteristics.

MS (ESI+) m/z 419 (M+1).

(2) Synthesis of O-(1-benzyl-3,3-dimethylindolin-5-yl)-N-(cyclohexylmethyl)-N-methylcarbamate To a solution of 1-benzyl-3,3-dimethylindolin-5-yl 4-nitrophenylcarbonate (32 mg, 0.08 mmol) and N-(cyclohexylmethyl)-N-methylamine monohydrochloride (15 mg, 0.12 mmol) in 1 mL of acetonitrile was added triethylamine (13 µL, 0.12 mmol) under ice-cooled conditions. After the reaction mixture was stirred for 1 h, the reaction mixture was concentrated in vacuo, and the residue was purified by silica gel column chromatography (hexane/ethyl acetate=100/0 to 80/20) to obtain the title compound (30.1 mg, 97%) as a colorless sticky oil having the following characteristics.

¹H-NMR (CDCl₃) δ(ppm): 0.99 (m, 2H), 1.1-1.3 (m, 3H), 1.45-1.55 (m, 1H), 1.6-1.8 (m, 5H), 2.98 (s, 1.5H, carbamoyl-N-Me), 3.05 (s, 1.5H, carbamoyl-N-Me), 3.07 (s, 2H), 3.18 (d, J=7 Hz, 1H), 3.25 (d, J=7 Hz, 1H), 4.22 (s, 2H), 6.41 (d, J=8.2 Hz, 1H), 6.7-6.8 (m, 2H), 7.24-7.38 (m, 5H). MS (ESI+) m/z 407 (M+1).

Example 217

Synthesis of O-(1-benzyl-3,3-dimethylindolin-5-yl)-N-methyl-N-(4-tetrahydropyranylmethyl)carbamate To a solution of 1-benzyl-3,3-dimethylindolin-5-yl-4-nitrophenylcarbonate (32 mg, 0.08 mmol) and N-(cyclohexylmethyl)-N-methylamine monohydrochloride (15 mg, 0.12 mmol) in 1 mL of acetonitrile was added triethylamine (13 µL, 0.12 mmol) under ice-cooled conditions. After the reaction mixture was stirred for 1 h, the reaction mixture was concentrated in vacuo, and the residue was purified by silica gel column chromatography (hexane/ethyl acetate=85/15 to 65/35) to obtain the title compound (22.2 mg, 71%) as a colorless sticky oil having the following characteristics.

¹H-NMR (CDCl₃) δ(ppm): 1.29 (s, 6H), 1.39 (m, 2H), 1.65 (m, 2H), 1.97 (m, 1H), 3.01 (s, 1.5H, carbamoyl-N-Me), 3.08 (s, 2H), 3.09 (s, 1.5H, carbamoyl-N-Me), 3.24 (d, J=7.2 Hz, 1H), 3.31 (d, J=7.3 Hz, 1H), 3.40 (dt, J=4.11 Hz, 2H), 4.00 (br t, J=11 Hz, 2H), 4.22 (s, 2H), 6.40 (d, J=8.1 Hz, 1H), 6.7-6.8 (m, 2H), 7.23-7.37 (m, 5H). MS (ESI+) m/z 409 (M+1).

Example 218

Synthesis of N-methyl-O-[1-(2-pyridylmethyl)-3,3-dimethylindolin-5-yl]-N-(4-tetrahydropyranylmethyl)carbamate To a solution of 1-(2-pyridylmethyl)-3,3-dimethylindolin-5-yl 4-nitrophenylcarbonate (30 mg, 0.07 mmol) and N-methyl-N-(4-tetrahydropyranylmethyl)amine monohydrochloride (14.2 mg, 0.11 mmol) in 1 mL of acetonitrile was added triethylamine (12 µL, 0.11 mmol) under ice-cooled conditions. After the reaction mixture was stirred for 1 h, the reaction mixture was concentrated in vacuo, and the residue was purified by silica gel column chromatography (hexane/ethyl acetate=70/30 to 30/70) to obtain the title compound (24.6 mg, 84%) as a colorless sticky oil having the following characteristics.

¹H-NMR (CDCl₃) δ(ppm): 1.32 (s, 6H), 1.38 (m, 2H), 1.62 (m, 2H), 1.97 (m, 1H), 3.00 (s, 1.5H, carbamoyl-N-Me), 3.09 (s, 1.5H, carbamoyl-N-Me), 3.23 (s, 2H), 3.24 (m, 1H), 3.31 (d, J=7.3 Hz, 1H), 3.40 (dt, J=4.11 Hz, 2H), 4.00 (br t, J=11 Hz, 2H), 4.38 (s, 2H), 6.34 (d, J=8.3 Hz, 1H), 6.74 (m, 1H), 6.76 (br s, 0.5H), 6.80 (br s, 0.5H), 7.18 (dd, J=5, 7 Hz, 1H), 7.39 (d, J=7.7 Hz, 1H), 7.65 (dd, J=7.7, 7.7 Hz, 1H), 8.57 (br d, J=5 Hz, 1H). MS (ESI+) m/z 410 (M+1).

Example 219

Synthesis of N-methyl-O-[1-(3-pyridylmethyl)-3,3-dimethylindolin-5-yl]-N-(4-tetrahydropyranylmethyl)carbamate To a solution of 1-(3-pyridylmethyl)-3,3-dimethylindolin-5-yl 4-nitrophenylcarbonate (30 mg, 0.07 mmol) and N-methyl-N-(4-tetrahydropyranylmethyl)amine monohydrochloride (14.2 mg, 0.11 mmol) in 1 mL of acetonitrile was added triethylamine (12 µL, 0.11 mmol) under ice-cooled conditions. After the reaction mixture was stirred for 1 h, the reaction mixture was concentrated in vacuo, and the residue was purified by silica gel column chromatography (hexane/ethyl acetate=70/30 to 30/70) to obtain the title compound (29.3 mg, 100%) as a colorless sticky oil having the following characteristics.

¹H-NMR (CDCl₃) δ(ppm): 1.29 (s, 6H), 1.39 (m, 2H), 1.63 (m, 2H), 1.97 (m, 1H), 3.01 (s, 1.5H, carbamoyl-N-Me), 3.06 (s, 2H), 3.09 (s, 1.5H, carbamoyl-N-Me), 3.24 (d, J=7.2 Hz, 1H), 3.32 (d, J=7.4 Hz, 1H), 3.39 (dt, J=5, 11 Hz, 2H), 4.00 (br t, J=11 Hz, 2H), 4.23 (s, 2H), 6.41 (d, J=8.7 Hz, 1H), 6.75 (m, 1H), 6.76 (br s, 0.5H), 6.79 (br s, 0.5H), 7.28 (dd, J=4.8, 7.8 Hz, 1H), 7.69 (d, J=7.8 Hz, 1H), 8.54 (dd, J=1.4 Hz, 1H), 8.60 (br s, 1H). MS (ESI+) m/z 410 (M+1).

Example 220

Synthesis of N-methyl-O-[1-(4-pyridylmethyl)-3,3-dimethylindolin-5-yl]-N-(4-tetrahydropyranylmethyl)carbamate To a solution of 1-(4-pyridylmethyl)-3,3-dimethylindolin-5-yl 4-nitrophenylcarbonate (7.8 mg, 0.02 mmol) and N-methyl-N-(4-tetrahydropyranylmethyl)amine monohydrochloride (3.7 mg, 0.02 mmol) in 1 mL of acetonitrile was added triethylamine (3 µL, 0.02 mmol) under ice-cooled conditions. After the reaction mixture was stirred for 1 h, the reaction mixture was concentrated in vacuo, and the residue was purified by silica gel column chromatography (hexane/ethyl acetate=40/60 to 0/100) to obtain the title compound (7.6 mg, 100%) as a colorless sticky oil having the following characteristics.

$^1$H-NMR (CDCl$_3$) δ(ppm): 1.32 (s, 6H), 1.39 (m, 2H), 1.63 (m, 2H), 1.97 (m, 1H), 3.01 (s, 1.5H, carbamoyl-N-Me), 3.09 (s, 1.5H, carbamoyl-N-Me), 3.13 (s, 2H), 3.24 (d, J=7.2 Hz, 1H), 3.32 (d, J=7.4 Hz, 1H), 3.39 (dt, J=5, 11 Hz, 2H), 4.00 (br t, J=11 Hz, 2H), 4.23 (s, 2H), 6.31 (d, J=8.4 Hz, 1H), 6.75 (m, 1H), 6.77 (br s, 0.5H), 6.81 (br s, 0.5H), 7.31 (d, J=4.8 Hz, 1H), 8.57 (br s, 2H). MS (ESI+) m/z 410 (M+1).

Example 221

Synthesis of N,N-dimethyl-O-(1-benzylindolin-5-yl)carbamate

To a solution of 1-benzylindolin-5-ol (100 mg, 0.44 mmol), N,N-diisopropylethylamine (150 µL, 0.88 mmol) and 4-dimethylaminopyridine (5.4 mg, 44 µmol) in 1 mL of dry dichloromethane was added dimethylcarbamoyl chloride (57 mg, 0.53 mmol) at room temperature. After the reaction mixture was stirred at the same temperature overnight, the reaction mixture was washed with water. The separated organic layer was purified by silica gel column chromatography (hexane/ethyl acetate=100/0 to 60/40) to obtain the title compound (120.7 mg, 92%) having the following characteristics.

$^1$H-NMR (CDCl$_3$) δ(ppm): 2.96 (s, 3H), 2.96 (t, J=8.2 Hz, 2H), 3.06 (s, 3H), 3.34 (t, J=8.2 Hz, 2H), 4.24 (s, 2H), 6.42 (d, J=8.7 Hz, 1H), 6.72 (dd, J=2.4, 8.7 Hz, 1H), 6.83 (m, 1H), 7.25-7.42 (m, 5H). MS (ESI+) m/z 297.3 (M+1).

Example of Pharmacological Test 1

The pharmacological examples that suggest the utility of compounds (1) as medicine are shown below.

<In Vitro Assay for Choline Esterase Inhibition>

For measurement of esterase activity, brain homogenate and serum of mouse were used as choline esterase enzyme sources, and the method of Ellman et. al (Biochemical pharmacology 7: 88-95 1961) were referred. Compound of each example were diluted in dimethylsulfoxide.

In detail, acetylthiocholine or butyrylthiocholine as substrates, test compounds, and DNTB [5,5'-thiobis(2-nitrobenzoate)] were added to the mouse brain homogenate or serum, respectively.

After incubation, thiocholine was produced by enzyme reaction in the mixture, and then, the yellow product was formed by the reaction of thiocholine and DTNB. The activity of acetylcholine esterase (AChE) or butyrylcholine esterase (BuChE) was evaluated by determination of absorbance at 415 nm. From these results, 50% inhibition concentration value (IC$_{50}$) of each test compound was calculated. And the selectivity for BuChE inhibition of each compound was calculated by the ratio: IC$_{50}$ (AchE)/IC$_{50}$ (BuChE). The results are shown in table 1, 2 and 3.

TABLE 1

| Compound No. | BuChE inhibitory activity IC50 (nM) | AChE inhibitory activity IC50 (nM) | Ratio AChE/BuChE |
|---|---|---|---|
| Example 2 | 570 | >100000 | >180 |
| Example 3 | 1200 | >100000 | >83 |
| Example 7 | 900 | >100000 | >110 |
| Example 9 | 98 | >100000 | >1000 |
| Example 11 | 170 | >100000 | >590 |
| Example 12 | 290 | 11000 | 38 |
| Example 14 | 41 | 2700 | 66 |
| Example 15 | 13 | 1800 | 140 |
| Example 16 | 42 | 9800 | 230 |
| Example 17 | 16 | 8000 | 500 |
| Example 18 | 38 | 1800 | 47 |
| Example 19 | 190 | >100000 | >530 |
| Example 20 | 67 | >100000 | >1500 |
| Example 27 | 1100 | >100000 | >91 |
| Example 28 | 470 | >100000 | >210 |
| Example 31 | 17 | 4100 | 240 |
| Example 32 | 160 | >100000 | >630 |
| Example 33 | 350 | >100000 | >290 |
| Example 34 | 3 | >100000 | >33000 |
| Example 35 | 8 | 46000 | 5800 |
| Example 41 | 190 | 36000 | 190 |
| Example 42 | 23 | >100000 | >4300 |
| Example 43 | 170 | >100000 | >590 |
| Example 44 | 32 | >100000 | >3100 |
| Example 45 | 21 | >100000 | >4800 |
| Example 46 | 150 | >100000 | >670 |
| Example 47 | 82 | >100000 | >1200 |
| Example 49 | 12 | 6300 | 530 |
| Example 50 | 53 | >100000 | >1900 |
| Example 51 | 16 | 18000 | 1100 |
| Example 53 | 28 | 46000 | 1600 |
| Example 54 | 15 | >100000 | >6700 |
| Example 55 | 290 | >100000 | >340 |
| Example 57 | 34 | 69000 | 2000 |
| Example 60 | 130 | >100000 | >770 |
| Example 62 | 450 | >100000 | >220 |
| Example 65 | 700 | >100000 | >140 |
| Example 66 | 570 | >100000 | >180 |
| Example 67 | 1300 | >100000 | >77 |
| Example 75 | 770 | >100000 | >130 |

TABLE 2

| Compound No. | BuChE inhibitory activity IC50 (nM) | AChE inhibitory activity IC50 (nM) | Ratio AChE/BuChE |
|---|---|---|---|
| Example 78 | 820 | >100000 | >120 |
| Example 80 | 140 | >100000 | >710 |
| Example 85 | 420 | >100000 | >240 |
| Example 91 | 59 | >100000 | >1700 |
| Example 96 | 17 | >100000 | >5900 |
| Example 97 | 450 | >100000 | >220 |
| Example 98 | 12 | 1600 | 130 |
| Example 99 | 21 | 14000 | 670 |
| Example 100 | 7.3 | 1600 | 220 |
| Example 102 | 130 | 10000 | 77 |
| Example 103 | 110 | 9300 | 85 |
| Example 104 | 11 | 5500 | 500 |
| Example 113 | 160 | >100000 | >630 |
| Example 114 | 180 | 5200 | 29 |
| Example 115 | 10 | 12000 | 1200 |
| Example 116 | 45 | >100000 | >2200 |
| Example 117 | 24 | 7900 | 330 |
| Example 118 | 10 | >100000 | >10000 |
| Example 119 | 59 | 14000 | 240 |
| Example 120 | 24 | 8500 | 350 |
| Example 122 | 480 | >100000 | >210 |
| Example 127 | 610 | 750 | 1.2 |
| Example 131 | 210 | 1300 | 6.2 |
| Example 133 | 39 | >100000 | >2600 |
| Example 137 | 180 | >100000 | >560 |
| Example 138 | 900 | >100000 | >110 |

TABLE 2-continued

| Compound No. | BuChE inhibitory activity IC50 (nM) | AChE inhibitory activity IC50 (nM) | Ratio AChE/BuChE |
| --- | --- | --- | --- |
| Example 139 | 43 | 2700 | 63 |
| Example 140 | 110 | >100000 | >910 |
| Example 145 | 280 | >100000 | >360 |
| Example 146 | 180 | >100000 | >560 |
| Example 147 | 11 | 250 | 23 |
| Example 148 | 2 | 1200 | 600 |
| Example 149 | 58 | 2200 | 38 |
| Example 150 | 10 | 110 | 11 |
| Example 152 | 57 | 1100 | 19 |
| Example 153 | 91 | >100000 | >1100 |
| Example 155 | 15 | 57000 | 3800 |
| Example 156 | 510 | >100000 | >200 |
| Example 160 | 550 | >100000 | >180 |
| Example 161 | 150 | >100000 | >670 |
| Example 162 | 410 | >100000 | >240 |

TABLE 3

| Compound No. | BuChE inhibitory activity IC50 (nM) | AChE inhibitory activity IC50 (nM) | Ratio AChE/BuChE |
| --- | --- | --- | --- |
| Example 214 | 51 | >100000 | >2000 |
| Example 216 | 2.4 | 54000 | 23000 |
| Example 217 | 0.36 | 93000 | 260000 |
| Example 218 | 0.66 | 8500 | 13000 |
| Example 219 | 1.2 | 20000 | 17000 |
| Example 220 | 1.9 | 21000 | 11000 |
| Example 221 | 170 | 13000 | 76 |

In Examples 164, 165, 166, 167, 168, 169, 170, 171, 172, 173, 174, 175, 177, 178, 179, 180, 181, 183, 185, 186, 187, 188, and 191, the proportion (%) of the butyrylcholinesterase (BuChE) inhibitory activity at the substrate concentration of 100 nM was 50% or higher. Of these Examples, the proportion was 90% or higher in Examples 164, 165, 166, 167, 170, 171, 172, 173, 177, 178, 179, 180, 185, 186, 187, and 188.

The above results demonstrate that the compound (I) according to the present invention has a high butyrylcholinesterase inhibitory activity. Of the Examples, it was confirmed that the compounds of Examples 9, 15, 16, 17, 20, 31, 34, 35, 42, 44, 45, 47, 49, 50, 51, 53, 54, 57, 91, 96, 98, 99, 100, 104, 115, 116, 117, 118, 119, 120, 133, 148, 153, 155, 214, 216, 217, 218, 219, and 220 all had a much higher butyrylcholinesterase inhibitory activity (selectivity to butyrylcholinesterase) than the acetylcholine esterase inhibitory activity. In particular, it was confirmed that the compound of Example 217 had both the highest butyrylcholinesterase inhibitory activity and the highest selectivity to butyrylcholinesterase. In other words, it is evident that the compound (I) according to the present invention is an excellent butyrylcholinesterase inhibitor and preferable as an agent for preventing, treating, or improving dementia or attention deficit hyperactivity disease.

The invention claimed is:

1. An indoline derivative or a salt thereof represented by the following formula (1):

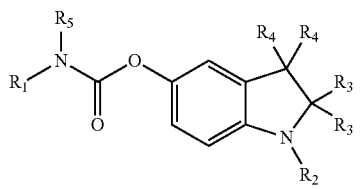

(1)

wherein $R_1$ represents a $C_{2-10}$ alkyl group, a cycloalkyl group, a heterocycloalkyl group, an aryl group which has a substituent, a heteroaryl group, an aryl $C_{1-6}$ alkyl group, a heteroaryl $C_{1-6}$ alkyl group, a cycloalkyl $C_{1-6}$ alkyl group, a heterocycloalkyl $C_{1-6}$ alkyl group, a dihydrofuryl $C_{1-6}$ alkyl group, a $C_{1-6}$ alkenyl group, a tetrahydronaphthyl group, or an indanyl group which may have a substituent; $R_2$ represents an aryl $C_{1-6}$ alkyl group, a cycloalkyl $C_{1-6}$ alkyl group, a heteroaryl $C_{1-6}$ alkyl group, or a heterocycloalkyl $C_{1-6}$ alkyl group which may have a substituent; $R_3$ each independently represents a hydrogen atom, or a $C_{1-10}$ alkyl group or a dialkylaminocarbonyl group which may have a substituent; $R_4$ each independently represents a hydrogen atom, or a $C_{1-10}$ alkyl group which may have a substituent; and $R_5$ represents a hydrogen atom, or a $C_{1-6}$ alkyl group which may have a substituent, provided that $R_1$ and $R_5$ are not a methyl group at the same time if $R_4$ are both a methyl group.

2. The indoline derivative or a salt thereof according to claim 1 represented by the following formula (2):

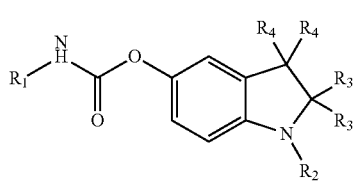

(2)

wherein $R_1$, $R_2$, $R_3$, and $R_4$ have the same meaning as defined in claim 1.

3. The indoline derivative or a salt thereof according to claim 1 represented by the following formula (3):

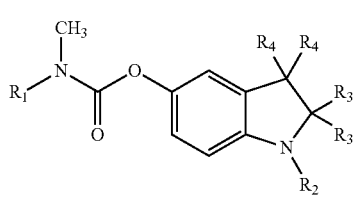

(3)

wherein $R_1$, $R_2$, $R_3$, and $R_4$ have the same meaning as defined in claim 1, provided that $R_1$ is not a methyl group if $R_4$ are both a methyl group.

4. The indoline derivative or a salt thereof according to claim 2 or 3, wherein the $R_1$ is a $C_{2-10}$ alkyl group, a cycloalkyl group, a heterocycloalkyl group, an aryl group which has a substituent, a heteroaryl group, an aryl $C_{1-6}$ alkyl group, a heteroaryl $C_{1-6}$ alkyl group, a cycloalkyl $C_{1-6}$ alkyl group, a heterocycloalkyl $C_{1-6}$ alkyl group, a dihydrofuryl $C_{1-6}$ alkyl group, a $C_{1-6}$ alkenyl group, a tetrahydronaphthyl group, or an indanyl group which may have one or more substituents selected from the group consisting of a $C_{1-10}$ alkyl group, an alkyloxy group, an alkyloxycarbonyl group, an alkylthio group, an acyl group, an alkylamino group, a fluoroalkyl group, a cycloalkyl group, an aryl group, an aryloxy group, an arylalkyl group, a heteroaryl group, a nitro group, a hydroxy group, a cyano group, and a halogen atom and in which two or more substituents may be joined together to form a ring, the $R_2$ is an aryl $C_{1-6}$ alkyl group, a cycloalkyl $C_{1-6}$ alkyl group, a heteroaryl $C_{1-6}$ alkyl group, or a heterocycloalkyl $C_{1-6}$ alkyl group which may have one or more substituents selected from the group consisting of a $C_{1-6}$ alkyl group, an alkyloxy group, an alkylamino group, a dialkylamino group, a fluoroalkyl group, a hydroxy group, an aryl group, an aryloxy group, an arylalkyl group, an acyl group, and a halogen atom and in which two or more substituents may be joined together to form a ring, the $R_3$ is each independently a hydrogen atom, a $C_{1-10}$ alkyl group, or a dialkylaminocarbonyl group, and the $R_4$ is each independently a hydrogen atom, or a $C_{1-10}$ alkyl group which may have a substituent selected from the group consisting of a dialkylaminocarbonyl group and an alkylcarbonylamino group.

5. The indoline derivative or a salt thereof according to claim 2 or 3, wherein the $R_1$ is any group selected from the group consisting of the following (1a) to (1i), the $R_2$ is any group selected from the group consisting of the following (2a) to (2c), the $R_3$ is each independently a hydrogen atom, a $C_{1-10}$ alkyl group, or a dialkylaminocarbonyl group, and the $R_4$ is each independently a hydrogen atom, or a $C_{1-10}$ alkyl group which may have a substituent selected from the group consisting of a dialkylaminocarbonyl group and an alkylcarbonylamino group:

(1a) a $C_{1-10}$ alkyl group which may have a substituent selected from the group consisting of an alkyloxy group, an alkylthio group, and an alkylamino group;
(1b) a cycloalkyl group which may have an alkyl group as a substituent;
(1c) a heterocycloalkyl group which may have an arylalkyl group as a substituent;
(1d) an aryl group which has one or more substituents selected from the group consisting of a $C_{1-10}$ alkyl group, an alkyloxy group, an alkyloxycarbonyl group, an alkylthio group, an acyl group, an alkylamino group, a fluoroalkyl group, a cycloalkyl group, an aryl group, an aryloxy group, a heteroaryl group, a nitro group, a halogen atom, and a cyano group;
(1e) a heterocycloalkyl $C_{1-6}$ alkyl group which may have an alkyl group or an arylalkyl group as a substituent;
(1f) an aryl $C_{1-6}$ alkyl group which may have one or more substituents selected from the group consisting of an alkyl group, an alkyloxy group, and a halogen atom;
(1g) a dihydrofuryl $C_{1-6}$ alkyl group which may have one or two alkyloxy groups as a substituent;
(1h) a heteroaryl group, a cycloalkyl $C_{1-6}$ alkyl group, a heteroaryl $C_{1-6}$ alkyl group, or a $C_{1-6}$ alkenyl group;
(1i) a benzodioxolyl group, an indanyl group, a dihydrobenzofuryl group, a dihydrobenzodioxynyl group, a benzoxolyl group, or a tetrahydronaphthyl group;
(2a) a phenyl $C_{1-6}$ alkyl group or a naphthyl $C_{1-6}$ alkyl group which may have one or more substituents selected from the group consisting of an alkyloxy group, a fluoroalkyl group, an alkylamino group, a dialkylamino group, an acyl group, a hydroxy group, an aryloxy group, and a halogen atom;
(2b) a heteroaryl $C_{1-6}$ alkyl group which may have an arylalkyl group or an alkyl group as a substituent; and
(2c) a cycloalkyl $C_{1-6}$ alkyl group, or a heterocycloalkyl $C_{1-6}$ alkyl group.

6. The indoline derivative or a salt thereof according to claim 2 or 3, wherein the $R_1$ is any group selected from the group consisting of the following (1a') to (1h'), the $R_2$ is any group selected from the group consisting of the following (2a') to (2c'), the $R_3$ is each independently a hydrogen atom, a $C_{1-10}$ alkyl group, or a dialkylaminocarbonyl group, and the $R_4$ is each independently a hydrogen atom, or a $C_{1-10}$ alkyl group which may have a substituent selected from the group consisting of a dialkylaminocarbonyl group and an alkylcarbonylamino group:

(1a') a $C_{1-10}$ alkyl group which may have a substituent selected from the group consisting of a methoxy group, a methylthio group, a furfurylthio group, and a dimethylamino group;
(1b') a cyclopropyl group, a cyclohexyl group, a cyclooctyl group, or a 4-tert-butylcyclohexyl group;
(1c') a piperidinyl group which may have a phenyl $C_{1-6}$ alkyl group as a substituent;
(1d') a phenyl group which has one or more substituents selected from the group consisting of a methyl group, an isopropyl group, an n-butyl group, a t-butyl group, a methoxy group, an n-hexyloxy group, an ethoxycarbonyl group, a methylthio group, an acetyl group, a dimethylamino group, a trifluoromethyl group, a cyclohexyl group, a phenyl group, a phenoxy group, a 1H-pyrrol-1-yl group, a nitro group, a halogen atom, and a cyano group;
(1e') a tetrahydrofuryl $C_{1-6}$ alkyl group, a piperidinyl $C_{1-6}$ alkyl group, or a pyrrolidinyl $C_{1-6}$ alkyl group which may have an alkyl group or a phenyl $C_{1-6}$ alkyl group as a substituent;
(1f') a phenyl $C_{1-6}$ alkyl group or a naphthyl $C_{1-6}$ alkyl group which may have one or more substituents selected from the group consisting of a methyl group, an isopropyl group, a methoxy group, an isopropyloxy group, and a halogen atom;
(1g') a dihydrofuryl $C_{1-6}$ alkyl group which may have one or two methoxy groups as a substituent;
(1h') a quinolyl group, a pyridyl group, a cyclohexyl $C_{1-6}$ alkyl group, an 1-adamantyl $C_{1-6}$ alkyl group, a furyl $C_{1-6}$ alkyl group, a pyridyl $C_{1-6}$ alkyl group, a thienyl $C_{1-6}$ alkyl group, a 2-methylallyl group, a benzodioxolyl group, an indanyl group, a dihydrobenzofuryl group, a dihydrobenzodioxynyl group, or a tetrahydronaphthyl group;
(2a') a phenyl $C_{1-6}$ alkyl group or a naphthyl $C_{1-6}$ alkyl group which may have one or more substituents selected from the group consisting of a methoxy group, a trifluoromethyl group, a dimethylamino group, an acetyl group, a hydroxy group, a phenoxy group, a 3-dimethylaminopropoxy group, a methoxycarbonyl group, and a halogen atom;
(2b') an indolyl $C_{1-6}$ alkyl group which may have a benzyl group or a methyl group as a substituent; and
(2c') a cyclohexyl $C_{1-6}$ alkyl group, a pyridyl $C_{1-6}$ alkyl group, a furyl $C_{1-6}$ alkyl group, a pyrrolyl $C_{1-6}$ alkyl group, a quinolyl $C_{1-6}$ alkyl group, a benzodioxolyl $C_{1-6}$ alkyl group, or a tetrahydrofuryl $C_{1-6}$ alkyl group.

7. The indoline derivative or a salt thereof according to claim 2 or 3, wherein the $R_1$ is an ethyl group, an n-propyl group, an n-hexyl group, a 2-heptyl group, a 2-methylpropyl group, a 2,2-dimethylpropyl group, a 3,3-dimethylbutyl group, a 3-methoxypropyl group, a 1-methoxybutan-2-yl group, a 3-(dimethylamino)propyl group, a 2-(dimethylamino)ethyl group, a 3-dimethylamino-2,2-dimethylpropyl group, a 3-methylthiopropyl group, a 2-(furfurylthio)ethyl group, a cyclohexyl group, a cyclopropyl group, a cyclooctyl group, a 4-tert-butylcyclohexyl group, a cyclohexylmethyl group, a 1-adamantanemethyl group, a 2-tetrahydrofurylmethyl group, a 3-tetrahydrofurylmethyl group, a 4-tetrahydropyranylmethyl group, a 2-(1-benzylpiperidin-4-yl)ethyl group, a 4-methylphenyl group, a 4-isopropylphenyl group, a 3,4-dimethylphenyl group, a 4-methoxyphenyl group, a 4-dimethylaminophenyl group, a 3,4-dimethoxyphenyl group, a 2,3-dihydro-1,4-benzodioxin-6-yl group, a 5-benzo[d][1,3]dioxolyl group, a 5-indanyl group, a 2,3-dihydro-1-benzofuran-5-yl group, a benzyl group, a phenethyl group, a 1-phenylethyl group, a 4-isopropylphenethyl group, a 4-methylphenethyl group, a 4-methylbenzyl group, a 2-methylphenethyl group, a 2,4-dimethylphenethyl group, a 4-methoxybenzyl group, a 3-methoxybenzyl group, a 4-methoxyphenethyl group, a 2-methoxyphenethyl group, a 1-(p-tolyl)ethyl group, a 4-chlorophenethyl group, a 2,4-dichlorophenethyl group, a furfuryl group, a 2-thiophenemethyl group, a 2-pyridylmethyl group, a 4-pyridylmethyl group, a 2-(4-pyridyl)ethyl group, a 2-(3-pyridyl)ethyl group, a 1-benzylpiperidin-4-yl group, a 2-methylallyl group, a 1,2,3,4-tetrahydronaphthalen-1-yl group, a (2,5-dihydro-2,5-dimethoxyfuran-2-yl)methyl group, or a 2-indanyl group, the $R_2$ is a benzyl group, a 3-hydroxybenzyl group, a 2-hydroxybenzyl group, a 4-hydroxybenzyl group, a 4-hydroxy-3-methoxybenzyl group, a phenethyl group, a 4-pyridylmethyl group, a 3-pyridylmethyl group, a 2-pyridylmethyl group, an indol-3-ylmethyl group, a (pyrrol-2-yl)methyl group, or a cyclohexylmethyl group, the $R_3$ is each independently a hydrogen atom, a methyl group, or a di-n-propylaminocarbonyl group, and the $R_4$ is each independently a hydrogen atom, a methyl group, a 2-acetamideethyl group, or a di-n-propylaminocarbonylmethyl group.

8. The indoline derivative or a salt thereof according to claim 1, which is selected from the following compounds: (1) 1-benzylindolin-5-yl 4-isopropyl phenyl carbamate, (2) 1-phenethyl indolin-5-yl 4-isopropyl phenyl carbamate, (3) 1-benzylindolin-5-yl 4-methoxyphenyl carbamate, (4) 1-benzylindolin-5-yl 2,3-dihydro-1,4-benzodioxin-6-yl carbamate, (6) 1-benzylindolin-5-yl 5-benzo[d][1,3]dioxolyl carbamate, (7) 1-benzylindolin-5-yl 2,3-dihydro-1-benzofuran-5-yl carbamate, (8) 1-benzylindolin-5-yl benzylcarbamate, (9) 1-benzylindolin-5-yl phenethyl carbamate, (10) 1-benzylindolin-5-yl n-hexyl carbamate, (11) 1-benzylindolin-5-yl furfuryl carbamate, (12) 1-benzylindolin-5-yl (S)-1-phenyl ethyl carbamate, (13) 1-benzylindolin-5-yl cyclohexyl carbamate, (14) 1-(4-pyridyl methyl)indolin-5-yl 4-isopropyl phenyl carbamate, (15) 1-(3-pyridyl methyl)indolin-5-yl 4-isopropyl phenyl carbamate, (16) 1-benzylindolin-5-yl 4-methoxybenzylcarbamate, (17) 1-benzylindolin-5-yl 4-methoxyphenethyl carbamate, (18) 1-benzylindolin-5-yl 4-isopropyl phenethyl carbamate, (19) 1-benzylindolin-5-yl cyclohexyl methyl carbamate, (20) 1-benzylindolin-5-yl 2-methyl propyl carbamate, (21) 1-benzylindolin-5-yl cyclopropyl carbamate, (22) 1-benzylindolin-5-yl 3,3-dimethyl butyl carbamate, (23) 1-benzylindolin-5-yl 4-tert-butyl cyclohexyl carbamate, (24) 1-benzylindolin-5-yl 2-indanyl carbamate, (25) 1-benzylindolin-5-yl cyclooctyl carbamate, (26) 1-benzylindolin-5-yl 1-methoxybutan-2-yl carbamate, (27) 1-benzylindolin-5-yl 1-adamantane methyl carbamate, (28) 1-benzylindolin-5-yl 3-methyl thiopropyl carbamate, (29) 1-benzylindolin-5-yl 2-heptyl carbamate, (30) 1-benzylindolin-5-yl 2-tetrahydrofuryl methyl carbamate, (31) 1-benzylindolin-5-yl 2-methyl allyl carbamate, (32) 1-benzylindolin-5-yl 2-(furfuryl thio)ethyl carbamate, (33) 1-benzylindolin-5-yl 4-methyl phenyl carbamate, (34) 1-benzylindolin-5-yl ethyl carbamate, (35) 1-(2-pyridyl methyl)indolin-5-yl 4-isopropyl phenyl carbamate, (36) 1-(3-hydroxybenzyl)indolin-5-yl 4-isopropyl phenyl carbamate, (37) 1-[(pyrrol-2-yl)methyl]indolin-5-yl 4-isopropyl phenyl carbamate, (38) 1-(2-hydroxybenzyl)indolin-5-yl 4-isopropyl phenyl carbamate, (39) 1-(4-hydroxy-3-methoxybenzyl)indolin-5-yl 4-isopropyl phenyl carbamate, (40) 1-(cyclohexylmethyl)indolin-5-yl 4-isopropyl phenyl carbamate, (41) 1-(4-hydroxybenzyl)indolin-5-yl 4-isopropyl phenyl carbamate, (42) 1-(indol-3-yl methyl)indolin-5-yl 4-isopropyl phenyl carbamate, (43) 1-benzylindolin-5-yl 5-indanyl carbamate, (44) 1-benzylindolin-5-yl 4-methyl phenethyl carbamate, (45) 1-benzylindolin-5-yl 1,2,3,4-tetrahydronaphthalen-1-yl carbamate, (46) 1-benzylindolin-5-yl 1-(p-tolyl)ethyl carbamate, (47) 1-benzylindolin-5-yl 2-thiophene methyl carbamate, (48) 1-benzylindolin-5-yl 4-methyl benzylcarbamate, (49) 1-benzylindolin-5-yl 3-methoxybenzylcarbamate, (50) 1-benzylindolin-5-yl 2-pyridyl methyl carbamate, (51) 1-benzylindolin-5-yl 4-pyridyl methyl carbamate, (52) 1-benzylindolin-5-yl 4-chlorophenethyl carbamate, (53) 1-benzylindolin-5-yl 3,4-dimethyl phenyl carbamate, (54) 1-benzylindolin-5-yl n-propyl carbamate, (55) 1-benzylindolin-5-yl 2-methyl phenethyl carbamate, (56) 1-benzylindolin-5-yl 2,4-dimethyl phenethyl carbamate, (57) 1-benzylindolin-5-yl 2-methoxyphenethyl carbamate, (58) 1-benzylindolin-5-yl 2,4-dichlorophenethyl carbamate, (59) 1-benzylindolin-5-yl 2-(4-pyridyl)ethyl carbamate, (60) 1-benzylindolin-5-yl 2-(3-pyridyl)ethyl carbamate, (61) 1-benzylindolin-5-yl (2,5-dihydro-2,5-dimethoxyfuran-2-yl)methyl carbamate, (64) 1-benzylindolin-5-yl 4-dimethyl aminophenyl carbamate, (65) 1-benzylindolin-5-yl 3-(dimethylamino)propyl carbamate, (66) 1-benzylindolin-5-yl 1-benzylpiperidin-4-yl carbamate, (67) 1-benzylindolin-5-yl 2-(1-benzylpiperidin-4-yl)ethyl carbamate, (68) 1-benzylindolin-5-yl 3,4-dimethoxyphenyl carbamate, (69) 1-benzyl-3,3-dimethyl indolin-5-yl 4-isopropyl phenyl carbamate, (70) 1-benzyl-3-methylindolin-5-yl 4-isopropyl phenyl carbamate, (71) 1-(2-pyridyl methyl)indolin-5-yl n-hexyl carbamate, (72) 1-(2-pyridyl methyl)indolin-5-yl cyclohexyl methyl carbamate, (73) 1-(2-pyridyl methyl)indolin-5-yl cyclohexyl carbamate, (74) 1-(2-pyridyl methyl)indolin-5-yl benzylcarbamate, (75) 1-(2-pyridyl methyl)indolin-5-yl 4-dimethyl aminophenyl carbamate, (76) 1-benzylindolin-5-yl 2,2-dimethyl propyl carbamate, (77) 1-benzylindolin-5-yl 3-tetrahydrofuryl methyl carbamate, (78) 1-benzylindolin-5-yl 3-dimethylamino-2,2-dimethyl propyl carbamate, (79) 3-(2-acetamide ethyl)-1-benzylindolin-5-yl 4-isopropyl phenyl carbamate, (80) 1-benzyl-3-(di-n-propyl aminocarbonyl methyl)indolin-5-yl 4-isopropyl phenyl carbamate, (81) 1-benzyl-3-(di-n-propyl aminocarbonyl methyl)-2-methylindolin-5-yl 4-isopropyl phenyl carbamate, (82) O-(1-benzylindolin-5-yl)-N-(cyclohexylmethyl)-N-methyl carbamate, (83) O-(1-benzyl-3,3-dimethyl indolin-5-yl)-N-(cyclohexylmethyl)-N-methyl carbamate, (84) O-(1-benzyl-3,3-dimethyl indolin-5-yl)-N-methyl-N-(4-tetrahydropyranyl methyl)carbamate, (85) N-methyl-O-[1-(2-pyridyl methyl)-3,3-dimethyl indolin-5-yl]-N-(4-tetrahydropyranyl methyl)carbamate, (86) N-methyl-O-[1-(3-pyridyl methyl)-3,3-dimethyl indolin-5-yl]-N(4-tetrahydropyranyl methyl)carbamate, and (87) N-methyl-O-[1-(4-pyridyl methyl)-3,3-dimethyl indolin-5-yl]-N(4-tetrahydropyranyl methyl)carbamate.

9. A medicament comprising at least one selected from indoline derivatives or salts thereof according to claim 1 as an active ingredient.

10. The medicament according to claim 9, which is a butyrylcholinesterase inhibitor.

11. The medicament according to claim 9, which is an agent for treating or improving dementia or attention deficit hyperactivity disease, wherein the dementia is not Alzheimer-type dementia.

12. The indoline derivative or a salt thereof according to claim 1, wherein $R_1$ represents a tetrahydropyranylmethyl group.

13. The indoline derivative or a salt thereof according to claim 1, wherein the indoline derivative is O-(1-benzyl-3,3-dimethylindolin-5-yl)-N-methyl-N-(4-tetrahydropyranylmethyl)carbamate.

14. The indoline derivative or a salt thereof according to claim 1, wherein the indoline derivative is 1-benzylindolin-5-yl cyclohexylmethylcarbamate.

15. The indoline derivative or a salt thereof according to claim 1, wherein the indoline derivative is N-methyl-O-[1-(2-pyridylmethyl)-3,3-dimethylindolin-5-yl]-N-(4-tetrahydropyranylmethyl)carbamate.

16. The indoline derivative or a salt thereof according to claim 1, wherein the indoline derivative is N-methyl-O-[1-(3-pyridylmethyl)-3,3-dimethylindolin-5-yl]-N-(4-tetrahydropyranylmethyl)carbamate.

17. The indoline derivative or a salt thereof according to claim 1, wherein the indoline derivative is N-methyl-O-[1-(4-pyridylmethyl)-3,3-dimethylindolin-5-yl]-N-(4-tetrahydropyranylmethyl)carbamate.

* * * * *